(12) United States Patent
Fujiwara et al.

(10) Patent No.: US 7,666,678 B2
(45) Date of Patent: Feb. 23, 2010

(54) PROTEINS IMPARTING BORON-TOLERANCE AND GENES THEREOF

(75) Inventors: Toru Fujiwara, Tokyo (JP); Akira Nozawa, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 11/522,168

(22) Filed: Sep. 15, 2006

(65) Prior Publication Data

US 2007/0079394 A1 Apr. 5, 2007

Related U.S. Application Data

(63) Continuation-in-part of application No. PCT/JP2005/004553, filed on Mar. 15, 2005.

(30) Foreign Application Priority Data

Mar. 15, 2004 (JP) ............................. 2004-073324

(51) Int. Cl.
C12N 15/81 (2006.01)
(52) U.S. Cl. ..................................... 435/483
(58) Field of Classification Search ........................ None
See application file for complete search history.

(56) References Cited

U.S. PATENT DOCUMENTS

2006/0150283 A1* 7/2006 Alexandrov et al. ........ 800/288

FOREIGN PATENT DOCUMENTS

EP 1033405 9/2000

OTHER PUBLICATIONS

Town et al. (GenBank, NCBI, Sequence Accession No. NM_119572, Published Jan. 30, 2002).*
Town et al. (NCBI, GenBank, Sequence Accession No. NM_103643, pp. 1-2, Published Aug. 20, 2002).*
Nozawa et al. (Biosci. Biotechnol. Biochem., 70:1724-1730, 2006).*
Miwa et al. (Science, 318:1417, 2007).*
Wells, (Biochemistry 29:8509-8517, 1990).*
Ngo et al., (The Protein Folding Problem and Tertiary Structure Prediction, K. Merz., and S. Le Grand (eds.) pp. 492-495,1994).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Maniatis et al. (Molecular Cloning: A Laboratory Manual, Cold Spring Harbor Laboratory, 1982).*
Hilson et al. Molecular characterization of PAB2, a member of the multigene family coding for poly(A)-binding proteins in *Arabidopsis thaliana*. Plant Physiology 103(2): 525-533, 1993.
Kobayashi et al. Analysis of transport property in Boron transporters, BOR1 and YNL275w. Nippon Dojo Hiryo Gakkai Koen Yoshishu 9-72: 49: 88, 2003.

Miwa et al. Identification of boron transporter and the roles in boron transportation of plants. Brain Techno News 95: 12-15, 2003.
Fujiwara. Identification of boron transporter. Nippon Nogei Kagakukai Taikai Koen Yoshishu 3A14a13: 196, 2003.
Takano et al. *Arabidopsis* boron transporter for xylem loading. Nature 420: 337-340, 2002.
Database UNIPROTKB/TREMBL: Database Accession No. Q9SX80: V.S. Vysotskaia, et al., F16N3.34 Protein, May 1, 2000.
Database EMBL/GENBANK: Database Accession No. BX814965: V. Castelli, et al., *Arabidopsis thaliana* Full-Length cDNA Complete Sequence From Clone GSLTLS20ZE04, Feb. 6, 2004.
Database UNIPROTKB/TREMBL: Database Accession No. AAG52531: N. Alexandrov, et al., *Arabidopsis thaliana* Protein Fragment Seq ID No. 66787, Oct. 18, 2000.
Database EMBL/GENBANK/DDBJ: Database Accession No. ABZ12386: J.F. Harper, et al., *Arabidopsis thaliana* Stress Regulated Gene Seq ID No. 191, Jan. 21, 2003.
Database EMBL/GENBANK/DDBJ: Database Accession No. ABZ12316: J.F. Harper, et al., *Arabidopsis thaliana* Stress Regulated Gene Seq ID No. 121, Jan. 21, 2003.
Database UNIPROTKB/TREMBL: Database Accession No. Q9LNC9: H. Sakano, et al., F9P14.4 Protein, Oct. 1, 2000.
Database UNIPROTKB/TREMBL: Database Accession No. AAY77980: J. H. Lee, et al, Thaliana Environmental Stress Tolerance Related Protein, Jun. 14, 2000.
Database EMBL/GENBANK/DDBJ Database Accession No. ABZ14528: J. F. Harper, et al., *Arabidopsis thaliana* Stress Regulated Gene Seq ID No. 2333, Jan. 21, 2003.
Database UNIPROTKB/TREMBL: Database Accession No. Q9FPJ8: P. Shinn, et al., AT5g54900, Mar. 1, 2001.
Database EMBL/GENBANK/DDBJ: Database Accession No. AAC45412: N. Alexandrov, et al., *Arabidopsis thaliana* DNA Fragment Seq ID No. 46405, Oct. 18, 2000.
Database UNIPROTKB/TREMBL: Database Accession No. Q9SAB3: V.S. Vysotskaia, et al., F25C20.21 Protein, May 1, 2000.
Database EMBL/GENBANK/DDBJ: Database Accession No. BT008494: Cheuk R. et al., *Arabidopsis thaliana* At1g11650 Gene, Complete CDS, May 16, 2003.
Database UNIPROTKB/TREMBL: Database Accession No. Q93W34: A. Southwick, et al., Putative DNA Binding Protein, Dec. 1, 2001.
Database EMBL/GENBANK/DDBJ: Database Accession No. AY062999: K. Yamada, et al., *Arabidopsis thaliana* Putative DNA Binding Protein (At4g27000) mRNA, Complete cds, Nov. 28, 2001.

(Continued)

*Primary Examiner*—Vinod Kumar
(74) *Attorney, Agent, or Firm*—Frommer Lawrence & Haug LLP; Thomas J. Kowalski

(57) ABSTRACT

The present invention provides genes and proteins having possibilities to generate plants having tolerance against excessive boron, which can confer a boric acid tolerance to organisms. 5 types of genes that can confer a boric acid tolerance to yeast, such as AtPAB2, AtRBP47c', AtRPS20B, AtMYB13 and AtMYB68, AtRBP45a, AtRBP45b, AtRBP45c, AtRBP45d, AtRBP47a, AtRBP47b, AtRBP47c, AtUBP1a, AtUBP1b and AtUBP1c which were found by expressing several genes of higher plant *Arabidopsis thaliana* in yeast that is a organism model of eukaryote. Further, a key to the toxicity mechanism of boric acid exists in the specific inhibition of splicing, and a gene related to enhancement of splicing efficiency also confers a boric acid tolerance.

1 Claim, 10 Drawing Sheets

OTHER PUBLICATIONS

Database UNIPROTKB/TREMBL: Database Accession No. Q8VXZ9: K. Yamada, et al., Putative DNA Binding Protein ACBF Mar. 1, 2002.

Database EMBL/GENBANK/DDBJ: Database Accession No. AY114004: K. Yamada, et al., *Arabidopsis thaliana* Putative DNA Binding Protein ACBF (At5g19350) mRNA, Complete cds, Jun. 5, 2002.

Database UNIPROTKB/TREMBL: Database Accession No. Q9FX88: N.A. Federspiel, et al., Putative DNA Binding Protein, Mar. I, 2001.

Database EMBL/GENBANK/DDBJ: Database Accession No. AAC41871: N. Alexandrov, et al, *Arabidopsis thaliana* DNA Fragment Seq ID No. 33446, Oct. 17, 2000.

Database UNIPROTKB/TREMBL: Database Accession No. AAG28286: N. Alexandrov, et al, *Arabidopsis thaliana* DNA Fragment Seq ID No. 33447, Oct. 17, 2000.

Database UNIPROTKB/TREMBL: Database Accession No. Q9SX79: V. S. Vysotskaia, et al., F16N3.24 Protein, May 1, 2000.

Database EMBL/GENBANK/DDBJ: Database Accession No. ACC46515: N. Alexandrov, et al, *Arabidopsis thaliana* DNA Fragment Seq ID No. 50421, Oct. 18, 2000.

Database UNIPROTKB/TREMBL: Database Accession No. Q9SYG4: V.S. Vysotskaia, et al., F15I1.16 Protein, May 1, 2000.

Database EMBL/GENBANK/DDBJ: Database Accession No. AAC43477: N. Alexandrov, et al, *Arabidopsis thaliana* DNA Fragment Seq ID No. 39382, Oct. 17, 2000.

Database UNIPROTKB/TREMBL: Database Accession No. Q9LQ19: N.A. Federspiel, et al., Putative RNA Binding Protein (At1g17370), Oct. 1, 2000.

Database EMBL/GENBANK/DDBJ: Database Accession No. AAC40033: N. Alexandrov, et al, *Arabidopsis thaliana* DNA Fragment Seq ID No. 36800, Oct. 17, 2000.

Database UNIPROTKB/TREMBL: Database Accession No. Q9LJH8: T. Kaneko, et al, RNA Binding Protein Nucleolysin; Oligouridylate Binding Protein, Oct. 1, 2000.

Database EMBL/GENBANK/DDBJ: Database Accession No. BT004540: R. Cheuk, et al., *Arabidopsis thaliana* AT3g14100/ MAG2_5 Gene, Complete cds, Feb. 20, 2003.

Database UNIPROTKB/TREMBL: Database Accession No. Q8RXR5: K. Yamada, et al., Putative Poly(A)-Binding Protein, Jun. 1, 2002.

Database EMBL: Database Accession No. BT002354: K. Yamada, et al., *Arabidopsis thaliana* Clone C104970 Putative Polyadenylate-Binding Protein 2 (PABP2) (At4g34110) mRNA, Complete cds, Dec. 17, 2002.

Y. Chantachume, et al., Screening for Boron Tolerance In Wheat (*T. aestivum*) by Solution Culture In Filter Paper, Plant and Soil (1995) vol. 177, p. 249-254.

V. Damagnez, et al., Identification Of A Gene Encoding The Predicted Ribosomal Protein L7b Divergently Transcribed From POL1 In Fission Yeast *Schizosaccharomyces pombe*, Nucleic Acids Research (1991) vol. 19, No. 5, p. 1099-1104.

V. Lippuner, et al., Two Classes Of Plant cDNA Clones Differentially Complement Yeast Calcineurin Mutants And Increase Salt Tolerance Of Wild-Type Yeast*, Journal of Biological Chemistry (1996) vol. 271, No. 22, p. 12859-12866.

M. Minet, et al., Complementation Of *Saccharomyces cerevisiae* Auxotrophic Mutants By *Arabidopsis thaliana* cDNAs, The Plant Journal (1992) vol. 2, No. 3, p. 417-422.

R. Zhao, et al., Expression and Characterization Of The Anion Transporter Homologue YNL275w In *Saccharomyces cerevisiae*, American Journal of Physiology (2001) vol. 281, p. C38-C48.

\* cited by examiner

US 7,666,678 B2

PROTEINS IMPARTING BORON-TOLERANCE AND GENES THEREOF

INCORPORATION BY REFERENCE

This application is a continuation-in-part application of international patent application Serial No. PCT/JP2005/004553 filed Mar. 15, 2005, which published as international publication No. WO 20050/087928 on Sep. 22, 2005, which claims priority to Japanese patent application Serial No. JP 2004-073324 filed Mar. 4, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a protein conferring a boric acid tolerance in *Arabidopsis thaliana* and a gene thereof, a recombinant vector containing the gene, a transformant introduced with the recombinant vector, and a screening method of a gene conferring a boric acid tolerance.

BACKGROUND OF THE INVENTION

Boron is one of the essential trace elements for higher plants (e.g., see nonpatent document 1). As boron also has toxicity, by over ingesting it, plant growth is inhibited and animal dies of acute intoxication. Boron exists in uncharged molecule state in soil solution. Therefore, boron eluviates with relative ease and boron deficiency is easily developed in agricultural crops. Lowering of yield point and quality in agriculture caused by boron deficiency is reported in 130 varieties in 80 or more countries worldwide including Japan (e.g., see nonpatent document 2). Boron is also known to have a restricted range of optimal concentration compared with other elements, and has little difference between the concentrations at which deficiency symptoms develop and excess symptoms develop. Therefore, the quantity adjustment of boron fertilizer application in agriculture is considered to be difficult. Especially, when boron is fertilized excessively, removal of the boron is difficult and crop production in the agricultural land would be affected. Further, as boron is contained in tap water, damages caused-by excessive boron often become a problem in drylands when irrigated agriculture is performed. In addition to agricultural lands over-fertilized with boron in this way, land areas with high concentration of boron are found worldwide. Countries having such areas have an important agenda for taking measures against damages caused by excessive boron in agricultural policy. Further, as boron is also present in agents for treating metal surface and bleaches, wastewater from factories using these agents and bleaches contains boron in appreciable quantities. Although lethal dose of boron for human is 15-20 mg, it is known that various disorders involving digestive organs and nervous systems are developed with less than the lethal dose of boron. At present, the amount of boron contained in wastewater from factories is becoming an issue.

Recently, a role of boron in plants has been elucidated. It was elucidated that boron bridges pectic polysaccharides in cell walls (e.g., see nonpatent document 3), and showed that the crossbridges are essential for plant growth (e.g., see nonpatent document 4). This is the first knowledge regarding the physiological function of boron at a molecular level in plants. On the other hand, many unclear points remains to be elucidated in the boron transportation mechanism in plants. It was thought for a long time that boron enters into cells by passive diffusion of lipid bilayer, and is transported in plant body by transpiration stream (e.g., see nonpatent document 5). In the meantime, it was known that nutrient conditions of boron, which are suited for growth, differ significantly among species and cultivars. Although absorption, translocation and difference of use efficiency were exemplified as possible causes, molecules of the contributing factors were unknown. In recent years, transportation via channels has been proposed (e.g., see nonpatent document 6), but the evidence was only in vitro experiments using an expression system or a membrane vesicle in Xenopus laevis oocytes, and it was not shown whether these channel molecules were involved in the boron transportation in actual individual plants. Further, the presence of active transport by a transporter was suggested from absorption experiments in roots of sunflower roots (e.g., see nonpatent document 7), however, the responsible transporter was not identified.

The present inventors isolated an efflux boron tolerance protein BOR1 from a plant model, *Arabidopsis thaliana* for the first time in animate nature (e.g., see patent document 1). It is thought that BOR1 is responsible for an active boron transportation to vessels under nutrient conditions of lower boron (e.g., see nonpatent document 8). Further, YNL275w of yeast, aside from BOR1 is known as tolerance being responsible for boron transportation (e.g., see nonpatent document 9).

Further, as described above, Boron (B) is an essential trace nutrient for plants (e.g., see nonpatent document 10) and animals (e.g., see nonpatent document 11), but toxic at high concentrations (e.g., see nonpatent documents 12 and 13). Naturally occurring soils containing high concentration of B are distributed across the world and human activities such as fertilization with B, fossil combustion, and irrigation using B-containing water created an environment of high boron concentration (e.g., see nonpatent documents 12 and 13).

Symptoms of B toxicity in plants include chlorosis in leaf margin (e.g., see nonpatent document 13) and fruit disorder and/or bark necrosis (e.g., see nonpatent document 14). Excess B reduces the yield and quality of crops. B toxicity is a major obstruction of agricultural production worldwide. B is also toxic to animals and microorganisms at high concentration. The lethal dose of B is estimated to be about 140 mg/kg for adults and about 270 mg/kg for infants (.e.g., see nonpatent documents 15 and 16) . Long term-high B intake leads to poor appetite, nausea, weight loss, and decreased sexual activity for humans (e.g., see nonpatent document 17). At present, the acceptable safe intake of B for adults is suggested to be 13 mg per day (e.g., see nonpatent document 18). B has been contained in food preservatives for its sterilization effect on microorganisms (e.g., see nonpatent document 19) . In addition, B has been used as insecticides for many years, especially against cockroaches (e.g., see nonpatent document 20).

In the last several decades since B toxicity has been recognized, a number of studies were conducted to investigate toxic effects of B. Those were mostly physiological studies. For example, in soybean leaves, the activity of allantoate amidohydrolase is decreased by boric acid (e.g., see nonpatent document 21). The inhibitions of malate dehydrogenase and isocitrate dehydrogenase activities by B were observed in *Chara corallina* (e.g., see nonpatent document 22). A negative correlation between placental B levels and delta-aminolevulinic acid dehydratase activities involved in synthesis of porphobilinogen (an intermediate of porphyrin synthesis) in newborns has been also reported (e.g., see nonpatent document 23).

Solubilized borates are thought to play a major role in B toxicity. Boric acids in cells are partially converted into borates due to the higher internal pH. When boric acids with high concentration are supplied to cells, intracellular borate concentration rises to form borate complexes with a variety of cis-diol containing intracellular molecules. These cis-diols containing molecules include $NAD^+$, ATP, S-Ado Met, RNA and several sugars (e.g., see nonpatent documents 24 and 25). Since these molecules are used as coenzymes and/or substrates for a number of enzymes, binding of borates is likely to induce loss of function or alteration of enzyme activities, inhibition of biochemical reactions, and finally metabolic disorders. Despite of the accumulation of biochemical and physiological analysis and speculation related to the toxic effect of B, molecular mechanism of B toxicity that leads to cell death has not been elucidated.

Patent document 1: Japanese Laid-Open Patent Application NO.2002-262872

Nonpatent document 1: Loomis, W. D.; Durst, R. W. (1992) Chemistry and biology of boron. Biofactors 3: 229-239

Nonpatent document 2: Shorrocks, V. M. (1997) The occurrence and correction of boron deficiency. Plant and Soil 193: 121-148

Nonpatent document 3: Matoh, T.; Ishigaki, K. I.; Ohno, K; Azuma, J. I. (1993) Isolation and characterization of a boron-polysaccharide complex from radish roots. Plant Cell Physiol. 34: 639-642

Nonpatent document 4: O'Neill, M. A.; Eberhard, S.; Albersheim, P.; Darvill, A. G. (2001) Requirement of borate cross-linking of cell wall rhamnogalacturonan II for *Arabidopsis* growth. Science 294: 846-849

Nonpatent document 5: Marschner, H. (1995) Mineral Nutritin of Higher Plants, 2nd ed. Academic Press, San Diego, Calif.

Nonpatent document 6: Dordas, C.; Chrispeels, M. J.; Brown, P. H. (2000) Permeability and channel-mediated transport of boric acid across membrane vesicles isolated from Squash roots. Plant Physiol. 124: 1349-1362

Nonpatent document 7: Dannel, F.; Heidrun, P; Romheld, V. (2000) Characterization of root boron pools, boron uptake and boron translocation in sunflower using the stable isotope 10B and 11B. Aust. J. Plant Physiol. 156: 756-761

Nonpatent document 8: Takano, J.; Noguchi, K.;Yasumori, M.; Kobayashi, M.; Gajdos, Z.; Miwa, K.; Hayashi, H.; Yoneyama, T.; Fujiwara, T. (2002) *Arabidopsis* boron transporter for xylem loading. Nature 420 (6913): 337-340

Nonpatent document 9: Zhao, R. M.; Reithmeier, R. A. F. (2001) Expression and characterization of the anion transporter homologue YNL275w in *Saccharomyces cerevisiae*. American Journal of Physiology-Cell Physiology 281 (1): C33-C45

Nonpatent document 10: Warington, K. (1923) Ann. Bot. 37, 629-672

Nonpatent document 11: Park, M., Li, Q., Shcheynikov, N., Zeng, W., & Muallern, S. (2004) Mol. Cell 16, 331-341

Nonpatent document 12: Gupta, U. C., Jame, Y. W., Campbell, C. A., Leyshon, A. J., & Nicholaichuk, W. (1985) Can. J. Soil Sci.65, 381-409

Nonpatent document 13: Nable, R. O., Banuelos, G. S., & Paull, J. G. (1997) Plant Soil 193, 181-198

Nonpatent document 14: Brown, P. H., & Hu, H. (1996). Ann. Bot. 77, 497-505

Nonpatent document 15: Young, E. G., Smith, R. P., & MacIntosh, O. C. (1949) Can. Med. Assoc. J. 61, 447-450

Nonpatent document 16: Arena, J. M., & Drew, R. H. (1986) in Poisoning, (C. C. Thomas, Splingfield). pp. 131

Nonpatent document 17: Hunt, C. D. (1993) in Encyclopedia of Food Science, Food Technology and Nutrition, vol. 1, eds. Macrae, R., Robinson, R. K. & Sadler, M J. (Academic Press, London), pp 440-447

Nonpatent document 18: WHO/FAO/IAEA (1996) in Trace Elements in Human Nutrition and Health, (World Health Organization, Geneva), pp. 175-179

Nonpatent document 19: Nielsen, F. H. (1997) Plant Soil 193, 199-208

Nonpatent document 20: Cochran, D. G. (1995) Experientia 51, 561-563

Nonpatent document 21: Lukaszewski, K. M., Blevins, D. G., & Randall, D. D. (1992) Plant Physiol. 99, 1670-1676

Nonpatent document 22: Reid R. J., Hayes J. E., Post A., Stangoulis J. C. R., & Graham R. D. (2004) Plant Cell Environ. 27, 1405-1414

Nonpatent document 23: Huel, G.,Yazbeck, C., Burnel, D., Missy, P., & Kloppmann. W. (2004) Toxicol. Sci. 80,304-309

Nonpatent document 24: Ralston, N. V. C., & Hunt, C. D. (2000) FASEB J. 14, A538

Nonpatent document 25: Ricardo, A., Carrigan, M. A., Olcott, A. N., & Benner, S. A. (2004) Science 303, 196

Citation or identification of any document in this application is not an admission that such document is available as prior art to the present invention.

SUMMARY OF THE INVENTION

By introducing a gene that confers a boric acid tolerance to yeast into a plant, it has possibilities to generate plants having tolerance against excessive boron. It is thought that plant having boron tolerance can contribute to increase crop yields in places suffering from damages caused by excessive boron. Further, algae or bacteria wherein these genes have been introduced and boron tolerance has increased can be used to absorb boron contained in industrial water and to remove it, thus contributing to environmental cleanup. The present invention may provide a gene or protein conferring a boric acid tolerance to organisms, which has possibilities to generate plants having tolerance against excessive boron. Further, the present invention may provide a method for screening a gene conferring a boric acid tolerance effectively, by elucidating the toxicity mechanism of boric acid.

The present inventors devoted themselves to solve the above object and found 5 types of genes that can confer a boric acid tolerance to yeast, that is, AtPAB2, AtRBP47, AtRPS20B, AtMYB13 and AtMYB68, by expressing several genes of the higher plant *Arabidopsis thaliana* in yeast, which is an organism model of eukaryote. The present invention has been thus completed based on this knowledge. Further, the present inventors found that a key toxicity mechanism of boric acid exists in specific inhibition of splicing, and a gene related to enhancement of splicing efficiency also confers a boric acid tolerance, thus have completed the present invention.

That is, the present invention relates to (1) a DNA encoding a protein that may have an activity of conferring a boric acid tolerance and may consist of the amino acid sequence shown by SEQ ID NO: 2, 4, 6, 8, 10, 12, 14, 16, 18, 20, 22, 24, 26, 28 or 30; (2) a DNA encoding a protein that may consist of the amino acid sequence shown by SEQ ID NO: 2, 4, 6, 8, 10, 12, 14, 16, 18, 20, 22, 24, 26, 28 or 30 and has an activity of conferring a boric acid tolerance; (3) a gene DNA conferring a boric acid tolerance, which may consist of the base sequence shown by SEQ ID NO: 1, 3, 5, 7, 9, 11, 13, 15, 17, 19, 21, 23, 25, 27 or 29 or a complementary sequence thereof; (4) a DNA encoding a protein that consists of a base sequence wherein one or a few bases may be deleted, substituted or added in the base sequence shown by SEQ ID NO: 1, 3, 5, 7, 9, 11, 13, 15, 17, 19, 21, 23, 25, 27 or 29, and may have an activity of conferring a boric acid tolerance; (5) a DNA encoding a protein that may hybridize with the DNA according to "3" under stringent conditions and may have an activity of conferring a boric acid tolerance; (6) a protein that may have an activity of conferring a boric acid tolerance, which may consist of the amino acid sequence shown by SEQ ID NO: 2, 4, 6, 8, 10, 12, 14, 16, 18, 20, 22, 24, 26, 28 or 30; (7) a protein consisting of an amino sequence wherein one or a few amino acids may be deleted, substituted or added in the amino sequence shown by SEQ ID NO: 2, 4, 6, 8, 10, 12, 14, 16, 18, 20, 22, 24, 26, 28 or 30; and may have an activity of conferring a boric acid tolerance; (8) a recombinant vector including the DNA according to any one of "1" to "5", which may express a protein conferring a boric acid tolerance; (9) a transformant wherein the recombinant vector according to "8" is introduced, which may express a protein conferring a boric acid tolerance; (10) the transformant according to "9" wherein the transformant may be yeast; (11) the transformant according to "9" wherein the transformant may be a plant; (12) a method for screening a gene conferring a boric acid tolerance, which may comprise the steps of transforming a YNL275w-disrupted yeast which is deficient in and not expressing YNL275w gene by using a gene library, culturing the obtained transformed YNL275w-disrupted yeast in medium containing boric acid, and measuring/evaluating an activity of conferring a boric acid tolerance of the transformed YNL275w-disrupted yeast; (13) a method for screening a gene conferring a boric acid tolerance wherein an enhancement level of splicing efficiency may be measured/evaluated by targeting a specific inhibition of splicing by boric acid; (14) the method for screening a gene conferring a boric acid tolerance according to "13", which may comprise the steps of expressing a test substance in yeast cells, culturing the expressed test substance in the presence of boric acid, and measuring/evaluating an improvement level of a specific inhibition of splicing by boric acid in an intron-containing gene in yeast, as an enhancement level of splicing efficiency; (15) the method for screening a gene conferring a boric acid tolerance according to "14" wherein the gene containing intron in yeast may be a gene RPL7B in *Saccharomyces cerevisiae* genome; (16) use of the DNA according to any one of "1" to "5" as a gene conferring a boric acid tolerance; (17) use of the DNA according to any one of "1" to "5" for producing a plant or yeast conferred a boric acid tolerance; (18) use of the protein according to "6" or "7" as a protein having an activity of conferring a boric acid tolerance; and (19) use of the protein according to "6" or "7" for producing a plant or yeast conferred a boric acid tolerance.

By introducing a gene that confers a boric acid tolerance of the present invention into a plant, it has possibilities to generate plants having tolerance against excessive boron. It is thought that plant having boron tolerance can contribute to increase crop yields in places suffering from damages caused by excessive boron. Algae or bacteria wherein these genes have been introduced and boron tolerance has increased can be used to absorb boron contained in industrial water and to remove it, thus contributing to environmental cleanup.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawing, in which.

DETAILED DESCRIPTION

Figure 1:
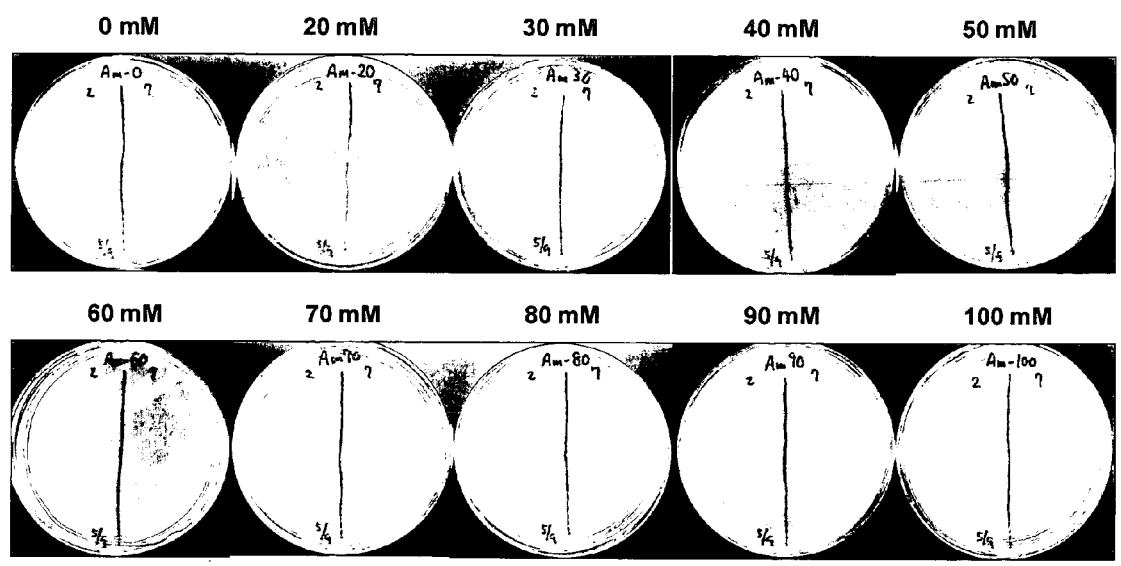
FIG. 1 is a set of pictures showing the results of performance test of boric acid tolerance using yeast strain 1169. Yeast strain 1169 was transformed with pYES2 "2" and pYES2-BORI "7". Each yeast was streaked in SD solid medium containing 0 to 100 mM boric acid. The results after culturing at 26.5° C. for 16 days are shown.

As for a gene DNA of the present invention, it is not especially limited as long as it is a gene conferring a boric acid tolerance consisting of the following: (A) a DNA encoding a protein that has an activity of conferring a boric acid tolerance and consists of the amino acid sequence shown by SEQ ID NO: 2, 4, 6, 8, 10, 12, 14, 16, 18, 20, 22, 24, 26, 28 or 30; (B) a DNA encoding a protein that consists of the amino acid sequence shown by SEQ ID NO: 2, 4, 6, 8, 10, 12, 14, 16, 18, 20, 22, 24, 26, 28 or 30 and has an activity of conferring a boric acid tolerance; (C) a gene DNA conferring a boric acid tolerance, which consists of the base sequence shown by SEQ ID NO: 1, 3, 5, 7, 9, 11, 13, 15, 17, 19, 21, 23, 25, 27 or 29 or a complementary sequence thereof; (D) a DNA encoding a protein that consists of a base sequence wherein one or a few bases are deleted, substituted or added in the base sequence shown by SEQ ID NO: 1, 3, 5, 7, 9, 11, 13, 15, 17, 19, 21, 23, 25, 27 or 29, and has an activity of conferring a boric acid tolerance; or (E) a DNA encoding a protein that hybridizes with a DNA conferring a boric acid tolerance which consists of the base sequence shown by SEQ ID NO: 1, 3, 5, 7, 9, 11, 13, 15, 17, 19, 21, 23, 25, 27 or 29 under stringent conditions and has an activity of conferring a boric acid tolerance.

Further, as for a protein of the present invention, it is not especially limited as long as the protein is the following: (A) a protein having an activity of conferring a boric acid tolerance, which consists of the amino acid sequence shown by SEQ ID NO: 2, 4, 6, 8, 10, 12, 14, 16, 18, 20, 22, 24, 26, 28 or 30; or (B) a protein Insisting of an amino sequence wherein one or a few amino acids are deleted, substituted or added in the amino sequence shown by SEQ ID NO: 2, 4, 6, 8, 10, 12, 14, 16, 18, 20, 22, 24, 26, 28 or 30; and having an activity of conferring a boric acid tolerance. Here, the term "a gene conferring a boric acid tolerance" relates to a gene that can confer a boric acid tolerance to a living organism, and the term "a protein conferring a boric acid tolerance" relates to a protein that can confer a boric acid tolerance to a living organism.

The above-mentioned phrase "a protein which has an activity of conferring a boric acid tolerance" relates to a protein having an activity that can confer tolerance against boric acid in a living organism such as yeast and plant, and the yeast and plant highly-expressing the protein can be grown even in the presence of boric acid in high concentration.

AtPAB2 gene as a gene conferring a boric acid tolerance consisting of the base sequence shown by SEQ ID NO: 1, AtPAB2 as a protein conferring a boric acid tolerance consisting of the amino acid sequence shown by SEQ ID NO: 2, AtRBP47c' gene as a gene conferring a boric acid tolerance consisting of the base sequence shown by SEQ ID NO: 3, AtRBP47c' as a protein conferring a boric acid tolerance consisting of the amino acid sequence shown by SEQ ID NO: 4, AtRPS20B gene as a gene conferring a boric acid tolerance consisting of the base sequence shown by SEQ ID NO: 5, AtRPS20B as a protein conferring a boric acid tolerance consisting of the amino acid sequence shown by SEQ ID NO: 6, AtMYB13 gene as a gene conferring a boric acid tolerance consisting of the base sequence shown by SEQ ID NO: 7, AtMYB13 as a protein conferring a boric acid tolerance consisting of the amino acid sequence shown by SEQ ID NO: 8, AtMYB68 gene as a gene conferring a boric acid tolerance consisting of the base sequence shown by SEQ ID NO: 9, AtMYB68 as a protein conferring a boric acid tolerance consisting of the amino acid sequence shown by SEQ ID NO: 10, AtRBP45a gene as a gene conferring a boric acid tolerance consisting of the base sequence shown by SEQ ID NO: 11, AtRBP45a as a protein conferring a boric acid tolerance consisting of the amino acid sequence shown by SEQ ID NO: 12, AtRBP45b gene as a gene conferring a boric acid tolerance consisting of the base sequence shown by SEQ ID NO: 13, AtRBP45b as a protein conferring a boric acid tolerance consisting of the amino acid sequence shown by SEQ ID NO: 14, AtRBP45c gene as a gene conferring a boric acid tolerance consisting of the base sequence shown by SEQ ID NO: 15, AtRBP45c as a protein conferring a boric acid tolerance consisting of the amino acid sequence shown by SEQ ID NO: 16, AtRBP45d gene as a gene conferring a boric acid tolerance consisting of the base sequence shown by SEQ ID NO: 17, AtRBP45d as a protein conferring a boric acid tolerance consisting of the amino acid sequence shown by SEQ ID NO: 18, AtRBP47a gene as a gene conferring a boric acid tolerance consisting of the base sequence shown by SEQ ID NO: 19, AtRBP47a as a protein conferring a boric acid tolerance consisting of the amino acid sequence shown by SEQ ID NO: 20, AtRBP47b gene as a gene conferring a boric acid tolerance consisting of the base sequence shown by SEQ ID NO: 21, AtRBP47b as a-protein conferring a boric acid tolerance consisting of the amino acid sequence shown by SEQ ID NO: 22, AtRBP47c gene as a gene conferring a boric acid tolerance consisting of the base sequence shown by SEQ ID NO: 23, AtRBP47c as a protein conferring a boric acid tolerance consisting of the amino acid sequence shown by SEQ ID NO: 24, AtUBP1a gene as a gene conferring a boric acid tolerance consisting of the base sequence shown by SEQ ID NO: 25, AtUBP1a as a protein conferring a boric acid tolerance consisting of the amino acid sequence shown by SEQ ID NO: 26, AtUBP1b gene as a gene conferring a boric acid tolerance consisting of the base sequence shown by SEQ ID NO: 27, AtUBP1b as a protein conferring a boric acid tolerance consisting of the amino acid sequence shown by SEQ ID NO: 28, AtUBP1c gene as a gene conferring a boric acid tolerance consisting of the base sequence shown by SEQ ID NO: 29, AtUBP1c as a protein conferring a boric acid tolerance consisting of the amino acid sequence shown by SEQ ID NO: 30, can be exemplified respectively.

The above-mentioned phrase "an amino sequence wherein one or a few amino acids are deleted, substituted or added" relates to an amino sequence wherein, for example, any number of 1 to 20, preferably 1 to 15, more preferably 1 to 10, furthermore preferably 1-5 amino acids are deleted, substituted or added. Further, the above-mentioned phrase "a base sequence wherein one or a few bases are deleted, substituted or added" relates to a base sequence wherein, for example, any number of 1 to 20, preferably 1 to 15, more preferably 1 to 10, furthermore preferably 1 to 5 bases are deleted, substituted or added.

For example, a DNA, which consists a base sequence wherein one or a few bases are deleted, substituted or added (mutated DNA), can be produced by any methods such as chemical synthesis, genetic engineering method and mutagenesis, which are known to those skilled in the art. Specifically, a mutated DNA can be obtained by introducing a mutation into a DNA that consists of the base sequence shown by SEQ ID NO: 1, 3, 5, 7 or 9, with the use of methods such as a method of allowing to contact and react an agent to be a mutagen, a method of irradiating ultraviolet and a genetic engineering method. Site-specific mutagenesis which one of the genetic engineering methods is a useful method that can introduce a specific mutant into a specific site, and can be performed according to methods described previously such as Molecular Cloning, A laboratory Manual, 2nd Ed., Cold Spring Harbor Laboratory, Cold Spring Harbor, NY, 1989 (hereinafter, abbreviated as "Molecular Cloning 2nd Ed."); Current Protocols in Molecular Biology, Supplement 1-38, John Wiley & Sons (1987-1997). By expressing this mutated DNA with the use of a suitable expression system, a protein encoded by an amino sequence wherein one or a few amino acids are deleted, substituted or added can be obtained.

The above-mentioned phrase "a base sequence which hybridizes under stringent conditions" relates to a base sequence obtained by using methods such as colony hybridization, plaque hybridization, and Southern blotting, with the use of nucleic acids such as DNA and RNA as a probe. Specifically, DNA that can be identified by hybridizing by using a filter-immobilized DNA derived from a colony or a plaque, or a fragment thereof, at 65° C. in the presence of 0.7-1.0 M NaCl; by washing the filter under the condition of 65° C. with the use of SSC solution of approximately 0.1-2.0-fold concentration (one-fold concentration of SSC solution is composed of 150 MM NaCl and 15 mM sodium citrate); can be exemplified. Hybridization can be performed according to the method described in Molecular Cloning 2nd Ed. and the like.

For example, as a DNA that can hybridize under stringent conditions, a DNA having above a certain level of homology with a base sequence of DNA used as a probe can be exemplified, and a DNA having, for example, 60% or more, preferably 70% or more, more preferably 80% or more, furthermore preferably 90% or more, especially preferably 95% or more, most preferably 98% or more of homology, can be exemplified.

Methods for obtaining and preparing genes of the present invention are not especially limited; and it can be prepared by isolating the desired genes through preparing a suitable probe or primer based on the base sequence information shown by SEQ ID NO: 1, 3, 5, 7 or 9, or the amino sequence information shown by SEQ ID NO: 2, 4, 6, 8 or 10 disclosed in the present specification, and screening a cDNA library wherein the presence of the genes are expected with the use of the above probe or primer; or by chemical synthesis according to ordinary methods.

Specifically, a gene of the present invention can be obtained by preparing a cDNA library from *Arabidopsis thaliana* from where the gene of the present invention was isolated, according to ordinary methods; and selecting the desired clone with the use of a specific and appropriate probe for the gene of the present invention. As the origin of the above cDNA, a variety of cells and tissues derived from the above plant can be exemplified; and further, isolation of all RNA from these cells or tissues, purification and isolation of mRNA, obtaining cDNA and the cloning thereof, and the like, can all be performed according to ordinary methods. As for a method for screening genes of the present invention from a cDNA library, for example, methods which are generally used by those skilled in the art such as methods described in Molecular Cloning 2nd Ed., and the like, can be exemplified.

Furthermore, a mutated gene or homologous gene of the present invention which consists of the base sequence shown by any one of the above (B) to (F) can be isolated, with the use of a DNA fragment having, the base sequence shown by SEQ ID NO: 1, 3, 5, 7 or 9, or part thereof, by screening a homolog of the DNA under appropriate conditions from other organisms and the like. Furthermore, it can be prepared by the above-mentioned methods for preparing the mutated DNA.

Methods for obtaining and preparing proteins of the present invention are not especially limited, and any one of the following proteins can be used: a natural occurring protein, a chemical synthetic protein, or a recombinant protein prepared by transgenesis. When obtaining a natural occurring protein, a protein of the present invention can be obtained from the cells or tissues expressing the protein, by combining appropriately the methods of isolation/purification of protein. When preparing a protein by chemical synthesis, for example, a protein of the present invention can be synthesized according to chemical synthesis such as Fmoc method (fluorenylmethyloxycarbonyl method) and tBoc method (t-butyloxycarbonyl method). Further, a protein of the present invention can be also synthesized with the use of various types of peptide synthesizer being marketed. When preparing a protein by transgenesis, a protein of the present invention can be prepared by introducing a DNA that consists of a base sequence encoding the protein into a preferable expression system. Among the above methods, preparation by transgenesis which manipulation is relatively easy and by which a large amount of preparation can be available, is preferable.

For example, when preparing a protein of the present invention by transgenesis, known methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography, and preferably high-performance liquid chromatography are used for collecting and purifying the protein from cell culture. Particularly, as for a column to use for affinity chromatography, for example, by using a column bound with antibodies such as monoclonal antibodies against a protein of the present invention; when a normal peptide tag is added to the above protein of the present invention, by using a column bound with certain materials that have an affinity for the peptide tag, purified products of these proteins can be obtained. Further, when a protein of the present invention is expressed on a cell membrane, purified preparations can be obtained by performing the above purification treatment after allowing to act a cell membrane catabolic enzyme.

In addition, a protein consisting of an amino acid sequence wherein one or a few amino acids are deleted, substituted or added in the amino acid sequence shown by SEQ ID NO: 2, 4, 6, 8, 10, 12, 14, 16, 18, 20, 22, 24, 26, 28 or 30, or a protein consists of the amino acid sequence having 60% or more of homology with the amino acid shown by SEQ ID NO: 2, 4, 6, 8, 10, 12, 14, 16, 18, 20, 22, 24, 26, 28 or 30 can be prepared or obtained conveniently by those skilled in the art according to the base sequence information shown by SEQ ID NO: 1, 3, 5, 7, 9, 11, 13, 15, 17, 19, 21, 23, 25, 27 or 29 which shows one of the examples of the base sequences encoding the amino acid sequence shown by SEQ ID NO: 2, 4, 6, 8, 10, 12, 14, 16, 18, 20, 22, 24, 26, 28 or 30 respectively. For example, a homolog of a DNA having the base sequence shown by SEQ ID NO: 1, 3, 5, 7, 9, 11, 13, 15, 17, 19, 21, 23, 25, 27 or 29, or part thereof can be isolated from organisms other than *Arabidopsis thaliana* by screening under appropriate conditions with the use of the DNA as a probe. A protein encoded by the homolog DNA can be prepared by integrating into an expression vector to express in an appropriate host after cloning a full length of the homolog DNA.

As for a recombinant vector of the present invention, it is not especially limited as long as it is a recombinant vector that contains the above gene of the present invention and can express a protein conferring a boric acid tolerance, and a recombinant vector of the present invention can be constructed by integrating the gene of the present invention appropriately into an expression vector. As for an expression vector, a vector that can self-replicate in host cells or can be integrated in chromosomes of host cells, is preferable; moreover, vectors which contain regulatory sequences such as promoter, enhancer and terminator at a position where a gene of the present invention can be expressed, can be used preferably. As for an expression vector, an expression vector for yeast, an expression vector for plant cells, an expression vector for bacteria, an expression vector for animal cells and the like can be used; however, a recombinant vector using an expression vector for yeast or expression vector for plant cells is preferable.

As for an expression vector for yeast, pYES2 (Invitrogen), YEp13 (ATCC37115), YEp24 (ATCC37051), Ycp50 (ATCC37419), pHS19 and pHS15 can be exemplified. As for a promoter for yeast, PHO5 promoter, PGK promoter, GAP promoter, ADH promoter, GAL1 promoter, GAL10 promoter, heat shock protein promoter, MFα1 promoter and CUP1 promoter can be specifically exemplified.

As for an expression vector for plant cells, plasmids such as Ti plasmid (Tumor inducing plasmid), pSPORT1, pT7Blue-T vector, pIG121-Hm [Plant Cell Report, 15, 809-814(1995)], pBI121 [EMBO J. 6, 3901-3907(1987)], or plant viral vectors such as tobacco mosaic virus, cauliflower mosaic virus and geminivirus can be exemplified. As for a promoter for plant cells, cauliflower mosaic virus 35S promoter [Mol.Gen. Genet (1990) 220, 389-392] and ribulose bisphosphate carboxylase small subunit promoter can be exemplified, and as for a terminator, nopaline synthase gene terminator can be exemplified.

Further, as for a transformant of the present invention, it is not especially limited as long as it is a transformant wherein the above recombinant vector of the present invention is introduced and which expresses a protein conferring a boric acid tolerance. Transgenic yeasts, transgenic plants (cells, tissues, individuals), transgenic bacteria, transgenic animals (cells, tissues, individuals), can be exemplified, while transgenic yeasts and transgenic plants (cells, tissues, individuals) are preferable.

As for a host yeast to use for producing a transgenic yeast, *Saccharomyces cerevisiae, Schizosaccharomyces prombe, Kluyveromyces lactis, Trichosporon pullulans* and *Schwanniomyces alluvius* can be exemplified. As for a method for introducing a recombinant vector to host yeast, for example, electroporation, spheroplast method and lithium acetate method can be exemplified.

As for a host plant (cell, tissue, individual) to use for producing a transgenic plant (cell, tissue, individual), species is not especially limited, and it can be appropriately selected from plants such as flowers and ornamental plants, fruit plants, vegetables, root crops, cereals, foliage plants and trees including fruit trees, for example, plants belonging to Solanaceae, Poaceae, Brassicaceae, Asteraceae, Pedaliaceae, Oleaceae, Myrtaceae, Rosaceae, Leguminosae, Palmae or rubiaceae, and cultured cells and tissues thereof (seed, callus and the like) To produce a transgenic plant, a method for introducing a gene DNA of the present invention into genomic DNA within plant cells, by introducing the above recombinant vector into plant cells with the use of the recombinant vector of the present invention containing a gene of the present invention can be used. Transformation of a plant can be performed by appropriately using known methods such as leaf disk cocultivation method, electroporation, *Agrobacterium* method and particle gun method, according to species of the plant. Other methods for producing transgenic plant, including a method by directly incorporating a recombinant vector of the present invention into a receptor cell can be also used, by physically or chemically enhancing the permeability of plant cells.

As for a method for screening a gene conferring a boric acid tolerance of the present invention is not especially limited as long as it is a method for measuring/evaluating an activity of conferring a boric acid tolerance of the transformed YNL275w-disrupted yeast by transforming a YNL275w-disrupted yeast which is deficient in and not expressing YNL275w gene with the use of a gene library such as a variety of plants or yeasts, and by culturing the obtained transformed YNL275w-disrupted yeast in medium containing boric acid. As for a measurement/evaluation of an activity of conferring a boric acid tolerance, a measurement/evaluation of a level of growth/proliferation of transgenic yeast in culture medium containing boric acid can be exemplified. Further, as for a YNL275w-disrupted strain, *Saccharomyces cerevisiae* strain 1169 (Winzeler, E. A.; Shoemaker, D. D.; Astromoff, A.; Liang, H.; Anderson, K.; Andre, B.; Bangham, R.; Benito, R.; Boeke, J. D.; Bussey, H., Chu, A. M.; Connelly, C.; Davis, K.; Dietrich, F.; Dow, S. W.; El Bakkoury, M.; Foury, F.; Friend, S. H.; Gentalen, E.; Giaever, G.; Hegemann, J. H.; Jones, T.; Laub, M.; Liao, H.; Liebundguth, N.; Lockhart, D. J.; Lucau-Danila, A.; Lussier, M.; M'Rabet, N.; Menard, P.; Mittmann, M.; Pai, C.; Rebischung, C.; Revuelta, J. L.; Riles, L.; Roberts, C. J.; Ross-MacDonald, P.; Scherens, B.; Snyder, M.; Sookhai-Mahadeo, S.; Storms, R. K.; Veronneau, S.; Voet, M.; Volckaert, G.; Ward, T. R.; Wysocki, R.; Yen, G. S.; Yu, K. X.; Zimmermann, K.; Philippsen, P.; Johnston, M.; Davis, R. W. (1999) Functional characterization of the *Saccharomyces cerevisiae* genome by gene deletion and parallel analysis. Science 285: 901-906) can be preferably exemplified. As for yeast to use for screening, it is not limited to YNL275w-disrupted strains, and wild types can be used.

Further, as for a screening method of a gene conferring a boric acid tolerance of the present invention, a method for measuring/evaluating an enhancement level of splicing efficiency can be exemplified, for example, a method for measuring/evaluating an improvement level of a specific inhibition of splicing by boric acid in an intron-containing gene in yeast by expressing a test substance in yeast cells and culturing the expressed test substance in the presence of boric acid, as an enhancement level of splicing efficiency, can be exemplified. As for an intron-containing gene in yeast, specifically RPL7B gene (SEQ ID NO: 33) which is a gene encoding large subunit protein of essential ribosome in *Saccharomyces cerevisiae* genome, can be exemplified. The improvement level of specific inhibition of splicing by boric acid can be measured, for example, by RT-PCR, and at that time, AtRBP47c' gene, which is a gene conferring a boric acid tolerance is preferably used as a positive control.

In the present invention, use of (a method for) using the above DNA of the present invention as a gene conferring a boric acid tolerance, use of (a method for) using the above DNA of the present invention for producing plants or yeast conferred a boric acid tolerance, use of (a method for) using the above protein of the present invention as a protein having an activity of conferring a boric acid tolerance, and use of (a method for) using the above protein of the present invention for producing plants or yeast conferred a boric acid tolerance are included. Therefore, using the above gene conferring a boric acid tolerance and the above protein having an activity of conferring a boric acid tolerance (protein conferring a boric acid tolerance) for producing plants or yeast conferred a boric acid tolerance are included in the embodiments of the present invention.

The invention will now be further described by way of the following non-limiting examples which further illustrate the invention, and are not intended, nor should they be interpreted to, limit the scope of the invention.

EXAMPLES

Example 1

1.1. Test Yeasts and Plasmids

As for yeasts, *Saccharomyces cerevisiae* strain 1169 (purchased from Research Genetics) and *Saccharomyces cerevisiae* strain BY4741 (purchased from Research Genetics) are used. Genotypes for strain 1169 are MATa, his3Δ1, leu2Δ0, met15Δ0, ura3Δ0, YNL275w, kanMX4; and MATa, his3Δ1, leu2Δ0, met15Δ0, ura3Δ0 for strain BY4741 respectively. As for plasmids, pYES2 (purchased from Invitrogen Genetics) and pFLM61 (provided from Dr. Nicolaus von Wiren in Hohenheim University, Germany; Minet M., Dufour M. -E., and Lacroute F. (1992) Complementation of *Saccharomyces cerevisiae* auxotrophic mutants by *Arabidopsis thaliana* cDNAs. Plant J. 2, 417-422) were used. pFL61 was used to produce an *Arabidopsis thaliana* expression library. Boric acid tolerance test on yeast-strain 1169

The performance of boric acid tolerance in the used yeast strain 1169 was evaluated. A single colony of yeast strain 1169 which was transformed with pYES2 and pYES2-BOR1 (to which inserted CDS of BOR1, a boron tolerance gene of *Arabidopsis thaliana* downstream of GAL1 promoter of pYES2 vector) was picked by a platinum loop, and shaking cultured to an $OD_{600}$ of around 1.0 in SD liquid medium. The culture solution was respectively streaked in SD solid medium containing 0, 20, 30, 40, 50, 60, 70, 80, 90 or 100 mM boric acid, and cultured at 26.5° C. for 16 days. It was then evaluated whether or not the yeast can form colony in each medium.

1.2. Screening of Genes Conferring Boric Acid Tolerance

Yeast strain 1169 was transformed with lithium acetate method with the use of *Arabidopsis thaliana* expression library (provided from Dr. Nicolaus von Wiren in Hohenheim University, Germany; Schaaf G., Catoni E., Fits M., Schwacke R., Schneider A., von Wiren N., and Frommer W.B. (2002) A putative role for the vacuoler calcium/manganese proton antiporter AtCAX2 in heavy metal detoxification. Plant Biol. 4; 612-618). The transgenic yeast was streaked in SD medium added 80 mM boric acid (6.7 g/l yeast nitrogen base without amino acids, 5 g/l ammonium sulfate, 20 g/l glucose, 2 g/l histidine, 2 g/l methionine, 3 g/l leucine, 20 g/l agar, pH 5.5) and cultured at 26.5° C. After 10 to 14 days, plasmids were collected from the yeast that formed a colony.

The collected plasmids were introduced into yeast again and the repeatability of the performance of boric acid tolerance was identified.

1.3. Boric Acid Tolerance Tests

Spot assays and tests in liquid culture were performed. Spot assays were performed by the following procedures. Each of the yeast was shaking cultured to an $OD_{600}$ of 0.5-1.0 at 30° C. in SD liquid medium. Each yeast culture was diluted until the values of $OD_{600}$ are equal in SD medium. 1/5, 1/25, 1/125 or 1/625 diluted diluent which values of $OD_{600}$ are equal was prepared for each yeast culture medium. Each diluent was spotted with 5 µl at a time by pipetman (Gilson) in SD solid medium with boric acid, and in SD solid medium without boric acid as a control. It was also spotted from left to right to lower the concentration for the same. The plate spotted yeast was cultured at 30° C. for around 10 days and growth states of the yeast were observed.

Test in liquid culture was performed as follows. Each yeast was shaking cultured to an $OD_{600}$ of around 1.0 at 30° C. in SD medium. Each culture medium was subcultured in SD solid medium with boric acid, and in SD solid medium without boric acid as a control, to an $OD_{600}$ of 0.1, and shaking cultured at 30° C., then the values of $OD_{600}$ were measured every 24 hours.

1.4. Sequences of Genes Conferring Boric Acid Tolerance

Analysis of the base sequences of 6 cDNA clones obtained by screening was performed as follows. The base sequences were analyzed by performing sequence reaction using fluorescent dye-terminator terminator, with the use of ABI 310 genetic analyzer. A gene encoding the base sequences was identified by BLAST search of TAIR (see the website for The Arabidopsis Information Resource) from the obtained base sequences.

1.5. Screening Results of Genes Conferring Boric Acid Tolerance

First, the performance of boric acid tolerance in yeast strain 1169 used in the present experiments was evaluated. The yeast 1169 was transformed with pYES2 and pYES2-BOR1. pYES2 and pYES2-BOR1 were used for the transformation, because these vectors retain URA3 that is the same one as vector pFL61, which is used in the Arabidopsis thaliana expression library that is used for the following screening, as a selection marker. Further, in SD medium, as the expression of BOR1 gene of pYES-BOR1 is not induced, the same level of boric acid tolerance as in transformant of pYES2 should be induced. The yeasts transformed with pYES2 and pYES2-BOR1 were named "2" and "7", respectively. "2" and "7" were shaking cultured in SD liquid medium, and streaked in SD solid medium containing 0, 20, 30, 40, 50, 60, 70, 80, 90 or 100 mM boric acid. As a result, it was revealed that the transformant by either vector could not also be grown in SD medium containing 80 mM or more of boric acid (FIG. 1).

Figure 2:
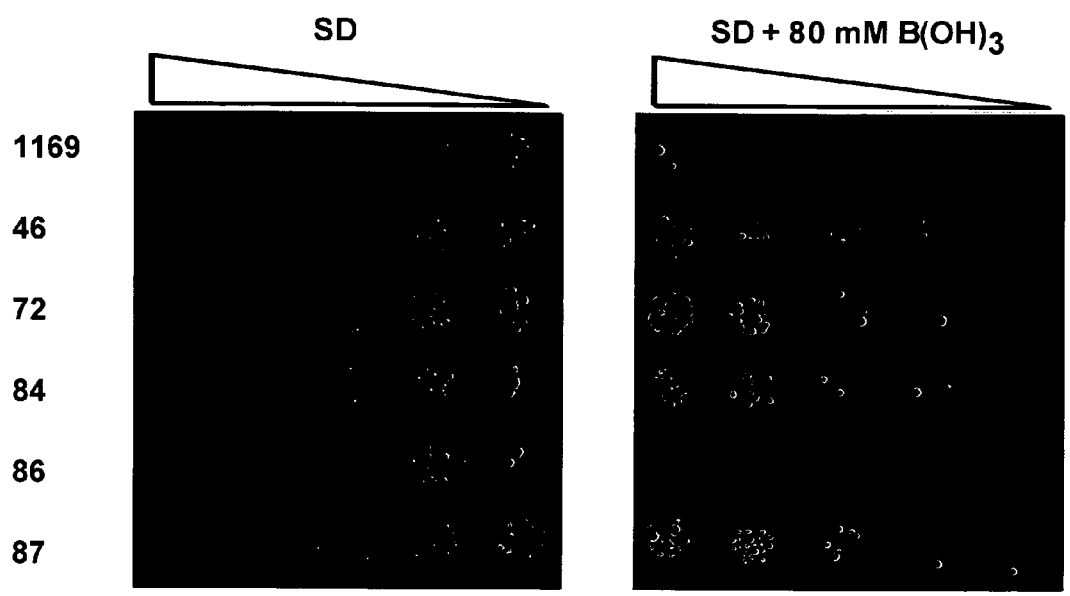
FIG. 2 is a set of pictures showing the growth results of yeast strain 1169 in excessive boric acid medium. Yeast strain 1169 was transformed with 46, 72, 84, 86 and 87. Each yeast was spotted in SD medium containing 80 mM boric acid after the liquid culture. The spots were diluted by 1/5 at a time from left to right. The results after culturing at 26.5° C. for 9 days are shown.
Figure 3:
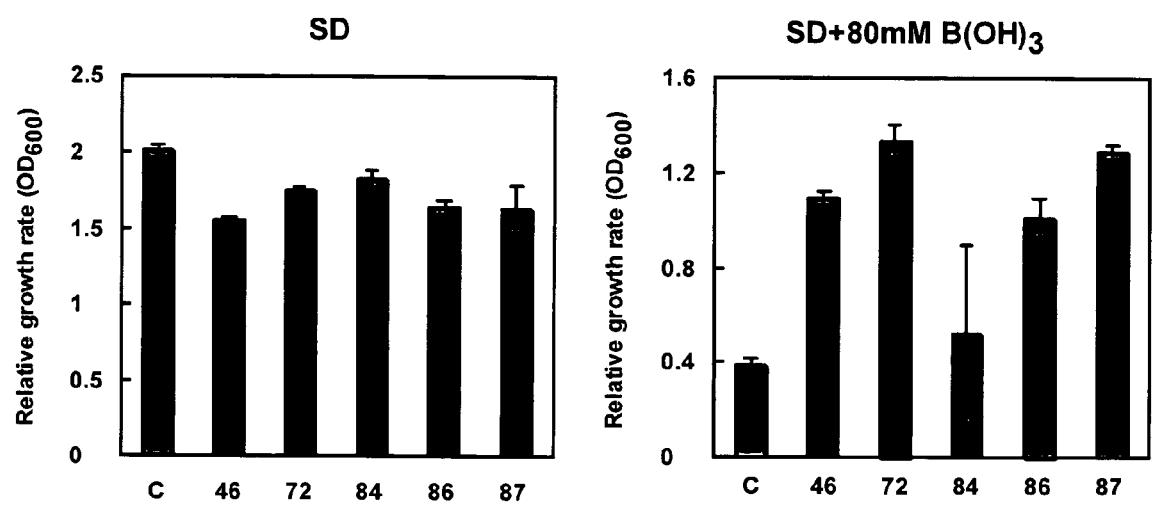
FIG. 3 is a set of graphs showing the results of boric acid tolerance test of yeast strain 1169 in liquid medium. Yeast strain 1169 was transformed with 46, 72, 84, 86 and 87. Each yeast was subcultured to an $OD_{600}$ of 0.1 in SD medium containing 80 mM boric acid after the liquid culture. The values of $OD_{600}$ were measured after culturing at 30° C. for 4 days. The experiments of the test were performed in triplicate. The mean of the measurements and the standard deviation are shown using graph.
Figure 4:
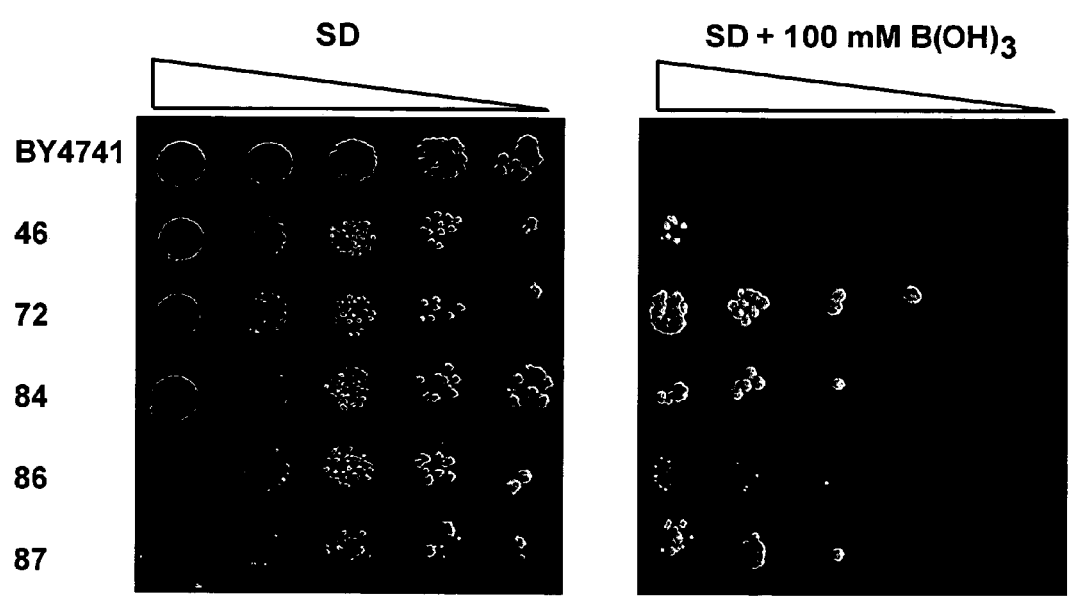
FIG. 4 is a set of pictures showing the growth results of yeast strain BY4741 in excessive boric acid medium. Yeast strain BY4741 was transformed with 46, 72, 84, 86 and 87. Each yeast was spotted on SD medium containing 100 mM boric acid after the liquid culture. The spots were diluted by 1/5 at a time from left to right. The results after culturing at 26.5° C. for 10 days are shown.
Figure 5:
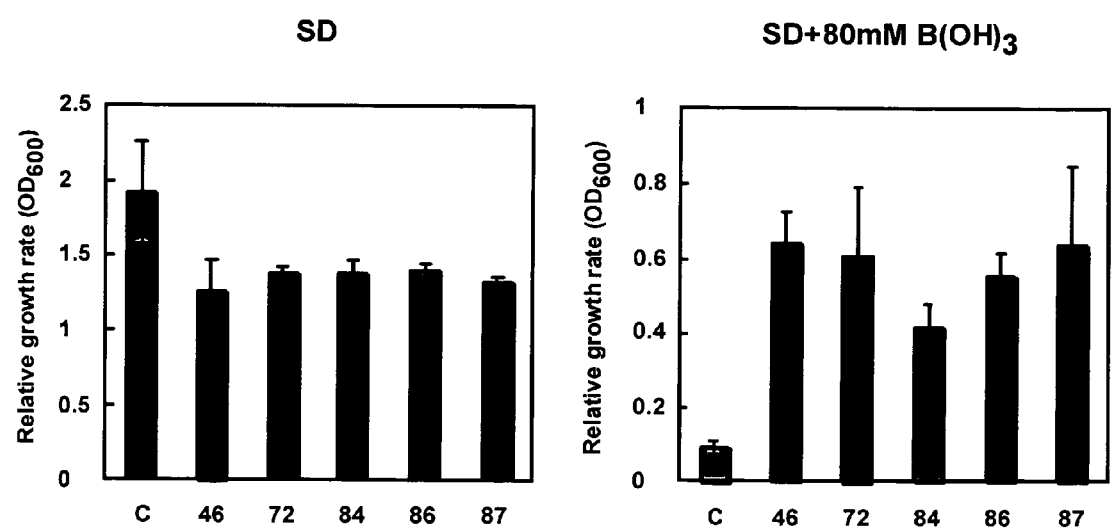
FIG. 5 is a set of graphs showing the results of boric acid tolerance test of yeast strain BY4741 in liquid medium. Yeast strain BY4741 was transformed with 46, 72, 84, 86 and 87. Each yeast was subcultured to an $OD_{600}$ of 0.1 in SD medium containing 80 mM boric acid after the liquid culture. The values of $OD_{600}$ were measured after culturing at 30° C. for 4 days. The experiments of the test were performed 3 times. The mean of the measurements and the standard deviation are shown using graphs.

To isolate ones inferring a boric acid tolerance, Arabidopsis thaliana genes that can grow the yeast in SD medium containing 80 mM boric acid by expressing the genes in yeast strain 1169 were searched in the present experiment. Therefore, around 1.2 million yeasts transformed in Arabidopsis thaliana expression library were streaked in SD medium containing 80 mM boric acid. As a result, 6 transgenic yeasts: 46, 66, 72, 84, 86 and 87 that induce tolerance against 80 mM boric acid were obtained. The performances of boric acid tolerance in transgenic yeasts: 46, 72, 84, 86 and 87 by spot assays are shown in FIG. 2 (Since 66 encodes the same gene as 46 does, it is shown in the following, only the result of 46 is shown) . Yeast strain 1169 can hardly form colony in SD medium containing 80 mM boric acid, as it is shown in the upper half of FIG. 2. On the other hand, any of these transgenic yeasts could form more colonies compared to 1169 strain. Next, test in liquid culture was performed. In the liquid culture, 46, 72, 86 and 87 showed around 3-fold growth potential compared to strain 1169 in boric acid medium, as shown in FIG. 3. However, 84 had variable growth rates and no significant difference was observed compared to strain 1169 in boric acid tolerance. Further, these genes could confer a boric acid tolerance when they were introduced into yeast strain BY4741 as well as when they were introduced into 1169 strains. The results from spot assays are shown in FIG. 4, and the results from liquid culture are shown in FIG. 5. When they were introduced into strains BY4741, in all of the transformed yeasts, significant differences were also observed in boric acid tolerance in the liquid culture (FIG. 5).

1.6. Sequences of Genes Conferring Boric Acid Tolerance 6 base sequences of the cDNA clones obtained from screening were determined, and genes encoding them were identified by BLAST searches. As a result, it was revealed that 46 and 66, 72, 84, 86, and 87 matched AtPAB2, AtMYB68, AtMYB13, AtRPS20B, and AtRBP47, respectively. The respective sequences of the genes are shown in the following sequence listing. AtPAB2, AtMYB13 and AtMYB68, AtRPS20, and AtRBP47 are genes encoding polyA-binding protein, Myb-like transcription factor, ribosomal protein, and RNA-binding protein, respectively.

Example 2

2.1. Yeast Strains and Screening

Saccharomyces cerevisiae strain BY4741 (MATa his3D1 leu2D0 met15D0 ura3D0), Y01169 (MATa his3D1 leu2D0 met15D0 ura3D0 YNL275W::kanMX4), Y04443 (MATa his3D1 leu2D0 met15D0 ura3D0 YGL076C::kanMX4), and Y01094 (MATa his3D1 leu2D0 met15D0 ura3D0 YPL198W::kanMX4), were used in this study. Strains: Y01169, Y04443, and Y01094 were constructed from BY4741 by insertional mutagenesis (Winzeler et al., 1999) and obtained from EUROSCARF.

Yeast competent cells were transformed with an Arabidopsis thaliana cDNA library cloned in the expression plasmid pFL61(Minet et al., 1992) by using the lithium acetate method (Gietz and Schiestl, 1995). The strain Y01169 was used as a host because it lacks YNL275W (hereinafter, referred to as BOR1), an efflux B transporter, and sensitive to boric acid compared with the corresponding wild type strain (data not shown). Transformants were screened on SD solid medium (Sherman, 1991) containing 80 mM boric acid at 26.5° C. SD medium contained 2% glucose, 0.67% yeast nitrogen base without amino acids, 0.05% ammonium sulfate, and the amino acids (20 mg/L His, 30 mg/L Leu, and 20 mg/L Met), which are required for the growth of the mutant, and the pH was adjusted to 5.5 with Tris. Agar (2% w/v) was added for making the solid medium. Colony formation of the nontransformed Y01169 (Δbor1) cells was completely suppressed by addition of 80 mM boric acid. Among the transformed cells, those that formed colonies on media containing 80 mM boric acid after two-week incubation at 26.5° C. were selected and their tolerance were confirmed by testing their growth in the presence of 80 mM boric acid. To confirm that the phenotype was conferred by the plasmids, plasmids were isolated from the positive isolates and re-transformed into the yeast strain Y01169. Tolerant isolates were subjected to fluoro-orotic acid-induced plasmid loss (Boeke, J. D., LaCroute, F., & Fink, G. R. (1984) Mol. Gen. Genet. 197, 345-346) to select only those clones showing plasmid-dependent boric acid tolerance.

2.2. Construction of Plasmids

ORF sequences of AtRBP47c"-related genes and RPL7B (see SEQ ID NO: 34) were amplified by PCR using the primer sets listed in Table 1. The amplified products were sub-cloned into pGEM-T easy vector (Promega). These plasmids were treated with NotI, and the resultant ORF fragments of AtRBP45a, AtRBP47b, AtRBP47c, AtRBP47c' and AtUBP1 were cloned into the NotI site of the pFL61 expression vector (Minet et al., 1992), and the ORF fragments of RPL7B were cloned into the NotI site of the pDR195 expression vector (Rentsch et al., 1995). pFL61 And pDR195 carry PGK and PMA1 promoters for expression, respectively.

TABLE 1

(SEQ ID NOS 35-48, respectively, in order of appearance)

| Gene | Primer sequences |
|---|---|
| AtRBP45a | 5'-AAAAAGCAGGCTTAATGCAGCAACCACCGTCAAACGC C-3' |
| | 5'-AGAAAGCTGGGTTTCACTGACGTTGCTGCTGATAGT T-3' |
| AtRBP47a | 5'-AAAAAGCAGGCTTAATGCAGACACCAAACAACAACGG T-3' |
| | 5'-AGAAAGCTGGGTTTCAAGAAGCTCCCGGGACTGCAG C-3' |
| AtRBP47b | 5'-AAAAAGCAGGCTTAATGCAGACAACCAACGGCTCAGA T-3' |
| | 5'-AGAAAGCTGGGTTTCAATTCTCCCCATGATAGTTGT T-3' |
| AtRBP47c | 5'-AAAAAGCAGGCTTAATGGCAGACGTCAAGATTCAATC C-3' |
| | 5'-AGAAAGCTGGGTTTCAGCTAACTTGTTGCTGATGAC C-3' |
| AtRBP47c' | 5'-AAAAAGCAGGCTTAATGGCAGACGTCAAGGTTCAATC C-3' |
| | 5'-AGAAAGCTGGGTTTCAGCTAACTTGTTGCTGATGAC C-3' |
| AtUBP1a | 5'-AAAAAGCAGGCTTAATGCAGAATCAAAGGCTTATTAA G-3' |
| | 5'-AGAAAGCTGGGTTTTACTGATAGTACATGAGCTGCT G-3' |
| RPL7B | 5'-AAAAAGCAGGCTTAATGTCCACTGAAAAAATCTT-3' |
| | 5'-AGAAAGCTGGGTTTTAGTTCATAGCCTTAACCA-3' |

2.3. Boric Acid Tolerance Assays

For boric acid tolerance assay of AtRBP47c"-related family genes, the expression plasmids were introduced into the *Saccharomyces cerevisiae* strain BY4741. As controls, empty vectors without insert were also introduced into BY4741. The transformants were grown to stationary phase in the SD liquid medium, and then cell densities of the cultures were adjusted to $OD_{600}$=1.0. These cell density-adjusted cultures were diluted to 1/5, 1/25, 1/125, and 1/625 with the SD liquid medium and 10 μL of diluted cultures were dropped on the SD solid medium with or without 80 mM boric acid and incubated at 30° C. for 7 days.

For analysis in liquid culture, the transformants were grown to stationary phase in the SD liquid medium, and then diluted in the SD liquid medium with or without 80 mM boric acid to adjust the value of $OD_{600}$ to 0.1 for the performance test of high concentration boric acid tolerance.

For analysis of boric acid tolerance of Δrpl7a (Y04443) and Δrpl7b (Y01094) mutants, SD medium containing 2% glucose, 0.67% yeast nitrogen base without amino acids, and 0.05% ammonium sulfate was used, adjusting to pH 5.5 with Tris, and the required amino acids (20 mg/L His, 30 mg/L Leu, 20 mg/L Met, and 20 mg/L Ura) were added. The mutants were obtained from EUROSCARF. To further examine the role of RPL7B in boric acid tolerance, RPL7B was over-expressed in the yeast strain Y04443. Boric acid tolerance assays were carried out as described above.

2.4 Detection of Unspliced Transcripts by RT-PCR

Yeast cells were grown to exponential phase ($OD_{600}$=0.5-1.0) in SD liquid medium, and then boric acid was added to be 80 mM at final concentration. After 24h incubation at 30° C., one-ml of samples were taken, and the cells were collected by centrifugation, frozen in liquid nitrogen, and stored at −80° C. until use.

Total RNA was extracted from the yeast cells by using an RNeasy Mini Kit (Qiagen), and 1 μg of total RNA was reverse-transcribed by using MuLV reverse-transcriptase (Applied Biosystems) and oligo $(dT)_{16}$ primer. One-fifteenth of the RT products was subjected to PCR with the following cycle: 40-50 times at 94° C. for 30 sec, 45° C. for 30 sec, and 72° C. for 1 min. PCR was carried out with a Smart Cycler (Cepheid) using a DNA polymerase, Ex taq (Takara). Primer sets used in this analysis are listed in Table 2, which is published as expanded information on the PNAS web site. Amplified transcripts were separated on 2% agarose gel and detected after staining with Etd bromide.

TABLE 2

(SEQ ID NOS 49-134, respectively, in order of appearance)

| Gene | Primer sequences | |
|---|---|---|
| SNR17A | 5'-AATCTGTGTCGACGTACTTC-3' | (Forward) |
| | 5'-AGAAGTACATAGGATGGGTC-3' | (Reverse) |
| SNR17B | 5'-AAAAATTGTCGACGTACTTC-3' | (Forward) |
| | 5'-AAAGGAAGTTATCACAATTG-3' | (Reverse) |
| YBR230C | 5'-CCAGCATCTATGTCTGCAAC-3' | (Forward) |
| | 5'-CGTATCTGGAGTAGTATTTC-3' | (Reverse) |
| VMA10 | 5'-GCAAGGTATACAAAGCAGAA-3' | (Forward) |
| | 5'-TCATCCTTTTTCTTCTCTGC-3' | (Reverse) |
| SEC27 | 5'-GACACGATGAAGTTGGATAT-3' | (Forward) |
| | 5'-TGACTGTCAAATCATCACTG-3' | (Reverse) |
| YNL050C | 5'-CAGTATAAAAATGTCTGAAT-3' | (Forward) |
| | 5'-TGGTTGATTATTTCTTCTTC-3' | (Reverse) |
| RPL7B | 5'-ATCAACGTCATAATGTCCAC-3' | (Forward) |
| | 5'-TACCAGAGTTGATTCTTGTC-3' | (Reverse) |
| MUD1 | 5'-ACCTAAAGAAACCATGTCAG-3' | (Forward) |
| | 5'-TATCAAGGTTGTACGTTTCG-3' | (Reverse) |
| SNC1 | 5'-ATGTACAGTCTAAGTCAAGG-3' | (Forward) |
| | 5'-GACTAAAGTGAACAGCAATG-3' | (Reverse) |
| POP8 | 5'-GAGAATGGCAATATTTCAAG-3' | (Forward) |
| | 5'-TGTTCTTCTTCTTCCATTAC-3' | (Reverse) |
| ARP2 | 5'-TGGACCCACATAATCCAATT-3' | (Forward) |
| | 5'-TTTCGAACATTACCTCACAC-3' | (Reverse) |
| CNB1 | 5'-GTGGATGGTCTTTTAGAAGA-3' | (Forward) |
| | 5'-AACTCCTCGAAACTTAAACG-3' | (Reverse) |

TABLE 2-continued (SEQ ID NOS 49-134, respectively, in order of appearance)

| Gene | Primer sequences | |
|------|------------------|---|
| RPS22B | 5'-TATTGAGACCTTCTTCCAAG-3' | (Forward) |
|  | 5'-AAGATTTTACCGGAAACGTG-3' | (Reverse) |
| YML025C | 5'-GACGATAAAAAGAAATTTGGTG-3' | (Forward) |
|  | 5'-CTCAAAGCGTTGTTGAAAG-3' | (Reverse) |
| TUB3 | 5'-GAGAGAGGTCATTAGTATTA-3' | (Forward) |
|  | 5'-TTTTCTAATAACAGGGAACC-3' | (Reverse) |
| STO1 | 5'-GTTTAATAGAAAAAGAAGAGGAG-3' | (Forward) |
|  | 5'-TAGTTCATCAACTAAAAACATGG-3' | (Reverse) |
| RPS16A | 5'-AGCTGTCCCAAGTGTTCAA-3' | (Forward) |
|  | 5'-ACCCTTACCACCGAATTTC-3' | (Reverse) |
| SAR1 | 5'-GTTGGGATATTTTGGTTGG-3' | (Forward) |
|  | 5'-AAAGGAACGTCCTTCAATTC-3' | (Reverse) |
| PM140 | 5'-AACAAGCTGTTCAGGTTAGA-3' | (Forward) |
|  | 5'-GGTTTGTGATTATCATCAGG-3' | (Reverse) |
| RPL7A | 5'-AATTAAAGATCACAATGGCCG-3' | (Forward) |
|  | 5'-CTTGGTAACTTTGACGAATG-3' | (Reverse) |
| YBL091C-A | 5'-CAGAAAAGCTGGTGTTCAAG-3' | (Forward) |
|  | 5'-TGATTCTGCATCGTGGTTTC-3' | (Reverse) |
| RPL19A | 5'-TTGATTAAGAACTCCAAAGC-3' | (Forward) |
|  | 5'-TCTTCTCAAGACACGTAATC-3' | (Reverse) |
| PCH2 | 5'-AGATGAGGTTGAAGCAATAG-3' | (Forward) |
|  | 5'-CAAGGGCAATTTCCTTATTG-3' | (Reverse) |
| RPS9B | 5'-TAAGACTAAGCAACAATGCC-3' | (Forward) |
|  | 5'-AAACCCAACTTGTAGACTTG-3' | (Reverse) |
| YBR230C | 5'-GCATCTCATAATATGTCTGC-3' | (Forward) |
|  | 5'-TTGTTGCTAAGACTGTAGAG-3' | (Reverse) |
| YDR381C-A | 5'-CAAATCCATTTCAAAATATAGG-3' | (Forward) |
|  | 5'-CTCCTCCTATCTAAAAAACC-3' | (Reverse) |
| YRA1 | 5'-AAGAAGAGTTGGTAAGCAAG-3' | (Forward) |
|  | 5'-CACCGTTTTTGAATGTGATG-3' | (Reverse) |
| UBC8 | 5'-AGCGTAATACGAAAGATGAG-3' | (Forward) |
|  | 5'-AGCTTCGTTATTCAAGGGAT-3' | (Reverse) |
| MND1 | 5'-GTATCATAAACATTCAACAATG-3' | (Forward) |
|  | 5'-CGGATCTGTTGTTTATTCTC-3' | (Reverse) |
| MER3 | 5'-AAACAAAGTTTGATCGCCTG-3' | (Forward) |
|  | 5'-TCGTGCTCAAACATTTCTTC-3' | (Reverse) |
| ERV1 | 5'-AAAATGACGGATAATCCACC-3' | (Forward) |
|  | 5'-TTCAAAGTCTTTAGCACACC-3' | (Reverse) |
| SRB2 | 5'-CAATCCATCATGGGAAAATC-3' | (Forward) |
|  | 5'-CTTGGACGACAAAATAGTGT-3' | (Reverse) |
| MOB1 | 5'-AGGACTTCAATTTCCATGTC-3' | (Forward) |
|  | 5'-AGTGTCATCTCCACAATTTG-3' | (Reverse) |
| RPS21A | 5'-GAAAACGATAAGGGCCAATT-3' | (Forward) |
|  | 5'-CGTTCTTTAACAAACCATCG-3' | (Reverse) |
| NYV1 | 5'-TACCAAATGAAACGCTTTAATG-3' | (Forward) |
|  | 5'-TCTTCATGGAAAGAGTCTAG-3' | (Reverse) |
| YLR211C | 5'-ATGGAATGAGTACTTTAGCG-3' | (Forward) |
|  | 5'-CTTCATTTCCGAGTTTTTGG-3' | (Reverse) |
| TAD3 | 5'-AATAGAAAATCGGCTTCTGC-3' | (Forward) |
|  | 5'-TATTTGATCATTGGGGTTGC-3' | (Reverse) |

TABLE 2-continued (SEQ ID NOS 49-134, respectively, in order of appearance)

| Gene | Primer sequences | |
|------|------------------|---|
| ERV41 | 5'-GATTGAAGACATTTGATGCG-3' | (Forward) |
|  | 5'-TCGCCACTAACTCTATTTAC-3' | (Reverse) |
| SPO1 | 5'-ACCATTTCAGGTACAATGTC-3' | (Forward) |
|  | 5'-CTTCGGAAATATCGAATTCC-3' | (Reverse) |
| YOL048C | 5'-CTGAAACGATACCAACAATG-3' | (Forward) |
|  | 5'-TTTGTGGTTTAGGCAATACC-3' | (Reverse) |
| RPS9A | 5'-ATACAAAAGTATACAACATGCC-3' | (Forward) |
|  | 5'-TTTCCAAGAAATCTTCGACC-3' | (Reverse) |
| CIN2 | 5'-CTTTACTGCGAAGATAAAGG-3' | (Forward) |
|  | 5'-GCCACTATAATCTGTTGTTG-3' | (Reverse) |
| YRP098C | 5'-TCAAAACTACGGCTCATTTG-3' | (Forward) |
|  | 5'-TGAACAAAAGACTCAATCCG-3' | (Reverse) |

2.4. Salt Tolerance Assays

Salt tolerance assay were carried out as in the above-described. boric acid tolerance assays, except that SD media containing 1.75 M or 2 M NaCl were used.

2.5. Accession Numbers

The GenBank accession numbers for the sequences described in Example 2 are as follows: *Arabidopsis thaliana* sequences AtRBP45a, MN124872; AtRBP45b, MN101037; AtRBP45c, MN118834; AtRBP45d, MN121940; AtRBP47a, MN103848; AtRBP47b, MN112800; AtRBP47c, MN103642; AtRBP47c', MN103643; AtUBP1a, MN104285; AtUBP1b, MN101598; AtUBP1c, MN112266; and *Saccharomyces cerevisiae* sequences RPL7A, X62627; RPL7B, Z73554.

2.6. Result of Isolation of *Arabidopsis thaliana* cDNA Clones that Confer High Boric Acid Tolerance to Yeast

*Saccharomyces cerevisiae* strain Y01169 was transformed with an *Arabidopsis thaliana* cDNA expression library (Minet, M., Dufour, M. -E., & Lacroute, F. (1992) Plant J. 2, 417-422) and the transformants were selected on dishes containing 80 mM of boric acid. Boric acid at this concentration completely suppressed the formation of colonies of Y01169 cells even after two-week incubation at 26.5° C. In this screening, several colonies of yeast which showed enhanced boric acid tolerances were isolated. It was shown that one of the cDNA clones encodes an RNA binding protein, AtRBP47c'.

Figure 6:
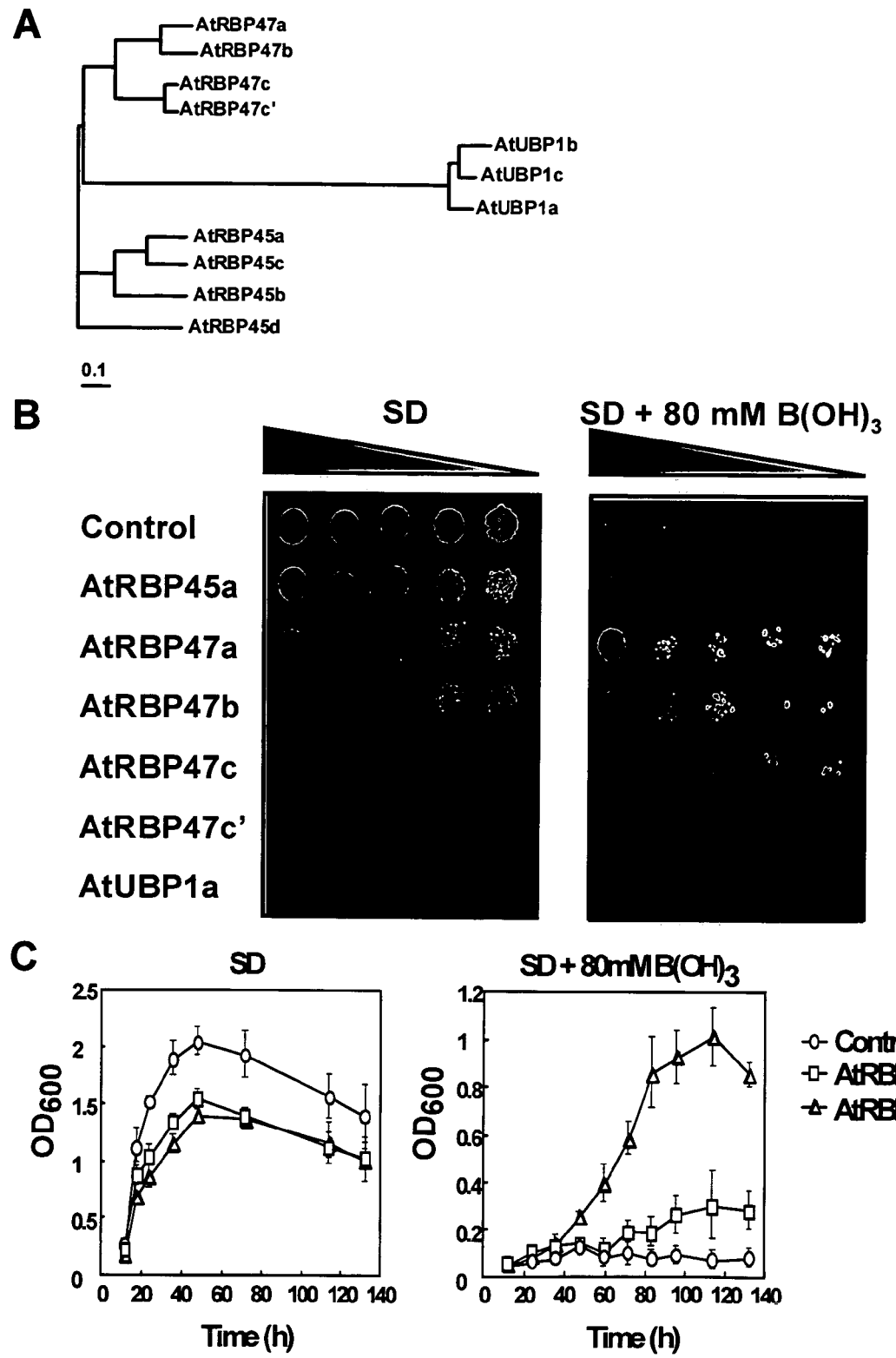
FIG. 6 is a set of pictures and graphs showing the results of boric acid tolerance test for AtRBP47c'-related genes-transformed yeast cells. (A) Phylogenetic tree of AtRBP47c'-related family proteins. The dendrogram indicates relative evolutionary distance among the AtRBP47c'-related family proteins and was prepared by using NJ method. The bar indicates the genetic distance for 0.1 amino acid substitutions/site. (B) Boric acid tolerance in solid medium. Yeast cells were grown to an $OD_{600}$ of 1.0, serially diluted, and then 10 µl of the diluent was spotted in SD plate added with 0 or 80 mM boric acid. The growth was recorded after culturing for 10 days. Yeast cells transformed with an empty pFL61 vector were used as a control. (C) Boric acid tolerance in liquid medium. Yeast cells were grown to an $OD_{600}$ of 1.0, and then diluted to an $OD_{600}$ of 0.1 in SD medium added with 0 or 80 mM boric acid. The diluted yeast cells were cultured at 30° C. and the values of $OD_{600}$ in indicated time after the dilution were recorded. Vertical bars represent the standard deviation of the mean±the mean of three replicate measurements.

2.7. Expression of AtRBP47c'-Related Genes from *Arabidopsis thaliana* Confers Boric Acid Tolerance to Yeast AtRBP47c' has three RNA recognition motifs (RRM). In *Arabidopsis thaliana* genome, there are eleven genes encoding a protein which has three RRMs and 100 or more of sequence identity scores to AtRBP47c' in BLASTP program. The phylogenetic tree of these AtRBP47c'-related family proteins is shown in FIG. 6A.

To investigate whether or not the expression of these *Arabidopsis thaliana* genes confers a boric acid tolerance to yeast, ORF sequences corresponding to 6 genes AtRBP45a, AtRBP47a, AtRBP47b, AtRBP47c, AtRBP47c', and AtUBP1a) were cloned into pFL61 expression vector. The plasmids were introduced into the yeast strain BY4741 and boric acid tolerances of these transformants were investigated. As shown in FIG. 6B, all of the 6 constructs conferred the ability to the yeast strains to grow on 80 mM boric acid-containing SD solid medium to varying extents. To compare the level of boric acid tolerances among those transformants, their growth rates in the presence of boric acid were analyzed in liquid culture. All transformants showed faster growth rate than the control. In the graph, the AtRBP47c'-expressing line showed the fastest growth rate (FIG. 6C).

2.8. Boric Acid Treatment Inhibits Splicing of RPL7B, but not RPL7A, in Yeast

The present inventors found that the over-expression of AtRBP47c'-related genes conferred a boric acid tolerance. Although roles of these genes in *A. thaliana* are still unknown, similar genes in other plant species were characterized. *Nicotiana plumbaginifolia* RBP45 (Simpson, C. G., Jennings, S. N., Clark, G. P., Thow, G., & Brown, J. W. S. (2004) Plant J. 37, 82-91) and UBP1 (Lambermon, M. H., Simpson, G. G., Wieczorek Kirk, D. A., Hemmings-Mieszczak, M., Klahre, U., & Filipowicz, W. (2000) EMBO J. 19, 1638-1649) were shown to enhance splicing efficiency. This led the present inventors to investigate the effect of boric acid on splicing of randomly selected 20 intron-containing genes in *Saccharomyces cerevisiae* by RT-PCR. Among the 6317 nuclear genes in the *Saccharomyces cerevisiae* genome, only 231 genes contain introns (see the website for the Munich Information Center for Protein Sequences. Among the 20 genes investigated, the increase by boric acid treatment in the accumulation of unspliced fragments compared to that of spliced fragments was observed in RPL7B, a gene encoding an essential ribosomal large subunit protein. This suggests that the splicing of RPL7B was inhibited in boric acid-treated yeast (FIG. 7B).

The RPL7B contains two introns. The size of unspliced fragments indicated that these fragments were derived from splicing of either one of the first and second introns (see FIG. 7A). To determine which intron is more susceptible to boric acid, the unspliced fragments were cloned and DNA sequences of the eight clones were determined. Six and two clones contained the first intron and the second intron, respectively. This suggests that inhibition occurs both at the first and the second introns and the first intron is more susceptible to high boric acid than the second one. The results also indicate that one of the two introns were correctly spliced, i.e., those unspliced fragments did not derive from genome DNA contamination but from the reverse transcription reaction of RNA.

Figure 7:
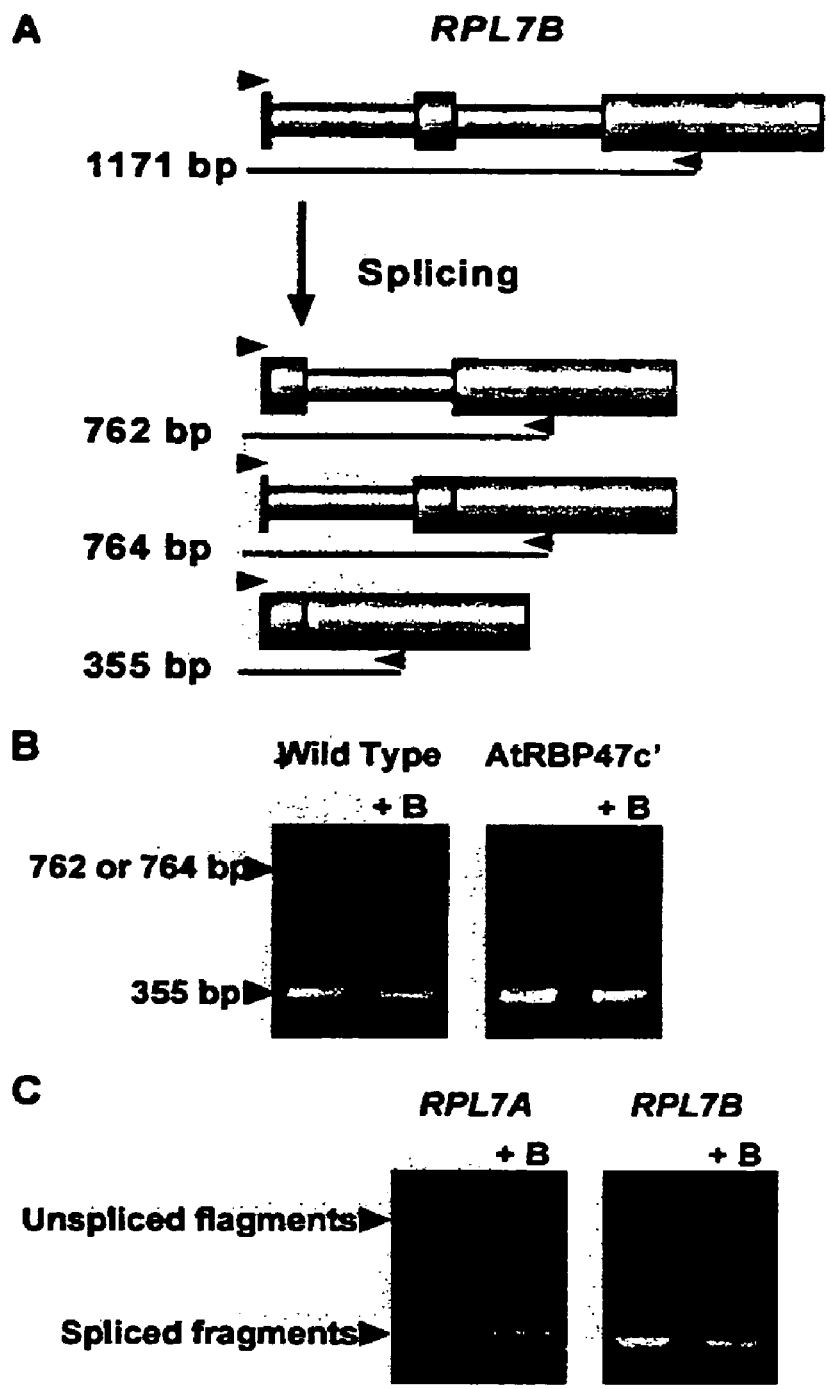
FIG. 7 is a figure showing the effect of boric acid on slicing. (A) Schematic representations of splicing of RPL7B. Three types of mRNA can be generated from pre-mRNA of RPL7B by splicing. Arrowheads indicate the locations of primers used for RT-PCR. (B) The effect of boric acid on splicing of RPL7B. Yeast cells were grown to an $OD_{600}$ of 1.0, and then boric acid was added to reach 80 mM at final concentrations. 24 hours later, the yeast cells were harvested and total RNA was isolated. cDNA was synthesized from the total RNA and was used a, a template for splicing analysis by PCR. In this analysis, yeast strain BY4741 (Wild Type) transformed with empty pFL61 vector or AtRBP47c'-expression vector (AtRBP47c') was used. (C) The effect of boric acid on splicing of RPL7A. Splicing of RPL7A was analyzed by RT-PCR in BY4741 transformed with pFL61.

Moreover, the inhibition of splicing of RPL7B by boric acid was not observed in yeast expressing AtRBP47c' (FIG. 7B). This result suggest that AtRBP47c' elevate splicing efficiency of RPL7B in the presence of high boric acid. It is possible that enhancement of splicing efficiency may be the cause of boric acid tolerance in yeast.

RPL7B has a paralog, RPL7A (SEQ ID NO: 32), in the yeast genome. RPL7A gene (SEQ ID NO: 31) also has two introns as in RPL7B gene. The effect of boric acid on the splicing of RPL7A was examined. The splicing inhibition by boric acid was not observed unlike in the case of RPL7B (FIG. 7C).

2.9. Disruption of RPL7A in Yeast Reduces Boric Acid Tolerance

Figure 8:
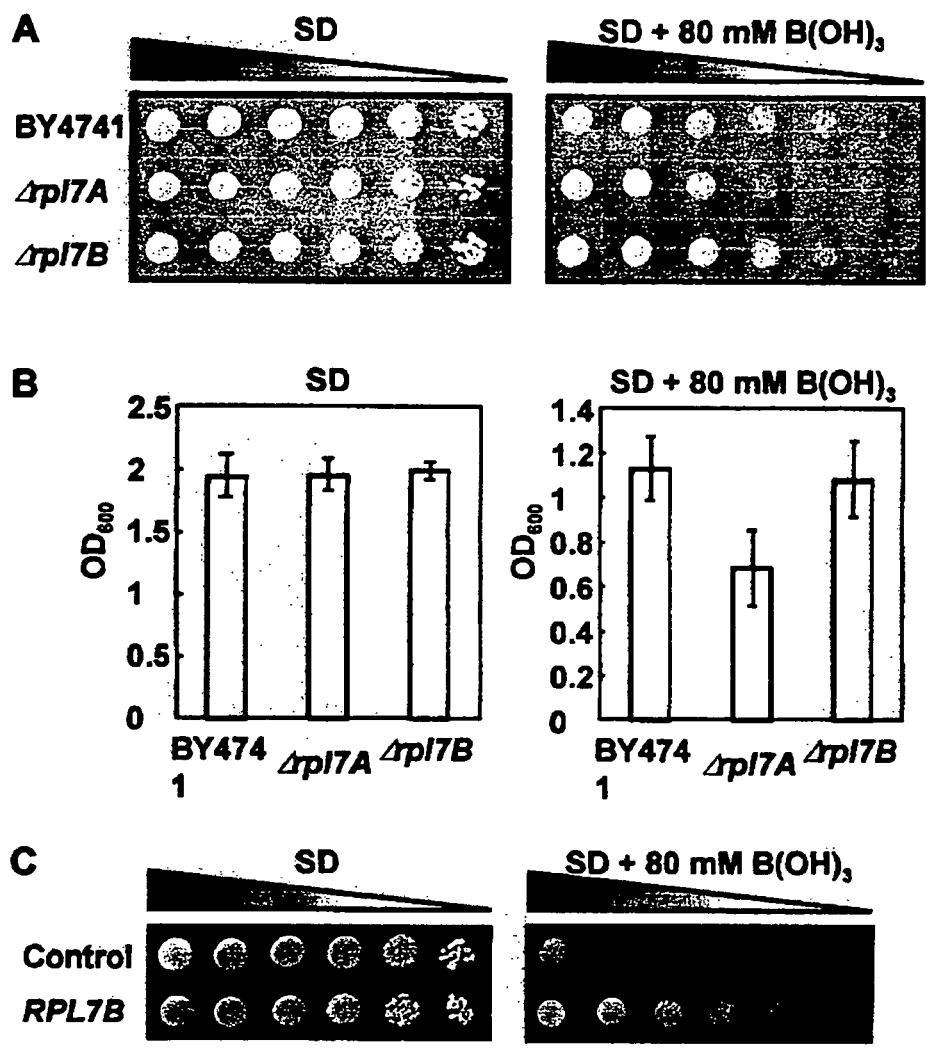
FIG. 8 is a set of pictures and graphs showing the results of boric aid tolerance test for RPL7A- or RPL7B-disrupted yeast cells. (A) Boric acid tolerance in solid medium. Yeast cells were grown to an $OD_{600}$ of 1.0, serially diluted, and then 10 µl of the diluent was spotted in SD plate added with 0 or 80 mM boric acid. The growth was recorded after culturing for 7 days. (B) Boric acid tolerance in liquid medium. Yeast cells were grown to an $OD_{600}$ of 1.0, and then diluted to an $OD_{600}$ of 0.1 in SD medium added with 0 or 80 mM boric acid. The diluted yeast cells were cultured at 30° C. for 21 hours (SD) and 60 hours (SD+80 mM boric acid) after the dilution, and then the values of $OD_{600}$ were recorded. Vertical bars represent the standard deviation of the mean±the mean of three replicate measurements. Δrpl7a and Δrpl7b represent RPL7A-disruption mutant (Y04443) and RPL7B-disruption mutant (Y01094), respectively. (C) The effect of over-expression of RPL7B on boric acid tolerance in RPL7A-disrupted yeast. Yeast cells were grown to an $OD_{600}$ of 1.0, serially diluted, and then 10 µl of the diluent was spotted in SD plate added with 0 or 80 mM boric acid. The growth was recorded after culturing for 5 days. Yeast cells transformed with an empty pDR195 vector were used as a control.

RPL7A and RPL7B Double Disruption Mutant is Lethal (see the website for the *Saccharomyces* Genome Database), indicating that RPL7 proteins are essential for yeast growth. Considering the differential sensitivity of boric acid to splicing between the two genes, it is possible that the boric acid tolerances of RPL7A- and RPL7B-disruption mutants differ. The Δrpl7b (Y01094) showed a similar level of boric acid tolerance to the wild type *Saccharomyces cerevisiae*, whereas a boric acid tolerance of the Δrpl7a (Y04443) was lower than the wild type (FIG. 8A). The difference in a boric acid tolerance was also evident in liquid culture (FIG. 8B). These results suggest that the inhibition of RPL7B splicing by boric acid is caused by reduction in a boric acid tolerance of Δrpl7a.

2.10. Expression of Intronless RPL7B in RPL7A-Disrupted Yeast Increases Boric Acid Tolerance If the reduction in a boric acid tolerance of Δrpl7a is due to the reduction in the level of RPL7 protein by inhibition of RPL7B splicing, expression of intronless RPL7B cDNA should increase the tolerance of Δrpl7a.

It was examined whether the expression of intronless RPL7B in Δrpl7a increases boric acid tolerance. ORF sequence of RPL7B was cloned into pDR195 expression vector. The plasmid was then introduced into the Δrpl7a and a boric acid tolerance in the transformant was investigated. As shown in FIG. 8C, the expression of intronless RPL7B increased boric acid tolerance in Δrpl7a. This result indicates that the inhibition of RPL7B splicing is the cause of growth cessation by highly concentrated boric acid in Δrpl7a.

Figure 9:
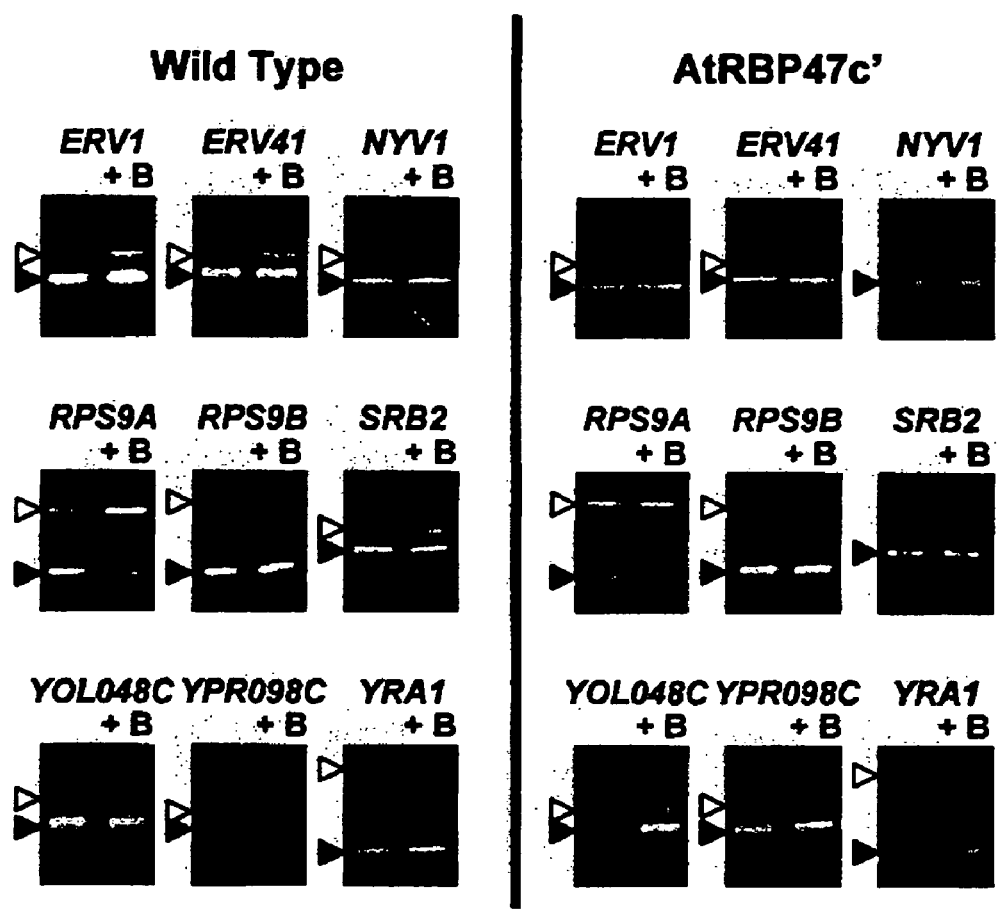
FIG. 9 is a set of pictures showing the effect of boric acid on splicing of genes containing noncanonical branchpoint sequences. Yeast were grown to an $OD_{600}$ of 1.0, and then boric acid was added to reach 80 mM at final concentrations. 24 hours later, the yeast cells were harvested, and total RNA was isolated to use as a template for splicing analysis by PCR. In this analysis, yeast strain BY4741 (Wild Type) transformed with empty pFL61 vector or AtRBP47c'-expression vector (AtRBP47c') was used. White and black arrowheads indicate unspliced and spliced fragments, respectively.

2.11. Analysis of Splicing Inhibition in Genes Containing Noncanonical Branchpoint Sequences by Boric Acid Treatment RPL7B has a noncanonical branchpoint sequence in its first intron (see Table 3). 28 genes containing such noncanonical branchpoint sequences among 231 nuclear intron-containing genes were found. Among the 28 genes, increase in the level of unspliced fragments by boric acid treatment compared to that of spliced fragments was observed in nine genes (FIG. 9). These genes are ERV1, ERV41, NYV1, RPS9A, RPS9B, SRB2, YOL048C, YPR098C, and YRA1.

TABLE 3

|  | 5' splice site | Branchpoint | 3' splice site |
|---|---|---|---|
| Consensus sequence | GUAUGU---------- | UACUAAC---------- | YAG |
| First intron | GUAUGU---------- | UGCUAAC---------- | UAG |
| Second intron | GUAUGU---------- | UACUAAC---------- | UAG |

Table 3 shows three consensus sequences, 5' splice site, branchpoint, and 3' splice site, that were recognized in yeast. A transition point from A to G in branchpoint of the first intron is represented by white letter in black background. Y represents pyrimidine ribonucleotides (C or U).

The effects of over-expression of AtRBP47c' on the splicing inhibition of those genes by boric acid was analyzed. As shown in FIG. 9, the level of splicing inhibition of NYV1 and SRB2 was impaired in yeast expressing AtRBP47c'. NYV1 and SRB2 encode v-SNARE protein and RNA polymerase II holoenzyme protein, respectively. These results strongly suggest that the mechanism of conferring a boric acid tolerance to yeast by over-expression of AtRBP47c' is the enhancement of splicing efficiency.

Figure 10:
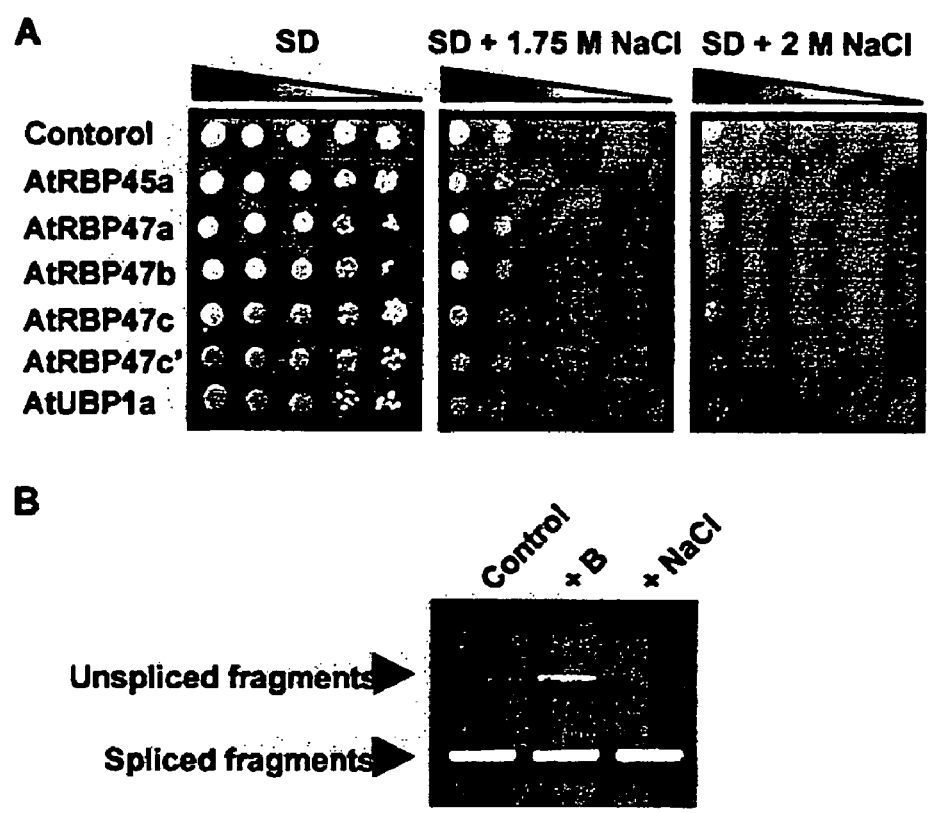
FIG. 10 is a set of pictures showing the effects of salt on growth of AtRBP47c'-related genes-transformed yeast cells and on splicing of RPL7B. (A) Salt tolerance in solid medium. Yeast cells were grown to an $OD_{600}$ of 1.0, serially diluted, and then 10 µl of the diluent was spotted in SD plate containing 0, 1.75 or 2 M NaCl. The growth was recorded after culturing for 7 days. Yeast cells transformed with an empty pFL61 vector were used as a control. (B) The effect of salt on splicing of RPL7B. Yeast cells were grown to an $OD_{600}$ of 1.0, and then NaCl or boric acid was added to reach 2 M or 80 mM at final concentrations, respectively. 24 hours later, the yeast cells were harvested and total RNA was isolated. cDNA was synthesized from the total RNA and was used as a template for splicing analysis by PCR.

2.12. Effects of Salt Treatment are Different from those of Boric Acid Treatment Over-expression of splicing factor genes confers salt tolerance to yeast and/or plants (Forment, J., Naranjo, M. A., Roldan, M., Serrano, R., & Vicente, O. (2002) Plant J. 30, 511-519, 2002; Serrano, R., Gaxiola, R., Rios, G., Forment, J., Vicente, O., & Ros, R. (2003) Monatsh. Chem. 134, 1445-1464). It was examined whether AtRBP47c'-related genes also confer salt tolerance to yeast. All six AtRBP47c'-related genes tested in this study did not increase the salt tolerance in yeast (FIG. 10A). Furthermore, inhibition of splicing of RPL7B was not observed in cells exposed to high salt (FIG. 10B). These results suggest that AtRBP47c'-related genes do not function in salt tolerance and that inhibition of RPL7B splicing is likely to be unique to boric acid treatment.

2.13. Discussion

AtRBP47c' was isolated from *Arabidopsis thaliana* as a gene that confers a boric acid tolerance to yeast cells by yeast complementation. In yeast genome, there are seven genes encoding a protein-which has three RRMs and 100 or more of sequence identity scores to AtRBP47c' in BLASTP program. Among these genes, the most similar gene to AtRBP47c' is NAM8. Although NAM8 was originally isolated as a suppressor of mitochondrial splicing deficiencies (Ekwall, K., Kermorgant, M., Dujardin, G., Groudinsky, O., & Slonimski, P. P. (1992) Mol. Gene. Genet.233, 136-144), subsequent analysis showed that NAM8 interacts with U1snRNA and that NAM8 is indispensable for efficient 5' splice site recognition when this process is impaired as a result of the presence of nonconical 5' slice sites (Gottschalk, A, Tang, J., Puig, O., Salgado, J., Neubauer, G., Colot, H. V., Mann, M., Seraphin, B., Rosbash, M., Luhrmann, R., & Fabrizio, P. (1998) RNA 4, 374-393.; Puig, O., Gottschalk, A., Fabrizio, P., & Seraphin, B. (1999) Gene. Dev. 13, 569-580). From these observations, it was hypothesized that AtRBP47c' might play a similar role with NAM8 in a boric acid tolerance. However, over-expression of NAM8 did not confer a boric acid tolerance to yeast and NAM8-disrupted mutants were tolerant to boric acid as well as wild type, indicating that AAtRBP47c' has possibilities to be involved in an another step of splicing processes and/or other reaction(s) in boric acid tolerance.

In this study, it was found that boric acid could inhibit splicing of RPL7B among randomly selected 20 genes in yeast (FIG. 7B). By analysis of the DNA sequence in the first intron of this gene, it became clear that the first intron has a transition in the consensus sequence of the branchpoint. As shown in Table 1, the second A in the branchpoint consensus sequence is converted to G in the first intron of RPL7B. The binding of branchpoint bridging protein (BBP) to the branchpoint is a critical step in splicing progression (Abovich and Rosbash, 1997). Affinity between BBP and branchpoint sequence is known to be an important factor for splicing efficiency (Champion-Arnaud, et al., 1995). It has been reported that especially, this type of transition from A to G in second nucleotide of branchpoint sequence showed an approximately 10% decrease in the affinity with BBP (Berglund, J. A., Chua, K., Abovich, N., Reed, R., & Rosbash, M. (1997) Cell 89, 781-787). Therefore, it is likely that RPL7B is one of the genes with low splicing efficiency.

It is reported that the second step of splicing is inhibited by boric acid treatment in HeLa cell in vitro splicing system (Shomron, N., & Ast, G. (2003) FEBS Lett. 552, 219-224). The second step of splicing is a process in which the treated 3' end of an exon is ligated to 5' end of the next exon. Considering that boric acid binds to cis-diol in ribose (Ralston, N. V. C., & Hunt, C. D. (2000) FASEB J. 14, A538; Nicholas et al., 2001; Ricardo, A., Carrigan, M. A., Olcott, A. N., & Benner, S. A. (2004) Science 303, 196), it is likely that the ligation reaction in second step of splicing is inhibited by the binding of boric acid to the 3' end of an exon. The above Shomron and Ast (2003) has been reported that inhibition of splicing by boric acid at the second step is a general phenomenon, as five different mRNA precursors exhibited a similar pattern of inhibition. In that case, inhibition of the splicing in yeast should occur similarly with all introns. However, among the 20 genes tested in the initial step of this study, the only gene in which inhibition was observed was RPL7B (FIG. 7B).

A possible explanation of this specific inhibition is as follows. The inhibition of splicing in the second step by boric acid takes place with all intron-containing genes in yeast. At this step, intron-including splicing intermediates, which should be rapidly degraded when the splicing progresses normally, accumulate. The accumulation of intermediates inhibits normal turnover. In such a situation, genes having introns with low splicing efficiency are likely to be more susceptible to the inhibition of splicing by boric acid. As one of such genes, a gene containing a noncanonical branchpoint sequence such as RPL7B can be exemplified. This speculation was verified by analysis of the inhibition of splicing by high boric acid on other genes having the same feature (FIG. 9). In the analysis, it was found that high boric acid treatment inhibits splicing of nine genes containing noncanonical branchpoint sequences except for RPL7B. This result clearly indicates that one of the toxic mechanisms of boric acid is inhibition of splicing of genes having introns with low splicing efficiency. Moreover, it was found that the splicing inhibitions of two genes among those nine genes were impaired by over-expression of AtRBP47c' (FIG. 9). This result suggests that a boric acid tolerance by over-expression of AtRBP47c' may be achieved by the enhancement of splicing efficiency of part of genes among many genes of which splicing is inhibited during high boric acid treatment. Hence, splicing inhibition of a limited number of genes might be a cause of growth inhibition.

The AtRBP47c'-related proteins have three RRMs. RNA binding activity of RBP45, RBP47, and UBP1 of *N. plumbaginifolia* has been confirmed. All of these proteins tend to bind with U-rich sequence (Lambermon, M. H., Simpson, G. G., Wieczorek Kirk, D. A., Hemmings-Mieszczak, M., Klahre, U., & Filipowicz, W. (2000) EMBO J. 19, 1638-1649: Lorkovic, Z. J., Wieczorek Kirk, D. A., Klahre, U., Hemmings-Mieszczak, M., & Filipowicz, W. (2000). RNA 6, 1610-1624). Moreover, deletion analysis of RBP45 in *N. plumbaginifolia* indicated that at least two RRMs are required for interaction with RNA (Lorkovic et al., 2000). Although an RRM was thought to be involved in RNA binding, it was shown that an RRM of a certain protein participates in interaction with other proteins (Kielkopf, C. L., Lucke, S., & Green, M. R. (2004) Gene Dev. 18, 1513-1526). Especially, yeast U2AF$^{65}$, a splicing factor containing three RRMs, is reported that the third RRM is bound to BBP (Rain, J. C., Rafi, Z., Rhani, Z., Legrain, P., & Kramer, A. (1998) RNA 4, 551-565). These results suggest that AtRBP47c' may also interact with BBP. Furthermore, analysis of RBP7B first intron and SRB2 intron sequences revealed that there are U-rich sequences at the 3' side of the branchpoint. Taking the results together, it was hypothesized that AtRBP47c' stabilizes the interaction of BBP with branchpoint and the U-rich sequence of the branchpoint by binding with BBP, and as a result, the efficiency of splicing is increased.

It is reported that splicing is also inhibited by salt stress. Furthermore, over-production of several splicing factors such as SR protein have been also reported to increase salt tolerance in yeast and plants (Forment, J., Naranjo, M. A., Roldan, M., Serrano, R., & Vicente, O. (2002) Plant J. 30,511-519, 2002; Serrano, R., Gaxiola, R., Rios, G., Forment, J., Vicente, O., & Ros, R. (2003) Monatsh. Chem. 134, 1445-1464). In the present study, however, over-expression of AtRBP47c'-related genes did not confer salt tolerance to yeast (FIG. 10A), and inhibition of splicing of RPL7B was not detected after salt treatment (FIG. 10B). These results suggest that the mechanism of splicing inhibition is different between salt treatment and boric acid treatment.

Example 2 is the first report showing that the key of the toxic mechanisms of boric acid is the specific inhibition of splicing and that genes involved in enhancement of splicing efficiency lead to the boric acid tolerance. However, the toxic mechanisms other than the inhibition of splicing should exist, since-toxic effect of boric acid is observed in the prokaryotes in which splicing are not performed.

The invention is further described by the following numbered paragraphs:

1. A DNA encoding a protein that has an activity of conferring a boric acid tolerance and consists of the amino acid sequence shown by SEQ ID NO: 2, 4, 6, 8, 10, 12, 14, 16, 18, 20, 22, 24, 26, 28 or 30.

2. A DNA encoding a protein that consists of the amino acid sequence shown by SEQ ID NO: 2, 4, 6, 8, 10, 12, 14, 16, 18, 20, 22, 24, 26, 28 or 30 and has an activity of conferring a boric acid tolerance.

3. A gene DNA conferring a boric acid tolerance, which consists of the base sequence shown by SEQ ID NO: 1, 3, 5, 7, 9, 11, 13, 15, 17, 19, 21, 23, 25, 27 or 29 or a complementary sequence thereof.

4. A DNA encoding a protein that consists of a base sequence wherein one or a few bases are deleted, substituted or added in the base sequence shown by SEQ ID NO: 1, 3, 5, 7, 9, 11, 13, 15, 17, 19, 21, 23, 25, 27 or 29, and has an activity of conferring a boric acid tolerance.

5. A DNA encoding a protein that hybridizes with the DNA according to paragraph 3 under stringent conditions and has an activity of conferring a boric acid tolerance.

6. A protein having an activity of conferring a boric acid tolerance, which consists of the amino acid sequence shown by SEQ ID NO: 2, 4, 6, 8, 10, 12, 14, 16, 18, 20, 22, 24, 26, 28 or 30.

7. A protein consisting of an amino sequence wherein one or a few amino acids are deleted, substituted or added in the amino sequence shown by SEQ ID NO: 2, 4, 6, 8, 10, 12, 14, 16, 18, 20, 22, 24, 26, 28 or 30; and having an activity of conferring a boric acid tolerance.

8. A recombinant vector including the DNA according to any one of paragraphs 1 to 5, which can express a protein conferring a boric acid tolerance.

9. A transformant wherein the recombinant vector according to paragraph 8 is introduced, which can express a protein conferring a boric acid tolerance.

10. The transformant according to paragraph 9 wherein the transformant is yeast.

11. The transformant according to paragraph 9 wherein the transformant is a plant.

12. A method for screening a gene conferring a boric acid tolerance, comprising the steps of transforming a YNL275w-disrupted yeast which is deficient in and not expressing YNL275w gene by using a gene library, culturing the obtained transformed YNL275w-disrupted yeast in a medium containing boric acid, and measuring/evaluating an activity of conferring a boric acid tolerance of the transformed YNL275w-disrupted yeast.

13. A method for screening a gene conferring a boric acid tolerance wherein an enhancement level of splicing efficiency is measured/evaluated by targeting a specific inhibition of splicing by boric acid.

14. The method for screening a gene conferring a boric acid tolerance according to paragraph 13, comprising the steps of expressing a test substance in yeast cells, culturing the expressed test substance in the presence of boric acid, and measuring/evaluating an improvement level of a specific inhibition of splicing by boric acid in an intron-containing gene in yeast, as an enhancement level of splicing efficiency.

15. The method for screening a gene conferring a boric acid tolerance according to paragraph 14 wherein the gene containing intron in yeast is a gene RPL7B in *Saccharomyces cerevisiae* genome.

16. Use of the DNA according to any one of paragraphs 1 to 5 as a gene conferring a boric acid tolerance.

17. Use of the DNA according to any one of paragraphs 1 to 5 for producing a plant or yeast conferred a boric acid tolerance.

18. Use of the protein according to paragraph 6 or 7 as a protein having an activity of conferring a boric acid tolerance.

19. Use of the protein according to paragraph 6 or 7 for producing a plant or yeast conferred a boric acid tolerance.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for conferring boric acid tolerance to a yeast comprising:
   i) introducing the DNA of SEQ ID NO: 3 operably linked to a promoter into the yeast;
   ii) culturing the yeast in the presence of boric acid and expressing the DNA of SEQ ID NO: 3 to confer boric acid tolerance to the yeast; and
   iii) selecting the yeast in which tolerance to 80 mM boric acid is conferred.

* * * * *

SEQUENCE LISTING

<160> NUMBER OF SEQ ID NOS: 134

<210> SEQ ID NO 1
<211> LENGTH: 1332
<212> TYPE: DNA
<213> ORGANISM: Arabidopsis thaliana

<400> SEQUENCE: 1
atgttgctca atgacaagca agtgtatgtg ggtcctttcc tgaggagaca agaaagagac        60

```
tccactgcta acaaaacgaa attcaccaat gtgtatgtga agaatctcgc ggaaagtact    120
accgatgatg acttgaagaa tgcttttggc gagtatggaa agataacaag tgctgtcgtg    180
atgaaagatg gagaagggaa gtccaagggc tttgggtttg tcaactttga aaatgctgat    240
gatgctgcta gggctgtgga gtctctcaat gggcacaaat ttgatgataa ggagtggtat    300
gttggtagag cccagaagaa gtcagagagg gaaacagaat taagggtccg ttatgaacag    360
aatttgaagg aagctgcaga caagtttcaa agttcaaact tgtatgttaa gaatttggat    420
cctagcattt cagatgagaa acttaaagag atcttttctc cttttggtac cgttacatct    480
agcaaggtga tgcgggatcc taatggaaca agcaaaggct caggttttgt tgctttcgca    540
actcccgaag aagcaactga agctatgtca cagttgagcg gtaaaatgat cgaaagcaag    600
ccactctatg tggctattgc acagcggaag gaagacagaa gggtcagact acaggctcag    660
ttttcccaag tgaggccagt tgcaatgcag ccgtctgttg gtccccgcat gccagtgtat    720
cccccgggtg gtcctggtat tggacaacaa atgttctatg tcaggccccc tcctgccatg    780
attcctcccc agcctgggta tggataccaa cagcagcttg ttcctggaat gagacctggt    840
gggggtcctg tacccagttt cttcatgcct atggttcagc cacagcagca gcgtcctgga    900
ggaggaagac gtcctggggg aatccaacac tcccagcagc aaaatcccat gatgcagcaa    960
cagatgcatc caaggggtcg gatgttccgg tatccccaag ggcgtggtgg tagtggtgat   1020
gtgcctccat atgatatggg caacaacatg ccattgacta ttggagcttt ggcttcaaat   1080
ctgtctaatg ctactccaga gcaacagagg acgatgctgg tgaggtgct gtacccgttg    1140 gtggagcagg ttgaggcaga gtctgcagcc aaagtgactg ggatgctttt ggagatggac   1200
cagactgaag tgctccatct gttggagtca ccagaagctc tcaaggccaa agttgcagag   1260
gctatggatg ttctcaggag tgtcgctgct ggtggtgcaa ccgagcagct cgcttccttg   1320
aacctctctt aa                                                       1332
```

<210> SEQ ID NO 2
<211> LENGTH: 443
<212> TYPE: PRT
<213> ORGANISM: Arabidopsis thaliana

<400> SEQUENCE: 2

```
Met Leu Leu Asn Asp Lys Gln Val Tyr Val Gly Pro Phe Leu Arg Arg
1               5                   10                  15

Gln Glu Arg Asp Ser Thr Ala Asn Lys Thr Lys Phe Thr Asn Val Tyr
            20                  25                  30

Val Lys Asn Leu Ala Glu Ser Thr Thr Asp Asp Leu Lys Asn Ala
        35                  40                  45

Phe Gly Glu Tyr Gly Lys Ile Thr Ser Ala Val Val Met Lys Asp Gly
    50                  55                  60

Glu Gly Lys Ser Lys Gly Phe Gly Phe Val Asn Phe Glu Asn Ala Asp
65                  70                  75                  80

Asp Ala Ala Arg Ala Val Glu Ser Leu Asn Gly His Lys Phe Asp Asp
                85                  90                  95

Lys Glu Trp Tyr Val Gly Arg Ala Gln Lys Lys Ser Glu Arg Glu Thr
            100                 105                 110

Glu Leu Arg Val Arg Tyr Glu Gln Asn Leu Lys Glu Ala Ala Asp Lys
        115                 120                 125

Phe Gln Ser Ser Asn Leu Tyr Val Lys Asn Leu Asp Pro Ser Ile Ser
    130                 135                 140
```

```
Asp Glu Lys Leu Lys Glu Ile Phe Ser Pro Phe Gly Thr Val Thr Ser
145                 150                 155                 160

Ser Lys Val Met Arg Asp Pro Asn Gly Thr Ser Lys Gly Ser Gly Phe
            165                 170                 175

Val Ala Phe Ala Thr Pro Glu Glu Ala Thr Glu Ala Met Ser Gln Leu
        180                 185                 190

Ser Gly Lys Met Ile Glu Ser Lys Pro Leu Tyr Val Ala Ile Ala Gln
    195                 200                 205

Arg Lys Glu Asp Arg Arg Val Arg Leu Gln Ala Gln Phe Ser Gln Val
210                 215                 220

Arg Pro Val Ala Met Gln Pro Ser Val Gly Pro Arg Met Pro Val Tyr
225                 230                 235                 240

Pro Pro Gly Gly Pro Gly Ile Gly Gln Gln Met Phe Tyr Gly Gln Ala
                245                 250                 255

Pro Pro Ala Met Ile Pro Pro Gln Pro Gly Tyr Gly Tyr Gln Gln Gln
            260                 265                 270

Leu Val Pro Gly Met Arg Pro Gly Gly Pro Val Pro Ser Phe Phe
        275                 280                 285

Met Pro Met Val Gln Pro Gln Gln Arg Pro Gly Gly Gly Arg Arg
290                 295                 300

Pro Gly Gly Ile Gln His Ser Gln Gln Gln Asn Pro Met Met Gln Gln
305                 310                 315                 320

Gln Met His Pro Arg Gly Arg Met Phe Arg Tyr Pro Gln Gly Arg Gly
                325                 330                 335

Gly Ser Gly Asp Val Pro Pro Tyr Asp Met Gly Asn Asn Met Pro Leu
            340                 345                 350

Thr Ile Gly Ala Leu Ala Ser Asn Leu Ser Asn Ala Thr Pro Glu Gln
        355                 360                 365

Gln Arg Thr Met Leu Gly Glu Val Leu Tyr Pro Leu Val Glu Gln Val
    370                 375                 380

Glu Ala Glu Ser Ala Ala Lys Val Thr Gly Met Leu Leu Glu Met Asp
385                 390                 395                 400

Gln Thr Glu Val Leu His Leu Leu Glu Ser Pro Glu Ala Leu Lys Ala
                405                 410                 415

Lys Val Ala Glu Ala Met Asp Val Leu Arg Ser Val Ala Ala Gly Gly
            420                 425                 430

Ala Thr Glu Gln Leu Ala Ser Leu Asn Leu Ser
        435                 440

<210> SEQ ID NO 3
<211> LENGTH: 1305
<212> TYPE: DNA
<213> ORGANISM: Arabidopsis thaliana

<400> SEQUENCE: 3
atggcagacg tcaaggttca atccgaatcc gaatcctcgg attctcatcc cttggtcgac       60
tatcaatcac ttccacctta tcctccgccg catccaccgg ttgaagtaga ggagaatcaa      120
ccaaaaacat ctccgactcc gccgccgcca cactggatgc gttatccacc ggtgttaatg      180
cctcagatga tgtacgcgcc gccgccaccg atgccgttct caccttatca tcaatatccg      240
aatcaccacc actttcacca tcaatctcgt ggtaataagc atcaaaacgc ttttaatggt      300
gagaataaaa ctatttgggt tggtgatttg caaaactgga tggatgaggc ttatcttaat      360 tctgcttta cttccgccga agagagagag attgtttcgc tgaaggtgat tcgtaataag      420
```

```
cacaatggtt catcggaagg atatggattt gtggagtttg agtcccatga tgtagctgat        480
aaggttttgc aggagtttaa cggggcgcct atgccaaata ctgaccaacc ttttcgtttg        540
aactgggcta gttttagcac cggtgagaag cggttagaga acaatggacc tgatctctct        600
atatttgttg gggatttggc gccagatgtt tcggatgctt tgttgcacga gaccttctct        660
gagaagtatc cgtcggttaa agctgccaaa gttgtccttg atgctaatac tggtagatca        720
aaggggtatg ggtttgtgag gtttggagat gagaatgaaa ggaccaaagc aatgactgag        780
atgaatggtg ttaaatgctc tagtagagct atgcgtatcg gtcctgctac cccaaggaaa        840
actaatggtt atcaacaaca aggtggatac atgccgagtg gtgcctttac gcgttctgaa        900
ggggacacaa tcaacacaac aatatttgtt ggagggcttg actctagtgt cactgatgaa        960
gacttaaagc aaccttctc tgaattcggg gaaatagtgt ctgtcaagat tcctgttggt       1020
aaaggatgcg gatttgttca gtttgttaac agaccaaatg cagaggaggc tttggaaaaa       1080
ctcaatggga ctgtaattgg caaacaaaca gtccggcttt cttggggccg taatccagcc       1140
aataagcagc ctagagataa gtatggaaac caatggggttg atccgtacta tggaggacag       1200
ttttacaatg ggtatggata catggtacct caacctgacc cgagaatgta tcctgctgca       1260
ccttactatc caatgtacgg tggtcatcag caacaagtta gctga                       1305

<210> SEQ ID NO 4
<211> LENGTH: 434
<212> TYPE: PRT
<213> ORGANISM: Arabidopsis thaliana

<400> SEQUENCE: 4

Met Ala Asp Val Lys Val Gln Ser Glu Ser Glu Ser Ser Asp Ser His
1               5                   10                  15

Pro Leu Val Asp Tyr Gln Ser Leu Pro Pro Tyr Pro Pro Pro His Pro
            20                  25                  30

Pro Val Glu Val Glu Glu Asn Gln Pro Lys Thr Ser Pro Thr Pro Pro
        35                  40                  45

Pro Pro His Trp Met Arg Tyr Pro Pro Val Leu Met Pro Gln Met Met
    50                  55                  60

Tyr Ala Pro Pro Pro Met Pro Phe Ser Pro Tyr His Gln Tyr Pro
65                  70                  75                  80

Asn His His His Phe His His Gln Ser Arg Gly Asn Lys His Gln Asn
                85                  90                  95

Ala Phe Asn Gly Glu Asn Lys Thr Ile Trp Val Gly Asp Leu Gln Asn
            100                 105                 110

Trp Met Asp Glu Ala Tyr Leu Asn Ser Ala Phe Thr Ser Ala Glu Glu
        115                 120                 125

Arg Glu Ile Val Ser Leu Lys Val Ile Arg Asn Lys His Asn Gly Ser
    130                 135                 140

Ser Glu Gly Tyr Gly Phe Val Glu Phe Glu Ser His Asp Val Ala Asp
145                 150                 155                 160

Lys Val Leu Gln Glu Phe Asn Gly Ala Pro Met Pro Asn Thr Asp Gln
                165                 170                 175

Pro Phe Arg Leu Asn Trp Ala Ser Phe Ser Thr Gly Glu Lys Arg Leu
            180                 185                 190

Glu Asn Asn Gly Pro Asp Leu Ser Ile Phe Val Gly Asp Leu Ala Pro
        195                 200                 205

Asp Val Ser Asp Ala Leu Leu His Glu Thr Phe Ser Glu Lys Tyr Pro
    210                 215                 220
```

Ser Val Lys Ala Ala Lys Val Val Leu Asp Ala Asn Thr Gly Arg Ser
225                 230                 235                 240

Lys Gly Tyr Gly Phe Val Arg Phe Gly Asp Glu Asn Glu Arg Thr Lys
            245                 250                 255

Ala Met Thr Glu Met Asn Gly Val Lys Cys Ser Ser Arg Ala Met Arg
        260                 265                 270

Ile Gly Pro Ala Thr Pro Arg Lys Thr Asn Gly Tyr Gln Gln Gln Gly
    275                 280                 285

Gly Tyr Met Pro Ser Gly Ala Phe Thr Arg Ser Glu Gly Asp Thr Ile
290                 295                 300

Asn Thr Thr Ile Phe Val Gly Leu Asp Ser Ser Val Thr Asp Glu
305                 310                 315                 320

Asp Leu Lys Gln Pro Phe Ser Glu Phe Gly Glu Ile Val Ser Val Lys
                325                 330                 335

Ile Pro Val Gly Lys Gly Cys Gly Phe Val Gln Phe Val Asn Arg Pro
            340                 345                 350

Asn Ala Glu Glu Ala Leu Glu Lys Leu Asn Gly Thr Val Ile Gly Lys
        355                 360                 365

Gln Thr Val Arg Leu Ser Trp Gly Arg Asn Pro Ala Asn Lys Gln Pro
    370                 375                 380

Arg Asp Lys Tyr Gly Asn Gln Trp Val Asp Pro Tyr Tyr Gly Gly Gln
385                 390                 395                 400

Phe Tyr Asn Gly Tyr Gly Tyr Met Val Pro Gln Pro Asp Pro Arg Met
                405                 410                 415

Tyr Pro Ala Ala Pro Tyr Tyr Pro Met Tyr Gly Gly His Gln Gln Gln
            420                 425                 430

Val Ser

<210> SEQ ID NO 5
<211> LENGTH: 369
<212> TYPE: DNA
<213> ORGANISM: Arabidopsis thaliana

<400> SEQUENCE: 5
atggcgtatg aaccgatgaa gcccacgaaa gctggtttgg aggctcctct ggagcagatt      60
cataagatca ggatcactct ctcttcaaaa aatgtgaaga acttggaaaa agtgtgcact     120
gatttggtcc gtggagctaa ggataagaga cttagagtta agggaccagt gagaatgccc     180
actaaggttc ttaagatcac taccagaaag gcaccttgtg gtgaaggtac caatacttgg     240
gacaggtttg agctcagggt tcacaagcgt gtcatcgatc tcttcagctc ccctgacgtt     300
gttaagcaaa tcacgtctat caccattgag cccggtgttg aggtcgaggt cactattgct     360
gactcttag                                                              369

<210> SEQ ID NO 6
<211> LENGTH: 122
<212> TYPE: PRT
<213> ORGANISM: Arabidopsis thaliana

<400> SEQUENCE: 6

Met Ala Tyr Glu Pro Met Lys Pro Thr Lys Ala Gly Leu Glu Ala Pro
1               5                   10                  15

Leu Glu Gln Ile His Lys Ile Arg Ile Thr Leu Ser Ser Lys Asn Val
            20                  25                  30

Lys Asn Leu Glu Lys Val Cys Thr Asp Leu Val Arg Gly Ala Lys Asp

```
                35                  40                  45
Lys Arg Leu Arg Val Lys Gly Pro Val Arg Met Pro Thr Lys Val Leu
        50                  55                  60

Lys Ile Thr Thr Arg Lys Ala Pro Cys Gly Glu Gly Thr Asn Thr Trp
 65                  70                  75                  80

Asp Arg Phe Glu Leu Arg Val His Lys Arg Val Ile Asp Leu Phe Ser
                85                  90                  95

Ser Pro Asp Val Val Lys Gln Ile Thr Ser Ile Thr Ile Glu Pro Gly
            100                 105                 110

Val Glu Val Glu Val Thr Ile Ala Asp Ser
        115                 120

<210> SEQ ID NO 7
<211> LENGTH: 741
<212> TYPE: DNA
<213> ORGANISM: Arabidopsis thaliana

<400> SEQUENCE: 7
atggggagaa gaccatgctg tgagaagata ggattgaaga aagggccatg gagtgctgaa      60
gaagatcgaa tcttgatcaa ttatattagt ctccatggcc atcccaattg agagagctctc    120 cctaaactag ccgggctact tcggtgcgga aaaagttgca ggcttcgttg gattaattat     180
ttgagaccag acatcaaacg tggcaatttc actcctcatg aagaagatac tatcatcagc    240
ttacatcaac tcttaggcaa cagatggtct gcgatagctg caaaattgcc tggacgaaca    300
gacaacgaaa ttaaaaatgt tggcacacact catttaaaga aaagactcca ccacagtcaa   360
gatcaaaaca acaaggaaga tttcgtctct actacagctg cggagatgcc aacctctccg    420
caacaacaat ctagtagtag tgccgacatt tcagcaatta caacattggg aaacaacaat    480
gacatctcca atagcaacaa agactccgcg acgtcatccg aagatgttct tgcaattata    540
gatgagagct tttggtcaga agtggtattg atggactgtg acatttcagg aaatgagaag    600
aatgagaaaa agatagagaa ttgggagggc tcactagata gaaacgataa gggatataac    660
catgacatgg agttttggtt tgaccatctc actagtagta gttgtataat tggagaaatg    720
tccgacattt ctgagttttg a                                              741

<210> SEQ ID NO 8
<211> LENGTH: 246
<212> TYPE: PRT
<213> ORGANISM: Arabidopsis thaliana

<400> SEQUENCE: 8

Met Gly Arg Arg Pro Cys Cys Glu Lys Ile Gly Leu Lys Lys Gly Pro
  1               5                  10                  15

Trp Ser Ala Glu Glu Asp Arg Ile Leu Ile Asn Tyr Ile Ser Leu His
             20                  25                  30

Gly His Pro Asn Trp Arg Ala Leu Pro Lys Leu Ala Gly Leu Leu Arg
         35                  40                  45

Cys Gly Lys Ser Cys Arg Leu Arg Trp Ile Asn Tyr Leu Arg Pro Asp
     50                  55                  60

Ile Lys Arg Gly Asn Phe Thr Pro His Glu Glu Asp Thr Ile Ile Ser
 65                  70                  75                  80

Leu His Gln Leu Leu Gly Asn Arg Trp Ser Ala Ile Ala Ala Lys Leu
                85                  90                  95

Pro Gly Arg Thr Asp Asn Glu Ile Lys Asn Val Trp His Thr His Leu
            100                 105                 110
```

```
Lys Lys Arg Leu His His Ser Gln Asp Gln Asn Asn Lys Glu Asp Phe
            115                 120                 125
Val Ser Thr Thr Ala Ala Glu Met Pro Thr Ser Pro Gln Gln Gln Ser
        130                 135                 140
Ser Ser Ser Ala Asp Ile Ser Ala Ile Thr Thr Leu Gly Asn Asn Asn
145                 150                 155                 160
Asp Ile Ser Asn Ser Asn Lys Asp Ser Ala Thr Ser Ser Glu Asp Val
                165                 170                 175
Leu Ala Ile Ile Asp Glu Ser Phe Trp Ser Glu Val Val Leu Met Asp
            180                 185                 190
Cys Asp Ile Ser Gly Asn Glu Lys Asn Glu Lys Lys Ile Glu Asn Trp
        195                 200                 205
Glu Gly Ser Leu Asp Arg Asn Asp Lys Gly Tyr Asn His Asp Met Glu
    210                 215                 220
Phe Trp Phe Asp His Leu Thr Ser Ser Ser Cys Ile Ile Gly Glu Met
225                 230                 235                 240
Ser Asp Ile Ser Glu Phe
                245

<210> SEQ ID NO 9
<211> LENGTH: 1125
<212> TYPE: DNA
<213> ORGANISM: Arabidopsis thaliana

<400> SEQUENCE: 9
atgggaagag caccgtgttg tgataaggcc aacgtgaaga aagggccttg gtctcctgag      60
gaagacgcca aactcaaaga ttacatcgag aatagtggca caggaggcaa ctggattgct     120
ttgcctcaga aaattggttt aaggagatgt gggaagagtt gcaggctaag gtggctcaac     180
tatttgagac caaacatcaa acatggtggc ttctccgagg aagaagacaa catcatttgt     240
aacctctatg ttactattgg tagcaggtgg tctataattg ctgcacaatt gccgggaaga     300
accgacaacg tatcaaaaa ctattggaac acgaggctga agaagaagct tctgaacaaa     360
caaaggaaag agttccaaga agcgcgaatg aagcaagaga tggtgatgat gaaaaggcaa     420
caacaaggac aaggacaagg tcaaagtaat ggtagtacgg atctttatct taacaacatg     480
tttggatcat caccatggcc attactacca caacttcctc ctccacatca tcaaatacct     540
cttggaatga tggaaccaac aagctgtaac tactaccaaa cgacaccgtc ttgtaaccta     600
gaacaaaagc cattgatcac actcaagaac atggtcaaga ttgaagaaga acaggaaagg     660
acaaaccctg atcatcatca tcaagattct gtcacaaacc ttttgatttt ctctttctct     720
cagcttttgt tagatcccaa ttactatctg ggatcaggag gggaggaga aggagatttt     780
gctatcatga gcagcagcac aaactcacca ttaccaaaca caagtagtga tcaacatcca     840
agtcaacagc aagagattct tcaatggttt gggagcagta actttcagac agaagcaatc     900
aacgatatgt tcataaacaa caacaacaac atagtgaatc ttgagaccat cgagaacaca     960
aaagtctatg agagacgcctc agtagccgga gccgctgtcc gagcagcttt gggcggaggg    1020
acaacgagta catcggcgga tcaaagtaca ataagttggg aggatataac ttctctagtt    1080
aattccgaag atgcaagtta cttcaatgcg ccaaatcatg tgtaa                    1125

<210> SEQ ID NO 10
<211> LENGTH: 374
<212> TYPE: PRT
<213> ORGANISM: Arabidopsis thaliana
```

<400> SEQUENCE: 10

```
Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Asn Ser
            20                  25                  30

Gly Thr Gly Gly Asn Trp Ile Ala Leu Pro Gln Lys Ile Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Phe Ser Glu Glu Asp Asn Ile Ile Cys
65                  70                  75                  80

Asn Leu Tyr Val Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Asn Lys Gln Arg Lys Glu Phe Gln Glu Ala
        115                 120                 125

Arg Met Lys Gln Glu Met Val Met Met Lys Arg Gln Gln Gln Gly Gln
    130                 135                 140

Gly Gln Gly Gln Ser Asn Gly Ser Thr Asp Leu Tyr Leu Asn Asn Met
145                 150                 155                 160

Phe Gly Ser Ser Pro Trp Pro Leu Leu Pro Gln Leu Pro Pro His
                165                 170                 175

His Gln Ile Pro Leu Gly Met Met Glu Pro Thr Ser Cys Asn Tyr Tyr
            180                 185                 190

Gln Thr Thr Pro Ser Cys Asn Leu Glu Gln Lys Pro Leu Ile Thr Leu
        195                 200                 205

Lys Asn Met Val Lys Ile Glu Glu Gln Glu Arg Thr Asn Pro Asp
    210                 215                 220

His His His Gln Asp Ser Val Thr Asn Pro Phe Asp Phe Ser Phe Ser
225                 230                 235                 240

Gln Leu Leu Leu Asp Pro Asn Tyr Tyr Leu Gly Ser Gly Gly Gly
                245                 250                 255

Glu Gly Asp Phe Ala Ile Met Ser Ser Ser Thr Asn Ser Pro Leu Pro
            260                 265                 270

Asn Thr Ser Ser Asp Gln His Pro Ser Gln Gln Gln Glu Ile Leu Gln
        275                 280                 285

Trp Phe Gly Ser Ser Asn Phe Gln Thr Glu Ala Ile Asn Asp Met Phe
    290                 295                 300

Ile Asn Asn Asn Asn Ile Val Asn Leu Glu Thr Ile Glu Asn Thr
305                 310                 315                 320

Lys Val Tyr Gly Asp Ala Ser Val Ala Gly Ala Val Arg Ala Ala
                325                 330                 335

Leu Gly Gly Gly Thr Thr Ser Thr Ser Ala Asp Gln Ser Thr Ile Ser
            340                 345                 350

Trp Glu Asp Ile Thr Ser Leu Val Asn Ser Glu Asp Ala Ser Tyr Phe
        355                 360                 365

Asn Ala Pro Asn His Val
    370
```

<210> SEQ ID NO 11
<211> LENGTH: 1164
<212> TYPE: DNA

<213> ORGANISM: Arabidopsis thaliana

<400> SEQUENCE: 11

```
atgcagcaac caccgtcaaa cgccgccgga gctggacaga taccatcagg acaacagcat    60
ttgtggatga tgatgcaaca gcagcagcag cagcagcaga tgcagttgtc tgcggcgcca   120
ctaggtcaac atcagtacgg tattggatct cagaatccag atccgctagc gatgttaag    180
tcgttgtgga tcggagactt gcagcaatgg atggacgaga actacatcat gagcgtcttt   240
gctcagtctg gcgaggctac atcagctaaa gtcattcgta taagctgacg ggacaatct    300
gaaggttatg gattcattga gttcgtcagc cactctgtag cagagcgggt tttgcagact   360
tacaatggtg ctcccatgcc gagcactgaa cagacgttta ggctcaactg gctcaggct    420
ggggctggag agaaacgatt ccagactgaa gggcctgacc ataccatttt cgtaggtgac   480
ttggcacctg aggtgactga ctatatgctc tcggacacat tcaagaatgt gtatgggtct   540
gtcaaagggg ctaaagttgt gcttgacagg accactggaa ggtccaaggg gtatgggttt   600
gttaggtttg cggatgaaaa tgagcagatg cgtgccatga ctgaaatgaa tggtcaatac   660
tgctcgacaa ggcctatgcg tattggtccg gctgccaata agaatgctct tccgatgcaa   720
ccagctatgt atcaaaacac tcaaggagca atgctggag ataatgatcc taataacaca    780
acaattttg ttggaggtct ggatgctaat gttacagacg atgaattaaa gtcaattttt    840
ggtcaatttg gtgaacttct tcatgtgaaa ataccctccag gaaaacgttg tggattcgtt   900
caatatgcca acaaggcgtc tgcagagcat gcactttcgg tgctgaatgg aacacaatta   960
ggtggacaaa gcatccgtct ttcgtgggga cgtagtccaa caagcagtc tgatcaagcg  1020
caatggaacg gtggtggata ctatggatac cctccacagc cacagggcgg ctatggttat  1080
gcagctcaac caccaactca agaccctaat gcgtactatg gtggttacac tggctatggc  1140
aactatcagc agcaacgtca gtga                                          1164
```

<210> SEQ ID NO 12
<211> LENGTH: 387
<212> TYPE: PRT
<213> ORGANISM: Arabidopsis thaliana

<400> SEQUENCE: 12

```
Met Gln Gln Pro Pro Ser Asn Ala Ala Gly Ala Gly Gln Ile Pro Ser
 1               5                  10                  15

Gly Gln Gln His Leu Trp Met Met Met Gln Gln Gln Gln Gln Gln Gln
            20                  25                  30

Gln Met Gln Leu Ser Ala Ala Pro Leu Gly Gln His Gln Tyr Gly Ile
        35                  40                  45

Gly Ser Gln Asn Pro Gly Ser Ala Ser Asp Val Lys Ser Leu Trp Ile
    50                  55                  60

Gly Asp Leu Gln Gln Trp Met Asp Glu Asn Tyr Ile Met Ser Val Phe
65                  70                  75                  80

Ala Gln Ser Gly Glu Ala Thr Ser Ala Lys Val Ile Arg Asn Lys Leu
                85                  90                  95

Thr Gly Gln Ser Glu Gly Tyr Gly Phe Ile Glu Phe Val Ser His Ser
            100                 105                 110

Val Ala Glu Arg Val Leu Gln Thr Tyr Asn Gly Ala Pro Met Pro Ser
        115                 120                 125

Thr Glu Gln Thr Phe Arg Leu Asn Trp Ala Gln Ala Gly Ala Gly Glu
    130                 135                 140
```

```
Lys Arg Phe Gln Thr Glu Gly Pro Asp His Thr Ile Phe Val Gly Asp
145                 150                 155                 160

Leu Ala Pro Glu Val Thr Asp Tyr Met Leu Ser Asp Thr Phe Lys Asn
            165                 170                 175

Val Tyr Gly Ser Val Lys Gly Ala Lys Val Val Leu Asp Arg Thr Thr
        180                 185                 190

Gly Arg Ser Lys Gly Tyr Gly Phe Val Arg Phe Ala Asp Glu Asn Glu
            195                 200                 205

Gln Met Arg Ala Met Thr Glu Met Asn Gly Gln Tyr Cys Ser Thr Arg
    210                 215                 220

Pro Met Arg Ile Gly Pro Ala Ala Asn Lys Asn Ala Leu Pro Met Gln
225                 230                 235                 240

Pro Ala Met Tyr Gln Asn Thr Gln Gly Ala Asn Ala Gly Asp Asn Asp
            245                 250                 255

Pro Asn Asn Thr Thr Ile Phe Val Gly Gly Leu Asp Ala Asn Val Thr
        260                 265                 270

Asp Asp Glu Leu Lys Ser Ile Phe Gly Gln Phe Gly Glu Leu Leu His
    275                 280                 285

Val Lys Ile Pro Pro Gly Lys Arg Cys Gly Phe Val Gln Tyr Ala Asn
290                 295                 300

Lys Ala Ser Ala Glu His Ala Leu Ser Val Leu Asn Gly Thr Gln Leu
305                 310                 315                 320

Gly Gly Gln Ser Ile Arg Leu Ser Trp Gly Arg Ser Pro Asn Lys Gln
            325                 330                 335

Ser Asp Gln Ala Gln Trp Asn Gly Gly Tyr Tyr Gly Tyr Pro Pro
    340                 345                 350

Gln Pro Gln Gly Gly Tyr Gly Tyr Ala Ala Gln Pro Pro Thr Gln Asp
    355                 360                 365

Pro Asn Ala Tyr Tyr Gly Gly Tyr Thr Gly Tyr Gly Asn Tyr Gln Gln
    370                 375                 380

Gln Arg Gln
385

<210> SEQ ID NO 13
<211> LENGTH: 1218
<212> TYPE: DNA
<213> ORGANISM: Arabidopsis thaliana

<400> SEQUENCE: 13
atgatgcagc agccaccacc cggaggtatc cttccacatc acgctcctcc tccttctgcg      60
caacaacagt acggttacca acaaccttac gggattgctg agctgctcc accaccacca     120 cagatgtgga atcctcaagc ggcggcgccg ccatcagttc agcctacgac cgctgacgag     180
atccggactc tttggatcgg ggacttacag tattggatgg atgagaattt cctctacggt     240
tgctttgctc ataccggaga gatggttct gctaaagtga tcgtaacaa gcaaaccggt       300 caagttgaag gatacggttt cattgaattc gcatctcatg ctgctgctga aagagttcta     360
caaacattca acaacgctcc tatcccgagc tttcctgatc agctctttag actgaactgg     420
gcatcattga gttcaggaga taaacgagac gattcaccgg actacacgat atttgtcggt     480
gatctggctg ctgatgttac ggattatatc ttacttgaga cgttcagagc ctcttatccg     540
tcagtgaagg gtgcaaaggt tgttattgac agagtcactg gacgtacaaa aggatatggg     600
tttgttaggt ttctgatga agtgaacag atccgtgcta tgacggagat gaatggcgtt       660
ccttgttcta ctagacctat gagaattggt cccgctgcta gcaagaaagg tgtaactggt     720
```

```
caaagagatt cataccagag ctctgctgca ggggtaacaa ctgataatga tccaaataac    780
acaactgttt tgttggtgg attagatgca tctgtcacgg atgatcatct gaagaatgtc    840
tttagccaat atggtgagat tgtgcatgtg aaaatacccg ctggaaagcg ctgtggattc    900
gttcagtttt ccgagaagag ctgtgcagag gaagctctta gaatgctgaa tggagtgcaa    960
ttaggcggaa caaccgtcag gctctcatgg ggccgaagtc cttcgaacaa acagtcgggg   1020
gatccgagcc agttttacta cggtgggtat ggacaaggac aggagcagta tgggtacacg   1080
atgcctcaag accctaatgc atattacgga ggctactctg gtgaggata cagcggtggt   1140 taccagcaga caccacaggc aggacagcaa ccaccacaac agccaccaca gcagcaacaa   1200
gtcgggttta gctactaa                                                 1218
```

<210> SEQ ID NO 14
<211> LENGTH: 405
<212> TYPE: PRT
<213> ORGANISM: Arabidopsis thaliana

<400> SEQUENCE: 14

```
Met Met Gln Gln Pro Pro Gly Gly Ile Leu Pro His His Ala Pro
1               5                   10                  15

Pro Pro Ser Ala Gln Gln Gln Tyr Gly Tyr Gln Gln Pro Tyr Gly Ile
            20                  25                  30

Ala Gly Ala Ala Pro Pro Pro Gln Met Trp Asn Pro Gln Ala Ala
        35                  40                  45

Ala Pro Pro Ser Val Gln Pro Thr Thr Ala Asp Glu Ile Arg Thr Leu
    50                  55                  60

Trp Ile Gly Asp Leu Gln Tyr Trp Met Asp Glu Asn Phe Leu Tyr Gly
65                  70                  75                  80

Cys Phe Ala His Thr Gly Glu Met Val Ser Ala Lys Val Ile Arg Asn
                85                  90                  95

Lys Gln Thr Gly Gln Val Glu Gly Tyr Gly Phe Ile Glu Phe Ala Ser
            100                 105                 110

His Ala Ala Ala Glu Arg Val Leu Gln Thr Phe Asn Asn Ala Pro Ile
        115                 120                 125

Pro Ser Phe Pro Asp Gln Leu Phe Arg Leu Asn Trp Ala Ser Leu Ser
    130                 135                 140

Ser Gly Asp Lys Arg Asp Asp Ser Pro Asp Tyr Thr Ile Phe Val Gly
145                 150                 155                 160

Asp Leu Ala Ala Asp Val Thr Asp Tyr Ile Leu Leu Glu Thr Phe Arg
                165                 170                 175

Ala Ser Tyr Pro Ser Val Lys Gly Ala Lys Val Val Ile Asp Arg Val
            180                 185                 190

Thr Gly Arg Thr Lys Gly Tyr Gly Phe Val Arg Phe Ser Asp Glu Ser
        195                 200                 205

Glu Gln Ile Arg Ala Met Thr Glu Met Asn Gly Val Pro Cys Ser Thr
    210                 215                 220

Arg Pro Met Arg Ile Gly Pro Ala Ala Ser Lys Lys Gly Val Thr Gly
225                 230                 235                 240

Gln Arg Asp Ser Tyr Gln Ser Ser Ala Ala Gly Val Thr Thr Asp Asn
                245                 250                 255

Asp Pro Asn Asn Thr Thr Val Phe Val Gly Gly Leu Asp Ala Ser Val
            260                 265                 270

Thr Asp Asp His Leu Lys Asn Val Phe Ser Gln Tyr Gly Glu Ile Val
```

```
                275                 280                 285
His Val Lys Ile Pro Ala Gly Lys Arg Cys Gly Phe Val Gln Phe Ser
    290                 295                 300
Glu Lys Ser Cys Ala Glu Glu Ala Leu Arg Met Leu Asn Gly Val Gln
305                 310                 315                 320
Leu Gly Gly Thr Thr Val Arg Leu Ser Trp Gly Arg Ser Pro Ser Asn
                325                 330                 335
Lys Gln Ser Gly Asp Pro Ser Gln Phe Tyr Tyr Gly Tyr Gly Tyr Gln
                340                 345                 350
Gly Gln Glu Gln Tyr Gly Tyr Thr Met Pro Gln Asp Pro Asn Ala Tyr
            355                 360                 365
Tyr Gly Gly Tyr Ser Gly Gly Gly Tyr Ser Gly Gly Tyr Gln Gln Thr
        370                 375                 380
Pro Gln Ala Gly Gln Gln Pro Pro Gln Gln Pro Pro Gln Gln Gln Gln
385                 390                 395                 400
Val Gly Phe Ser Tyr
                405

<210> SEQ ID NO 15
<211> LENGTH: 1248
<212> TYPE: DNA
<213> ORGANISM: Arabidopsis thaliana

<400> SEQUENCE: 15
atgatgcagc agccacctcc agcttccaac ggtgctgcaa cagggccagg gcagattcct       60
tccgaccaac aagcttacct ccagcagcag cagtcgtgga tgatgcagca ccagcagcaa      120
caacaaggtc agccgcctgc aggatggaat cagcagtctg caccgtcttc tggtcaacca      180
cagcagcagc agtatggtgg tggtggatct cagaatccag gatcagctgg tgagatccgg      240
tccctgtgga tcggtgactt gcagccatgg atggatgaga actatctcat gaacgtcttt      300
ggtcttactg gcgaggctac agcagctaaa gttattcgca taaacagaa cggatattca       360 gaaggttatg gctttattga gtttgtgaac catgctacag ctgagaggaa tttacagact      420
tacaatggtg ctccgatgcc gagcagtgag caggccttca ggttgaactg gctcagctt       480 ggagctggag agagacgcca ggctgaaggg cctgagcaca cagttttgt tggagacttg       540 gcacctgatg ttaccgacca catgcttact gaaacgttta agctgtgta ttcctctgtc       600 aagggagcta agttgtgaa tgataggact actggacggt ccaagggtta tggatttgtc       660
aggtttgcgg atgaaagtga gcagattcgt gccatgactg aaatgaatgg tcaatactgc      720
tcatcaaggc ctatgcgtac tggtcctgct gccaacaaga agcctcttac aatgcaacca      780
gcttcatatc agaacactca aggaaattca ggagaaagtg atccaactaa cacaacaatt      840
tttgttggag ctgtggatca aagtgtaaca gaagatgatt tgaagtcagt ttttggtcaa      900
tttggtgaac tagttcatgt gaaaataccc gcaggaaaac gttgcggatt gttcaatac       960 gccaataggg catgtgctga gcaagcactt tctgtgttga acggaacaca acttggggga     1020
caaagcattc gtctttcatg gggtcgcagt ccttccaaca aacagactca acctgatcaa     1080
gcccagtatg gtggtggtgg aggatactat gggtatcctc ctcaaggata tgaagcatac     1140
ggatatgcac tcctcctca ggaccctaac gcctactacg gtggttatgc tggggcggc       1200 tatggaaact accagcagcc tggtggatac cagcagcaac agcagtga                  1248

<210> SEQ ID NO 16
<211> LENGTH: 415
```

<212> TYPE: PRT
<213> ORGANISM: Arabidopsis thaliana

<400> SEQUENCE: 16

```
Met Met Gln Gln Pro Pro Ala Ser Asn Gly Ala Ala Thr Gly Pro
1               5                   10                  15

Gly Gln Ile Pro Ser Asp Gln Gln Ala Tyr Leu Gln Gln Gln Ser
                20                  25                  30

Trp Met Met Gln His Gln Gln Gln Gln Gly Gln Pro Pro Ala Gly
            35                  40                  45

Trp Asn Gln Gln Ser Ala Pro Ser Ser Gly Pro Gln Gln Gln Gln
50                  55                  60

Tyr Gly Gly Gly Ser Gln Asn Pro Gly Ser Ala Gly Glu Ile Arg
65                  70                  75                  80

Ser Leu Trp Ile Gly Asp Leu Gln Pro Trp Met Asp Glu Asn Tyr Leu
                85                  90                  95

Met Asn Val Phe Gly Leu Thr Gly Glu Ala Thr Ala Ala Lys Val Ile
                100                 105                 110

Arg Asn Lys Gln Asn Gly Tyr Ser Glu Gly Tyr Gly Phe Ile Glu Phe
            115                 120                 125

Val Asn His Ala Thr Ala Glu Arg Asn Leu Gln Thr Tyr Asn Gly Ala
            130                 135                 140

Pro Met Pro Ser Ser Glu Gln Ala Phe Arg Leu Asn Trp Ala Gln Leu
145                 150                 155                 160

Gly Ala Gly Glu Arg Arg Gln Ala Glu Gly Pro Glu His Thr Val Phe
                165                 170                 175

Val Gly Asp Leu Ala Pro Asp Val Thr Asp His Met Leu Thr Glu Thr
                180                 185                 190

Phe Lys Ala Val Tyr Ser Ser Val Lys Gly Ala Lys Val Val Asn Asp
            195                 200                 205

Arg Thr Thr Gly Arg Ser Lys Gly Tyr Gly Phe Val Arg Phe Ala Asp
210                 215                 220

Glu Ser Glu Gln Ile Arg Ala Met Thr Glu Met Asn Gly Gln Tyr Cys
225                 230                 235                 240

Ser Ser Arg Pro Met Arg Thr Gly Pro Ala Ala Asn Lys Lys Pro Leu
                245                 250                 255

Thr Met Gln Pro Ala Ser Tyr Gln Asn Thr Gln Gly Asn Ser Gly Glu
            260                 265                 270

Ser Asp Pro Thr Asn Thr Thr Ile Phe Val Gly Ala Val Asp Gln Ser
            275                 280                 285

Val Thr Glu Asp Asp Leu Lys Ser Val Phe Gly Gln Phe Gly Glu Leu
            290                 295                 300

Val His Val Lys Ile Pro Ala Gly Lys Arg Cys Gly Phe Val Gln Tyr
305                 310                 315                 320

Ala Asn Arg Ala Cys Ala Glu Gln Ala Leu Ser Val Leu Asn Gly Thr
                325                 330                 335

Gln Leu Gly Gly Gln Ser Ile Arg Leu Ser Trp Gly Arg Ser Pro Ser
            340                 345                 350

Asn Lys Gln Thr Gln Pro Asp Gln Ala Gln Tyr Gly Gly Gly Gly
            355                 360                 365

Tyr Tyr Gly Tyr Pro Pro Gln Gly Tyr Glu Ala Tyr Gly Tyr Ala Pro
            370                 375                 380

Pro Pro Gln Asp Pro Asn Ala Tyr Tyr Gly Gly Tyr Ala Gly Gly
385                 390                 395                 400
```

Tyr Gly Asn Tyr Gln Gln Pro Gly Gly Tyr Gln Gln Gln Gln
                405                 410                 415

<210> SEQ ID NO 17
<211> LENGTH: 1278
<212> TYPE: DNA
<213> ORGANISM: Arabidopsis thaliana

<400> SEQUENCE: 17

```
atggcgatga tgcatcctcc gcagccgccg caaggctcct atcaccatcc tcagacgctc      60
gaagaagttc gaactctttg gattggtgat ttgcagtact gggtcgacga aaattacctc     120
acttcctgct tctcccaaac cggcgagctc gtttctgtca aggtaatacg taacaagatc     180
acgggacagc cagaggggta tggttttata gagtttatat ctcatgcagc agcagagaga     240
actctgcaga cgtacaatgg gacacagatg cctggaactg agttaacttt tcggttaaat     300
tgggcttctt ttggttcagg acagaaagtt gatgctggac ctgatcattc tatctttgtt     360
ggagatttag cacctgatgt tacagattat cttcttcaag agacattccg tgttcattat     420
tcttctgtta gaggtgccaa ggttgttact gatccaagta ctggacgatc aaagggttat     480
ggatttgtaa aatttgcaga ggaaagtgaa aggaatcggg ctatggctga atgaatggt      540
ttgtattgct caacaaggcc tatgcgtatt agcgcagcaa cacctaaaaa aaacgtcggt     600
gtgcagcaac aatatgtcac caaagctgtt tacccagtta cagtcccatc tgcagttgct     660
gcaccagtcc aagcatacgt tgctccacct gaaagtgatg tcacctgtac aacgatttca     720
gttgccaatt tggaccaaaa tgttacagag gaagagctga agaaagcatt ctcccaatta     780
ggagaggtta tttatgtcaa aatacctgca caaagggat atggttatgt tcaattcaaa     840
accaggcctt ctgcagaaga agctgttcaa gaatgcagg acaagtgat tggtcaacaa       900
gcagttcgca tctcttggag taaaaatcca ggacaggat gttgggttac acaagcagat      960
ccgaatcagt ggaatgggta ttatggttat gggcaaggct atgatgcata tgcttatggg    1020
gcaactcaag atccatccgt gtacgcatat ggtggatatg ctatcccca gtatccgcaa      1080
cagggagagg gtacacaaga catttcgaac tctgcggcgg gtggagtagc aggtgcagag    1140
caagagttgt atgatcctct ggccactcct gatgtagaca agttaaatgc tgcttacctt    1200
tcggttcatg caagtgccat attaggaagg ccaatgtggc agcggacctc atcgctcaca    1260
tcacaattgg gcaaatga                                                   1278
```

<210> SEQ ID NO 18
<211> LENGTH: 425
<212> TYPE: PRT
<213> ORGANISM: Arabidopsis thaliana

<400> SEQUENCE: 18

Met Ala Met Met His Pro Pro Gln Pro Pro Gln Gly Ser Tyr His His
1               5                   10                  15

Pro Gln Thr Leu Glu Glu Val Arg Thr Leu Trp Ile Gly Asp Leu Gln
                20                  25                  30

Tyr Trp Val Asp Glu Asn Tyr Leu Thr Ser Cys Phe Ser Gln Thr Gly
            35                  40                  45

Glu Leu Val Ser Val Lys Val Ile Arg Asn Lys Ile Thr Gly Gln Pro
        50                  55                  60

Glu Gly Tyr Gly Phe Ile Glu Phe Ile Ser His Ala Ala Ala Glu Arg
65                  70                  75                  80

```
Thr Leu Gln Thr Tyr Asn Gly Thr Gln Met Pro Gly Thr Glu Leu Thr
                 85                  90                  95

Phe Arg Leu Asn Trp Ala Ser Phe Gly Ser Gly Gln Lys Val Asp Ala
            100                 105                 110

Gly Pro Asp His Ser Ile Phe Val Gly Asp Leu Ala Pro Asp Val Thr
        115                 120                 125

Asp Tyr Leu Leu Gln Glu Thr Phe Arg Val His Tyr Ser Ser Val Arg
    130                 135                 140

Gly Ala Lys Val Val Thr Asp Pro Ser Thr Gly Arg Ser Lys Gly Tyr
145                 150                 155                 160

Gly Phe Val Lys Phe Ala Glu Glu Ser Glu Arg Asn Arg Ala Met Ala
                165                 170                 175

Glu Met Asn Gly Leu Tyr Cys Ser Thr Arg Pro Met Arg Ile Ser Ala
            180                 185                 190

Ala Thr Pro Lys Lys Asn Val Gly Val Gln Gln Gln Tyr Val Thr Lys
        195                 200                 205

Ala Val Tyr Pro Val Thr Val Pro Ser Ala Val Ala Ala Pro Val Gln
    210                 215                 220

Ala Tyr Val Ala Pro Pro Glu Ser Asp Val Thr Cys Thr Thr Ile Ser
225                 230                 235                 240

Val Ala Asn Leu Asp Gln Asn Val Thr Glu Glu Leu Lys Lys Ala
                245                 250                 255

Phe Ser Gln Leu Gly Glu Val Ile Tyr Val Lys Ile Pro Ala Thr Lys
            260                 265                 270

Gly Tyr Gly Tyr Val Gln Phe Lys Thr Arg Pro Ser Ala Glu Glu Ala
        275                 280                 285

Val Gln Arg Met Gln Gly Gln Val Ile Gly Gln Gln Ala Val Arg Ile
    290                 295                 300

Ser Trp Ser Lys Asn Pro Gly Gln Asp Gly Trp Val Thr Gln Ala Asp
305                 310                 315                 320

Pro Asn Gln Trp Asn Gly Tyr Tyr Gly Tyr Gly Gln Gly Tyr Asp Ala
                325                 330                 335

Tyr Ala Tyr Gly Ala Thr Gln Asp Pro Ser Val Tyr Ala Tyr Gly Gly
            340                 345                 350

Tyr Gly Tyr Pro Gln Tyr Pro Gln Gln Gly Glu Gly Thr Gln Asp Ile
        355                 360                 365

Ser Asn Ser Ala Ala Gly Gly Val Ala Gly Ala Glu Gln Glu Leu Tyr
    370                 375                 380

Asp Pro Leu Ala Thr Pro Asp Val Asp Lys Leu Asn Ala Ala Tyr Leu
385                 390                 395                 400

Ser Val His Ala Ser Ala Ile Leu Gly Arg Pro Met Trp Gln Arg Thr
                405                 410                 415

Ser Ser Leu Thr Ser Gln Leu Gly Lys
            420                 425

<210> SEQ ID NO 19
<211> LENGTH: 1338
<212> TYPE: DNA
<213> ORGANISM: Arabidopsis thaliana

<400> SEQUENCE: 19
atgcagacac caaacaacaa cggttcaaca gattcagtgt taccaccaac atcagccgga      60
acaacaccac caccaccgtt gcagcaatca acaccaccac cgcagcagca acaacaacaa     120
cagtggcaac aacaacaaca atggatggct gcgatgcagc aatacccctgc agctgctatg    180
```

-continued

```
gctatgatgc aacaacaaca gatgatgatg tatcctcacc ctcaatacgc tccttacaat    240
caagctgctt atcaacagca tcctcagttt caatacgctg cttatcaaca gcagcagcag    300
caacatcacc agagtcagca gcagccacgc ggtggatctg gtggtgatga tgtcaagact    360
ctttggcttg gtgatcttct tcattggatg gatgagactt atctccatac ctgtttctct    420
cacaccaatg aggtttcttc tgtgaaagtt atacgcaaca agcaaacttg tcaatctgaa    480
ggatatgggt ttgttgagtt ctttcacgt tcagcagctg aggaagctct tcagagcttt    540
agcggtgtta caatgccgaa cgcggaacag cctttccgtt taaactgggc atctttcagt    600
actggtgaga aagagcatc agagaatggt cctgacctat ccatatttgt tggagatttg    660
gctccagatg tgagtgatgc tgtcttgctt gagacttttg ctggtagata tccatctgtc    720
aaaggtgcta agttgtgat tgattccaac actgggcgtt ccaaaggtta cgggtttgtt    780
aggtttggtg atgagaatga gcgatcaaga gctatgacag aaatgaatgg tgctttctgt    840
tcaagcaggc aaatgcgtgt tggtatcgca accccgaaaa gggctgctgc ttacggccaa    900
caaaatggtt cacaagctct tacacttgct ggtggacatg gagggaatgg ttcaatgtct    960
gatggagaat caaataactc aacaatattt gttggcggtc ttgatgctga tgttactgaa   1020
gaagacctca tgcaacctt ttccgatttt ggggaggttg tttcagtgaa gatcccagta   1080
gggaaaggat gtggctttgt ccaatttgct aacaggcaaa gtgctgagga agccatcggg   1140
aacttgaacg ggacagtcat tgggaagaac actgtccgcc tttcatgggg aagaagcccc   1200
aacaaacagt ggagaagtga ctctggcaac caatggaatg aggatattc aagaggtcaa   1260 ggatacaaca atggatatgc caatcaggac tcaaacatgt acgctactgc agcggctgca   1320
gtcccgggag cttcttga                                                 1338
```

<210> SEQ ID NO 20
<211> LENGTH: 445
<212> TYPE: PRT
<213> ORGANISM: Arabidopsis thaliana

<400> SEQUENCE: 20

```
Met Gln Thr Pro Asn Asn Gly Ser Thr Asp Ser Val Leu Pro Pro
1               5                   10                  15

Thr Ser Ala Gly Thr Thr Pro Pro Pro Leu Gln Gln Ser Thr Pro
            20                  25                  30

Pro Pro Gln Gln Gln Gln Gln Gln Trp Gln Gln Gln Gln Trp
        35                  40                  45

Met Ala Ala Met Gln Gln Tyr Pro Ala Ala Ala Met Ala Met Gln
    50                  55                  60

Gln Gln Gln Met Met Met Tyr Pro His Pro Gln Tyr Ala Pro Tyr Asn
65                  70                  75                  80

Gln Ala Ala Tyr Gln Gln His Pro Gln Phe Gln Tyr Ala Ala Tyr Gln
                85                  90                  95

Gln Gln Gln Gln Gln His His Gln Ser Gln Gln Pro Arg Gly Gly
            100                 105                 110

Ser Gly Gly Asp Asp Val Lys Thr Leu Trp Val Gly Asp Leu Leu His
            115                 120                 125

Trp Met Asp Glu Thr Tyr Leu His Thr Cys Phe Ser His Thr Asn Glu
    130                 135                 140

Val Ser Ser Val Lys Val Ile Arg Asn Lys Gln Thr Cys Gln Ser Glu
145                 150                 155                 160
```

```
Gly Tyr Gly Phe Val Glu Phe Leu Ser Arg Ser Ala Ala Glu Glu Ala
                165                 170                 175

Leu Gln Ser Phe Ser Gly Val Thr Met Pro Asn Ala Glu Gln Pro Phe
            180                 185                 190

Arg Leu Asn Trp Ala Ser Phe Ser Thr Gly Lys Arg Ala Ser Glu
        195                 200                 205

Asn Gly Pro Asp Leu Ser Ile Phe Val Gly Asp Leu Ala Pro Asp Val
    210                 215                 220

Ser Asp Ala Val Leu Leu Glu Thr Phe Ala Gly Arg Tyr Pro Ser Val
225                 230                 235                 240

Lys Gly Ala Lys Val Ile Asp Ser Asn Thr Gly Arg Ser Lys Gly
                245                 250                 255

Tyr Gly Phe Val Arg Phe Gly Asp Glu Asn Glu Arg Ser Arg Ala Met
                260                 265                 270

Thr Glu Met Asn Gly Ala Phe Cys Ser Ser Arg Gln Met Arg Val Gly
            275                 280                 285

Ile Ala Thr Pro Lys Arg Ala Ala Tyr Gly Gln Gln Asn Gly Ser
        290                 295                 300

Gln Ala Leu Thr Leu Ala Gly Gly His Gly Gly Asn Gly Ser Met Ser
305                 310                 315                 320

Asp Gly Glu Ser Asn Asn Ser Thr Ile Phe Val Gly Gly Leu Asp Ala
                325                 330                 335

Asp Val Thr Glu Glu Asp Leu Met Gln Pro Phe Ser Asp Phe Gly Glu
            340                 345                 350

Val Val Ser Val Lys Ile Pro Val Gly Lys Gly Cys Gly Phe Val Gln
        355                 360                 365

Phe Ala Asn Arg Gln Ser Ala Glu Glu Ala Ile Gly Asn Leu Asn Gly
    370                 375                 380

Thr Val Ile Gly Lys Asn Thr Val Arg Leu Ser Trp Gly Arg Ser Pro
385                 390                 395                 400

Asn Lys Gln Trp Arg Ser Asp Ser Gly Asn Gln Trp Asn Gly Gly Tyr
                405                 410                 415

Ser Arg Gly Gln Gly Tyr Asn Asn Gly Tyr Ala Asn Gln Asp Ser Asn
            420                 425                 430

Met Tyr Ala Thr Ala Ala Ala Val Pro Gly Ala Ser
        435                 440                 445

<210> SEQ ID NO 21
<211> LENGTH: 1308
<212> TYPE: DNA
<213> ORGANISM: Arabidopsis thaliana

<400> SEQUENCE: 21
atgcagacaa ccaacggctc agattcgacg ttggcaactt ccggagccac accgccgaat      60
caacaaaccc ctcctccacc tcagcagtgg cagcagcagc aacagcaaca gcaacagtgg     120
atggctgcca tgcaatatcc accagcggcg gcgatgatga tgatgcagca gcaacagatg     180
ctgatgtatc ctcatcaata tgttccgtat aatcaaggtc cttatcagca gcatcatcct     240
cagcttcacc aatacgggtc ttatcaacag caccagcacc agcaacacaa ggctattgac     300
cgtggatctg gagatgatgt caagactctt tgggttggtg atcttcttca ttggatggat     360
gagacttatc tccattcttg ctttttctca accggcgagg tttcttctgt gaaagttata     420
cgtaacaagc tcacttctca atcagaaggg tatgggtttg ttgagtttct ttcacgtgct     480
gcagctgaag aagttcttca gaactatagt ggttcagtga tgccaaactc ggaccaaccc     540
```

| | | | | |
|---|---|---|---|---|
| ttccgtataa | actgggcatc | ttttagtact | ggtgaaaaaa | gagcagtgga | aaatggtcca | 600 |
| gacctatctg | tttttgtggg | agacttgtct | ccagatgtca | ctgacgtttt | attgcatgag | 660 |
| acctttctg | atagatatcc | ttctgtcaaa | agcgccaaag | ttgtgattga | ttccaacacc | 720 |
| ggccggtcca | aaggttatgg | ttttgtgagg | ttcggtgatg | aaaatgagag | gtcaagggct | 780 |
| ttgacagaaa | tgaatggagc | ttactgttcg | aacaggcaaa | tgcgtgtagg | tattgcaact | 840 |
| cccaaaagag | cgattgctaa | tcagcaacaa | cattcttcac | aagctgtgat | tctggctggt | 900 |
| ggacatggat | caaatggttc | catgggttat | ggctcgcagt | ctgatggcga | atcaactaac | 960 |
| gcaacaatat | tgttggcgg | cattgaccct | gatgttattg | atgaagacct | cagacaacct | 1020 |
| ttttcccagt | ttggagaggt | tgtttcagtg | aagatcccag | tagggaaagg | atgtggatt | 1080 |
| gtccaatttg | ctgacaggaa | gagtgctgaa | gatgctatcg | agagtttgaa | cgggacagtc | 1140 |
| atcggcaaga | acactgtcag | actctcctgg | ggacgaagcc | caaacaagca | gtggagagga | 1200 |
| gactcagggc | agcagtggaa | tgaggatac | tcacgaggac | atggttacaa | caatggagga | 1260 |
| ggatatgcta | accaccacga | ctccaacaac | tatcatgggg | agaattga | | 1308 |

```
<210> SEQ ID NO 22
<211> LENGTH: 435
<212> TYPE: PRT
<213> ORGANISM: Arabidopsis thaliana

<400> SEQUENCE: 22
```

Met Gln Thr Thr Asn Gly Ser Asp Ser Thr Leu Ala Thr Ser Gly Ala
1               5                   10                  15

Thr Pro Pro Asn Gln Gln Thr Pro Pro Pro Gln Gln Trp Gln Gln
            20                  25                  30

Gln Gln Gln Gln Gln Gln Gln Trp Met Ala Ala Met Gln Tyr Pro Pro
        35                  40                  45

Ala Ala Ala Met Met Met Met Gln Gln Gln Met Leu Met Tyr Pro
    50                  55                  60

His Gln Tyr Val Pro Tyr Asn Gln Gly Pro Tyr Gln Gln His His Pro
65                  70                  75                  80

Gln Leu His Gln Tyr Gly Ser Tyr Gln Gln His Gln His Gln Gln His
                85                  90                  95

Lys Ala Ile Asp Arg Gly Ser Gly Asp Asp Val Lys Thr Leu Trp Val
            100                 105                 110

Gly Asp Leu Leu His Trp Met Asp Glu Thr Tyr Leu His Ser Cys Phe
        115                 120                 125

Ser His Thr Gly Glu Val Ser Ser Val Lys Val Ile Arg Asn Lys Leu
    130                 135                 140

Thr Ser Gln Ser Glu Gly Tyr Gly Phe Val Glu Phe Leu Ser Arg Ala
145                 150                 155                 160

Ala Ala Glu Glu Val Leu Gln Asn Tyr Ser Gly Ser Val Met Pro Asn
                165                 170                 175

Ser Asp Gln Pro Phe Arg Ile Asn Trp Ala Ser Phe Ser Thr Gly Glu
            180                 185                 190

Lys Arg Ala Val Glu Asn Gly Pro Asp Leu Ser Val Phe Val Gly Asp
        195                 200                 205

Leu Ser Pro Asp Val Thr Asp Val Leu Leu His Glu Thr Phe Ser Asp
    210                 215                 220

Arg Tyr Pro Ser Val Lys Ser Ala Lys Val Val Ile Asp Ser Asn Thr
225                 230                 235                 240

```
Gly Arg Ser Lys Gly Tyr Gly Phe Val Arg Phe Gly Asp Glu Asn Glu
                245                 250                 255

Arg Ser Arg Ala Leu Thr Glu Met Asn Gly Ala Tyr Cys Ser Asn Arg
            260                 265                 270

Gln Met Arg Val Gly Ile Ala Thr Pro Lys Arg Ala Ile Ala Asn Gln
        275                 280                 285

Gln Gln His Ser Ser Gln Ala Val Ile Leu Ala Gly Gly His Gly Ser
    290                 295                 300

Asn Gly Ser Met Gly Tyr Gly Ser Gln Ser Asp Gly Glu Ser Thr Asn
305                 310                 315                 320

Ala Thr Ile Phe Val Gly Gly Ile Asp Pro Asp Val Ile Asp Glu Asp
                325                 330                 335

Leu Arg Gln Pro Phe Ser Gln Phe Gly Glu Val Val Ser Val Lys Ile
            340                 345                 350

Pro Val Gly Lys Gly Cys Gly Phe Val Gln Phe Ala Asp Arg Lys Ser
        355                 360                 365

Ala Glu Asp Ala Ile Glu Ser Leu Asn Gly Thr Val Ile Gly Lys Asn
    370                 375                 380

Thr Val Arg Leu Ser Trp Gly Arg Ser Pro Asn Lys Gln Trp Arg Gly
385                 390                 395                 400

Asp Ser Gly Gln Gln Trp Asn Gly Gly Tyr Ser Arg Gly His Gly Tyr
                405                 410                 415

Asn Asn Gly Gly Gly Tyr Ala Asn His His Asp Ser Asn Asn Tyr His
            420                 425                 430

Gly Glu Asn
        435

<210> SEQ ID NO 23
<211> LENGTH: 1299
<212> TYPE: DNA
<213> ORGANISM: Arabidopsis thaliana

<400> SEQUENCE: 23
atggcagacg tcaagattca atccgaatcc gaatcctcgg attctcatcc agtggtcgac      60
aatcaaccac ctcctccgcc tccgccgccg caacagccgg cgaaagaaga ggagaatcaa     120
ccaaaaacat ctccgactcc gccgccacac tggatgcggt atccaccaac ggtgataatc     180
cctcatcaga tgatgtacgc gccgccgccg ttcccacctt atcatcagta tccgaatcac     240
caccaccttc accatcaatc tcgtggtaat aagcatcaaa acgcttttaa tggtgagaat     300
aaaaccatat gggttggtga tttgcatcac tggatggatg aggcttatct taattcttct     360
tttgcttccg gcgacgagag agagattgtt tcggtgaagg tgattcgtaa taagaacaat     420
ggtttatcag aaggatatgg atttgtggag tttgagtccc atgatgtagc tgataaggtt     480
ttgcgggagt ttaacgggac gactatgcca atactgacc aacctttcg tttgaactgg      540 gctagtttta gcaccggtga gaagcggtta gagaacaatg gacctgatct ctctattttc     600 gtggggatt tgtcaccaga tgtttcggat aatttgttgc acgagacctt ctctgagaag     660
tatccgtcgg ttaaagctgc gaaagttgtc cttgatgcta atactggtag gtcaaagggg     720
tatgggtttg tgaggtttgg tgatgagaat gaaaggacca agcaatgac tgagatgaat      780 ggtgttaaat gttctagtag agctatgcgc atcggtcctg ctaccccgag gaagactaat     840
ggttatcaac aacaaggtgg atacatgccg aatggtacct tgacgcgtcc tgaagggac     900 ataatgaaca caacaatatt tgttggaggg cttgactcta gtgtcactga tgaagactta     960
```

```
aagcaaccct tcaatgaatt cggggaaata gtctctgtca agattcctgt tggtaaagga   1020
tgcggatttg ttcagtttgt taacagacca aatgcagagg aggctttgga gaaactaaat   1080
gggactgtaa ttggaaaaca aacagttcgg ctttcttggg acgtaatcc cgccaataag    1140 cagcctagag ataagtatgg aaaccaatgg gttgatccgt actatggagg acagttttac   1200
aatgggtatg gatacatggt acctcaacct gacccgagaa tgtatcccgc tgcaccttac   1260
tatccaatgt acggtggtca tcagcaacaa gttagctga                          1299
```

<210> SEQ ID NO 24
<211> LENGTH: 432
<212> TYPE: PRT
<213> ORGANISM: Arabidopsis thaliana

<400> SEQUENCE: 24

```
Met Ala Asp Val Lys Ile Gln Ser Glu Ser Glu Ser Ser Asp Ser His
 1               5                  10                  15

Pro Val Val Asp Asn Gln Pro Pro Pro Pro Pro Pro Gln Gln
            20                  25                  30

Pro Ala Lys Glu Glu Glu Asn Gln Pro Lys Thr Ser Pro Thr Pro Pro
        35                  40                  45

Pro His Trp Met Arg Tyr Pro Pro Thr Val Ile Ile Pro His Gln Met
    50                  55                  60

Met Tyr Ala Pro Pro Pro Phe Pro Pro Tyr His Gln Tyr Pro Asn His
65                  70                  75                  80

His His Leu His His Gln Ser Arg Gly Asn Lys His Gln Asn Ala Phe
                85                  90                  95

Asn Gly Glu Asn Lys Thr Ile Trp Val Gly Asp Leu His His Trp Met
            100                 105                 110

Asp Glu Ala Tyr Leu Asn Ser Ser Phe Ala Ser Gly Asp Glu Arg Glu
        115                 120                 125

Ile Val Ser Val Lys Val Ile Arg Asn Lys Asn Asn Gly Leu Ser Glu
    130                 135                 140

Gly Tyr Gly Phe Val Glu Phe Glu Ser His Asp Val Ala Asp Lys Val
145                 150                 155                 160

Leu Arg Glu Phe Asn Gly Thr Thr Met Pro Asn Thr Asp Gln Pro Phe
                165                 170                 175

Arg Leu Asn Trp Ala Ser Phe Ser Thr Gly Glu Lys Arg Leu Glu Asn
            180                 185                 190

Asn Gly Pro Asp Leu Ser Ile Phe Val Gly Asp Leu Ser Pro Asp Val
        195                 200                 205

Ser Asp Asn Leu Leu His Glu Thr Phe Ser Glu Lys Tyr Pro Ser Val
    210                 215                 220

Lys Ala Ala Lys Val Val Leu Asp Ala Asn Thr Gly Arg Ser Lys Gly
225                 230                 235                 240

Tyr Gly Phe Val Arg Phe Gly Asp Glu Asn Glu Arg Thr Lys Ala Met
                245                 250                 255

Thr Glu Met Asn Gly Val Lys Cys Ser Ser Arg Ala Met Arg Ile Gly
            260                 265                 270

Pro Ala Thr Pro Arg Lys Thr Asn Gly Tyr Gln Gln Gln Gly Gly Tyr
        275                 280                 285

Met Pro Asn Gly Thr Leu Thr Arg Pro Glu Gly Asp Ile Met Asn Thr
    290                 295                 300

Thr Ile Phe Val Gly Gly Leu Asp Ser Ser Val Thr Asp Glu Asp Leu
```

```
                305                 310                 315                 320
Lys Gln Pro Phe Asn Glu Phe Gly Glu Ile Val Ser Val Lys Ile Pro
                325                 330                 335

Val Gly Lys Gly Cys Gly Phe Val Gln Phe Val Asn Arg Pro Asn Ala
                340                 345                 350

Glu Glu Ala Leu Glu Lys Leu Asn Gly Thr Val Ile Gly Lys Gln Thr
                355                 360                 365

Val Arg Leu Ser Trp Gly Arg Asn Pro Ala Asn Lys Gln Pro Arg Asp
    370                 375                 380

Lys Tyr Gly Asn Gln Trp Val Asp Pro Tyr Gly Gly Gln Phe Tyr
385                 390                 395                 400

Asn Gly Tyr Gly Tyr Met Val Pro Gln Pro Asp Pro Arg Met Tyr Pro
                405                 410                 415

Ala Ala Pro Tyr Tyr Pro Met Tyr Gly Gly His Gln Gln Gln Val Ser
                420                 425                 430

<210> SEQ ID NO 25
<211> LENGTH: 1281
<212> TYPE: DNA
<213> ORGANISM: Arabidopsis thaliana

<400> SEQUENCE: 25
atgcagaatc aaaggcttat taagcagcaa caacaacaac aacaacagca acatcaacaa        60
gctatgattc aacaagctat gatgcaacaa catccttctc tttatcatcc tggtgttatg       120
gctcctcctc agatggagcc tttaccaagt ggaaaccttc tcctggtttt tgatccaact       180
acttgccgta gtgtgtatgc tggaaacatt catacgcagg tcacagagat tcttcttcaa       240 gagattttg caagtactgg tcctattgaa agctgtaaac tcatcagaaa ggataagtca       300
tcatatggat tgttcacta ctttgatcga agatgtgcta gtatggctat aatgactctt       360
aacggaaggc atatatttgg acagccatg aaagttaatt gggcgtatgc aactggtcaa       420
agggaagata catcaagtca tttcaacatt tttgttggag atcttagtcc agaggttact       480
gatgcagcat tgtttgatag cttttctgct tttaacagct gctcggacgc aagagtaatg       540
tgggaccaga aaactggacg ctcaagaggc tttggttttg tttccttccg taatcagcag       600
gatgctcaaa ctgccataaa tgagatgaat ggtaaatggg taagtagcag acagatcaga       660
tgcaactggg cgacaaaagg tgctactttt ggcgaggaca acatagctc tgatggaaaa       720 agtgttgtag aacttactaa cggatcttca gaggatggta gagagctgtc aaatgaagat       780 gccctgaaa acaatcctca atttacaact gtctatgtag aaatctctc tccagaagta       840 actcagcttg atctacaccg tctattctat acccttggtg ctggagtgat cgaagaggtc       900
cgtgtccagc gagacaaagg gtttggtttt gtgagatata acactcatga cgaggctgct       960
cttgctattc agatgggcaa cgctcagcct ttcctcttta gcagacagat aaggtgttcc      1020
tggggaaaca aaccaactcc atcaggcaca gcctcaaacc cacttccccc accagccccg      1080
gcatcagtcc cttctctgtc tgcaatggac ctcttagcct acgagaggca actggctcta      1140
gccaagatgc atcctcaggc tcaacattct ctgaggcaag caggtcttgg agtcaatgtt      1200
gctggaggaa ctgcagctat gtatgatggt ggctatcaga atgtagctgc ggcccatcag      1260
cagctcatgt actatcagta a                                                1281

<210> SEQ ID NO 26
<211> LENGTH: 426
<212> TYPE: PRT
```

<213> ORGANISM: Arabidopsis thaliana

<400> SEQUENCE: 26

```
Met Gln Asn Gln Arg Leu Ile Lys Gln Gln Gln Gln Gln Gln Gln
1               5                   10                  15

Gln His Gln Gln Ala Met Ile Gln Gln Ala Met Met Gln Gln His Pro
            20                  25                  30

Ser Leu Tyr His Pro Gly Val Met Ala Pro Pro Gln Met Glu Pro Leu
        35                  40                  45

Pro Ser Gly Asn Leu Pro Pro Gly Phe Asp Pro Thr Thr Cys Arg Ser
    50                  55                  60

Val Tyr Ala Gly Asn Ile His Thr Gln Val Thr Glu Ile Leu Leu Gln
65                  70                  75                  80

Glu Ile Phe Ala Ser Thr Gly Pro Ile Glu Ser Cys Lys Leu Ile Arg
                85                  90                  95

Lys Asp Lys Ser Ser Tyr Gly Phe Val His Tyr Phe Asp Arg Arg Cys
            100                 105                 110

Ala Ser Met Ala Ile Met Thr Leu Asn Gly Arg His Ile Phe Gly Gln
        115                 120                 125

Pro Met Lys Val Asn Trp Ala Tyr Ala Thr Gly Gln Arg Glu Asp Thr
    130                 135                 140

Ser Ser His Phe Asn Ile Phe Val Gly Asp Leu Ser Pro Glu Val Thr
145                 150                 155                 160

Asp Ala Ala Leu Phe Asp Ser Phe Ser Ala Phe Asn Ser Cys Ser Asp
                165                 170                 175

Ala Arg Val Met Trp Asp Gln Lys Thr Gly Arg Ser Arg Gly Phe Gly
            180                 185                 190

Phe Val Ser Phe Arg Asn Gln Gln Asp Ala Gln Thr Ala Ile Asn Glu
        195                 200                 205

Met Asn Gly Lys Trp Val Ser Ser Arg Gln Ile Arg Cys Asn Trp Ala
    210                 215                 220

Thr Lys Gly Ala Thr Phe Gly Glu Asp Lys His Ser Ser Asp Gly Lys
225                 230                 235                 240

Ser Val Val Glu Leu Thr Asn Gly Ser Ser Glu Asp Gly Arg Glu Leu
                245                 250                 255

Ser Asn Glu Asp Ala Pro Glu Asn Asn Pro Gln Phe Thr Thr Val Tyr
            260                 265                 270

Val Gly Asn Leu Ser Pro Glu Val Thr Gln Leu Asp Leu His Arg Leu
        275                 280                 285

Phe Tyr Thr Leu Gly Ala Gly Val Ile Glu Glu Val Arg Val Gln Arg
    290                 295                 300

Asp Lys Gly Phe Gly Phe Val Arg Tyr Asn Thr His Asp Glu Ala Ala
305                 310                 315                 320

Leu Ala Ile Gln Met Gly Asn Ala Gln Pro Phe Leu Phe Ser Arg Gln
                325                 330                 335

Ile Arg Cys Ser Trp Gly Asn Lys Pro Thr Pro Ser Gly Thr Ala Ser
            340                 345                 350

Asn Pro Leu Pro Pro Ala Pro Ala Ser Val Pro Ser Leu Ser Ala
        355                 360                 365

Met Asp Leu Leu Ala Tyr Glu Arg Gln Leu Ala Leu Ala Lys Met His
    370                 375                 380

Pro Gln Ala Gln His Ser Leu Arg Gln Ala Gly Leu Gly Val Asn Val
385                 390                 395                 400
```

```
Ala Gly Gly Thr Ala Ala Met Tyr Asp Gly Gly Tyr Gln Asn Val Ala
                405                 410                 415

Ala Ala His Gln Gln Leu Met Tyr Tyr Gln
            420                 425

<210> SEQ ID NO 27
<211> LENGTH: 1260
<212> TYPE: DNA
<213> ORGANISM: Arabidopsis thaliana

<400> SEQUENCE: 27
atgcagaggt tgaagcagca gcagcagcag caacaagtta tgatgcagca agctcttatg      60
cagcaacagt ctctctacca tcctggtctc cttgccccgc acagataga accaatccca     120 agtggaaatc tcccccctgg ttttgatcca agtacttgcc gcagtgtgta cgttggaaac     180
atccatattc aggtgacgga acctctgctt caagaggttt ttgctggcac tggtcctgta     240
gaaagctgta aactaattag gaaagaaaag tcttcttatg ggtttgtgca ctactttgat     300
cgaagatcgg ctggtcttgc aatcctttct ctcaatggaa ggcatttgtt tgggcaacct     360
atcaaggtta actgggctta tgcgagtggc cagaggagg atacatcaag tcacttcaat     420
atatttgttg gggatttgag tccggaggtt actgatgcaa tgctgtttac ttgcttctct     480
gtctacccga cttgctcgga tgcaagagtt atgtgggatc agaaaactgg gcgttcaaga     540
ggatttggat ttgtttcctt ccgtaaccaa caggatgccc agactgcaat agatgagata     600
actgggaaat ggcttggttc caggcagata cgttgcaact gggcgacaaa gggagccact     660
tctggtgagg acaaacagag ctctgattcc aaaagcgtcg tggaacttac cagtggtgtc     720
tcggaggatg gtaaagatac tactaatggt gaagctcctg agaacaatgc tcagtacaca     780
actgtttacg tcggtaatct tgctccagag gtgtcccagg ttgatcttca ccgccacttc     840
cattcccttg gtgctggggt catagaggaa gtccgtgttc aaagagacaa aggtttcgga     900
tttgtgagat actctactca tgtagaggca gccctcgcta ttcagatggg aaacacacat     960
tcctacctta gtggcaggca aatgaagtgt tcttggggaa gcaagccaac tccagcagga    1020
acagcttcaa acccgcttcc tccaccagct cctgcaccaa tcccgggatt ctcagcgagt    1080
gatctcttgg cttacgagag gcaactagcg atgagcaaga tggcaggaat gaatccgatg    1140
atgcatcacc cgcagggaca acatgctttt aaacaagctg caatgggagc cactggttca    1200
aaccaggcaa tatatgacgg tggttaccag aacgcgcagc agctcatgta ctaccagtaa    1260

<210> SEQ ID NO 28
<211> LENGTH: 419
<212> TYPE: PRT
<213> ORGANISM: Saccharomyces cerevisiae

<400> SEQUENCE: 28

Met Gln Arg Leu Lys Gln Gln Gln Gln Gln Gln Val Met Met Gln
1               5                   10                  15

Gln Ala Leu Met Gln Gln Gln Ser Leu Tyr His Pro Gly Leu Leu Ala
            20                  25                  30

Pro Pro Gln Ile Glu Pro Ile Pro Ser Gly Asn Leu Pro Pro Gly Phe
        35                  40                  45

Asp Pro Ser Thr Cys Arg Ser Val Tyr Val Gly Asn Ile His Ile Gln
    50                  55                  60

Val Thr Glu Pro Leu Leu Gln Glu Val Phe Ala Gly Thr Gly Pro Val
65                  70                  75                  80
```

-continued

```
Glu Ser Cys Lys Leu Ile Arg Lys Glu Lys Ser Ser Tyr Gly Phe Val
             85                  90                  95
His Tyr Phe Asp Arg Arg Ser Ala Gly Leu Ala Ile Leu Ser Leu Asn
            100                 105                 110
Gly Arg His Leu Phe Gly Gln Pro Ile Lys Val Asn Trp Ala Tyr Ala
        115                 120                 125
Ser Gly Gln Arg Glu Asp Thr Ser Ser His Phe Asn Ile Phe Val Gly
    130                 135                 140
Asp Leu Ser Pro Glu Val Thr Asp Ala Met Leu Phe Thr Cys Phe Ser
145                 150                 155                 160
Val Tyr Pro Thr Cys Ser Asp Ala Arg Val Met Trp Asp Gln Lys Thr
                165                 170                 175
Gly Arg Ser Arg Gly Phe Gly Phe Val Ser Phe Arg Asn Gln Gln Asp
            180                 185                 190
Ala Gln Thr Ala Ile Asp Glu Ile Thr Gly Lys Trp Leu Gly Ser Arg
        195                 200                 205
Gln Ile Arg Cys Asn Trp Ala Thr Lys Gly Ala Thr Ser Gly Glu Asp
    210                 215                 220
Lys Gln Ser Ser Asp Ser Lys Ser Val Val Glu Leu Thr Ser Gly Val
225                 230                 235                 240
Ser Glu Asp Gly Lys Asp Thr Thr Asn Gly Glu Ala Pro Glu Asn Asn
                245                 250                 255
Ala Gln Tyr Thr Thr Val Tyr Val Gly Asn Leu Ala Pro Glu Val Ser
            260                 265                 270
Gln Val Asp Leu His Arg His Phe His Ser Leu Gly Ala Gly Val Ile
        275                 280                 285
Glu Glu Val Arg Val Gln Arg Asp Lys Gly Phe Gly Phe Val Arg Tyr
    290                 295                 300
Ser Thr His Val Glu Ala Ala Leu Ala Ile Gln Met Gly Asn Thr His
305                 310                 315                 320
Ser Tyr Leu Ser Gly Arg Gln Met Lys Cys Ser Trp Gly Ser Lys Pro
                325                 330                 335
Thr Pro Ala Gly Thr Ala Ser Asn Pro Leu Pro Pro Ala Pro Ala
            340                 345                 350
Pro Ile Pro Gly Phe Ser Ala Ser Asp Leu Leu Ala Tyr Glu Arg Gln
        355                 360                 365
Leu Ala Met Ser Lys Met Ala Gly Met Asn Pro Met Met His His Pro
    370                 375                 380
Gln Gly Gln His Ala Phe Lys Gln Ala Ala Met Gly Ala Thr Gly Ser
385                 390                 395                 400
Asn Gln Ala Ile Tyr Asp Gly Tyr Gln Asn Ala Gln Gln Leu Met
            405                 410                 415
Tyr Tyr Gln

<210> SEQ ID NO 29
<211> LENGTH: 1284
<212> TYPE: DNA
<213> ORGANISM: Arabidopsis thaliana

<400> SEQUENCE: 29
atgcagaatc cgagactgaa gcaacatcag cagcaacaac aacaacaagc tatgatgcag      60
caacaagctc tgatgcagca acactctctt taccatcctg gtgttttggc tcctcctcag     120
ttagagcctg ttccaagtgg aaaccttcct cctggttttg atcccagtac ttgccgtagc     180
```

-continued

```
gtgtatgttg gaaacatcca tacacaggtc acagagcctt tgcttcaaga gatttttaca    240
agcactggcc ctgttgaaag cagtaaactc atcagaaagg ataagtcatc atatggattt    300
gttcactact ttgatcgaag atccgctgct ctggctatac tgtctctgaa cggaaggcat    360
ctgtttggac agcctatcaa agtcaattgg gcgtatgcca ctggtcagag gaagatacag    420
tcaagtcatt tcaacatttt tgttggagat ctcagtccag aggtcactga tgcaacatta    480
tatcaaagct tttctgtctt ttccagttgt tcggatgcga gagttatgtg ggaccaaaaa    540
actgggcgct cgagaggctt tgggtttgtt tccttccgca atcaacagga tgctcaaact    600
gccattaatg agatgaatgg taagtggtta agtagcagac aaatcagatg caactgggcc    660
acgaagggcg ctacttctgg tgatgataag ctcagttctg atggaaaaag tgttgtggaa    720
cttacaactg gctcatcaga ggatggtaaa gagacattaa atgaggaaac acctgaaaat    780
aattctcagt ttaccactgt ttatgtggga aaccttgctc agaggtaac tcagcttgat     840
ctacaccgtt acttccatgc tcttggcgct ggagttattg aggaggtccg tgtccaacga    900
gacaaaggct ttggtttcgt gagatataac actcatcccg aagctgctct tgctattcag    960
atgggtaaca ctcagcctta cctctttaac agacagataa agtgctcatg ggaaacaag    1020
ccaactccac caggtacagc ctcaaaccca cttcccccac ctgccccagc tccagttcct   1080
ggtctatctg cagctgatct cctaaactat gagaggcaat tggcacttag caagatggca   1140
agtgtgaatg cgttaatgca tcaacagggt caacaccctc taaggcaggc tcatggaata   1200
aatgccgctg agcaactgc agccatgtat gatggtggct ttcagaatgt agccgccgca    1260
cagcaactca tgtactatca gtaa                                           1284
```

<210> SEQ ID NO 30
<211> LENGTH: 427
<212> TYPE: PRT
<213> ORGANISM: Arabidopsis thaliana

<400> SEQUENCE: 30

```
Met Gln Asn Pro Arg Leu Lys Gln His Gln Gln Gln Gln Gln Gln Gln
1               5                   10                  15
Ala Met Met Gln Gln Gln Ala Leu Met Gln Gln His Ser Leu Tyr His
                20                  25                  30
Pro Gly Val Leu Ala Pro Gln Leu Glu Pro Val Pro Ser Gly Asn
            35                  40                  45
Leu Pro Pro Gly Phe Asp Pro Ser Thr Cys Arg Ser Val Tyr Val Gly
        50                  55                  60
Asn Ile His Thr Gln Val Thr Glu Pro Leu Leu Gln Glu Ile Phe Thr
65                  70                  75                  80
Ser Thr Gly Pro Val Glu Ser Ser Lys Leu Ile Arg Lys Asp Lys Ser
                85                  90                  95
Ser Tyr Gly Phe Val His Tyr Phe Asp Arg Arg Ser Ala Ala Leu Ala
            100                 105                 110
Ile Leu Ser Leu Asn Gly Arg His Leu Phe Gly Gln Pro Ile Lys Val
        115                 120                 125
Asn Trp Ala Tyr Ala Thr Gly Gln Arg Glu Asp Thr Ser Ser His Phe
    130                 135                 140
Asn Ile Phe Val Gly Asp Leu Ser Pro Glu Val Thr Asp Ala Thr Leu
145                 150                 155                 160
Tyr Gln Ser Phe Ser Val Phe Ser Ser Cys Ser Asp Ala Arg Val Met
                165                 170                 175
```

Trp Asp Gln Lys Thr Gly Arg Ser Arg Gly Phe Gly Phe Val Ser Phe
            180                 185                 190

Arg Asn Gln Gln Asp Ala Gln Thr Ala Ile Asn Glu Met Asn Gly Lys
            195                 200                 205

Trp Leu Ser Ser Arg Gln Ile Arg Cys Asn Trp Ala Thr Lys Gly Ala
            210                 215                 220

Thr Ser Gly Asp Asp Lys Leu Ser Ser Asp Gly Lys Ser Val Val Glu
225                 230                 235                 240

Leu Thr Thr Gly Ser Ser Glu Asp Gly Lys Glu Thr Leu Asn Glu Glu
                245                 250                 255

Thr Pro Glu Asn Asn Ser Gln Phe Thr Thr Val Tyr Val Gly Asn Leu
            260                 265                 270

Ala Pro Glu Val Thr Gln Leu Asp Leu His Arg Tyr Phe His Ala Leu
            275                 280                 285

Gly Ala Gly Val Ile Glu Glu Val Arg Val Gln Arg Asp Lys Gly Phe
            290                 295                 300

Gly Phe Val Arg Tyr Asn Thr His Pro Glu Ala Ala Leu Ala Ile Gln
305                 310                 315                 320

Met Gly Asn Thr Gln Pro Tyr Leu Phe Asn Arg Gln Ile Lys Cys Ser
                325                 330                 335

Trp Gly Asn Lys Pro Thr Pro Pro Gly Thr Ala Ser Asn Pro Leu Pro
            340                 345                 350

Pro Pro Ala Pro Ala Pro Val Pro Gly Leu Ser Ala Ala Asp Leu Leu
            355                 360                 365

Asn Tyr Glu Arg Gln Leu Ala Leu Ser Lys Met Ala Ser Val Asn Ala
            370                 375                 380

Leu Met His Gln Gln Gly Gln His Pro Leu Arg Gln Ala His Gly Ile
385                 390                 395                 400

Asn Ala Ala Gly Ala Thr Ala Ala Met Tyr Asp Gly Gly Phe Gln Asn
                405                 410                 415

Val Ala Ala Ala Gln Gln Leu Met Tyr Tyr Gln
            420                 425

<210> SEQ ID NO 31
<211> LENGTH: 735
<212> TYPE: DNA
<213> ORGANISM: Saccharomyces cerevisiae

<400> SEQUENCE: 31
atggccgctg aaaaaatctt dacccccagaa tctcagttga agaagtctaa ggctcaacaa    60
aagactgctg aacaagtcgc tgctgaaaga gctgctcgta aggctgctaa caaggaaaag   120
agagccatta ttttggaaag aaacgccgct taccaaaagg aatacgaaac tgctgaaaga   180
aacatcattc aagctaagcg tgatgccaag gctgctggtt cctactacgt cgaagctcaa   240
cacaagttgg tcttcgttgt cagaatcaag ggtattaaca agatcccacc taagccaaga   300
aaggttctac aattgctaag attgacaaga atcaactctg gtacattcgt caaagttacc   360
aaggctactt tggaactatt tgaagttgatt gaaccatacg ttgcttacgg ttacccatcg   420
tactctacta ttagacaatt ggtctacaag agaggtttcg gtaagatcaa caagcaaaga   480
gttccattgt ccgacaatgc tatcatcgaa gccaacttgg gtaagtatgg atcttgtcc    540 attgacgatt tgattcacga aatcatcact gttggtccac acttcaagca agctaacaac   600 ttttttgtggc cattcaagtt gtccaaccca tctggtggtt ggggtgtccc aagaaagttc   660
aagcacttta tccaaggtgg ttctttcggt aaccgtgaag aattcatcaa caaattggtt   720
aagtccatga actaa                                                            735

<210> SEQ ID NO 32
<211> LENGTH: 244
<212> TYPE: PRT
<213> ORGANISM: Saccharomyces cerevisiae

<400> SEQUENCE: 32

Met Ala Ala Glu Lys Ile Leu Thr Pro Glu Ser Gln Leu Lys Lys Ser
1               5                   10                  15

Lys Ala Gln Gln Lys Thr Ala Glu Gln Val Ala Glu Arg Ala Ala
            20                  25                  30

Arg Lys Ala Ala Asn Lys Glu Lys Arg Ala Ile Ile Leu Glu Arg Asn
        35                  40                  45

Ala Ala Tyr Gln Lys Glu Tyr Glu Thr Ala Glu Arg Asn Ile Ile Gln
    50                  55                  60

Ala Lys Arg Asp Ala Lys Ala Ala Gly Ser Tyr Tyr Val Glu Ala Gln
65                  70                  75                  80

His Lys Leu Val Phe Val Arg Ile Lys Gly Ile Asn Lys Ile Pro
                85                  90                  95

Pro Lys Pro Arg Lys Val Leu Gln Leu Leu Arg Leu Thr Arg Ile Asn
            100                 105                 110

Ser Gly Thr Phe Val Lys Val Thr Lys Ala Thr Leu Glu Leu Leu Lys
        115                 120                 125

Leu Ile Glu Pro Tyr Val Ala Tyr Gly Tyr Pro Ser Tyr Ser Thr Ile
    130                 135                 140

Arg Gln Leu Val Tyr Lys Arg Gly Phe Gly Lys Ile Asn Lys Gln Arg
145                 150                 155                 160

Val Pro Leu Ser Asp Asn Ala Ile Ile Glu Ala Asn Leu Gly Lys Tyr
                165                 170                 175

Gly Ile Leu Ser Ile Asp Asp Leu Ile His Glu Ile Ile Thr Val Gly
            180                 185                 190

Pro His Phe Lys Gln Ala Asn Asn Phe Leu Trp Pro Phe Lys Leu Ser
        195                 200                 205

Asn Pro Ser Gly Gly Trp Gly Val Pro Arg Lys Phe Lys His Phe Ile
    210                 215                 220

Gln Gly Gly Ser Phe Gly Asn Arg Glu Glu Phe Ile Asn Lys Leu Val
225                 230                 235                 240

Lys Ser Met Asn

<210> SEQ ID NO 33
<211> LENGTH: 735
<212> TYPE: DNA
<213> ORGANISM: Saccharomyces cerevisiae

<400> SEQUENCE: 33
atgtccactg aaaaaatctt gactcctgaa tctcaattga agaagactaa agctcaacaa      60
aagactgcag aacaaattgc tgcagagaga gctgcccgta agccgctaa caaggaaaaa     120 agagctatta ttttggaaag aaacgccgct taccaaaagg aatacgaaac tgctgaaaga     180
aacatcattc aagctaagcg tgatgccaag gctgctggtt cctactacgt cgaagctcaa     240
cacaagttgg tcttcgttgt cagaatcaag ggtattaaca agattccacc taagccaaga     300
aaggttctac aattgctaag attgacaaga atcaactctg gtacattcgt caaagttacc     360
aaggctactt tggaactatt gaagttgatt gaaccatacg ttgcttacgg ttacccatcc     420

```
tactctacta ttagacaatt ggtctacaag agaggtttcg gtaagatcaa caagcaaaga    480
gttccattgt ccgacaatgc tatcatcgaa gccaacttgg gtaagtatgg tatcttgtcc    540
attgacgatt tgattcacga aatcatcact gttggtccac acttcaagca agctaacaac    600 ttttttgtggc cattcaagtt gtccaaccca tctggtggtt ggggtgtccc aagaaagttc    660
aagcatttca tccaaggtgg ttctttcggt aaccgtgaag aattcatcaa taaattggtt    720
aaggctatga actaa                                                    735

<210> SEQ ID NO 34
<211> LENGTH: 244
<212> TYPE: PRT
<213> ORGANISM: Saccharomyces cerevisiae

<400> SEQUENCE: 34

Met Ser Thr Glu Lys Ile Leu Thr Pro Glu Ser Gln Leu Lys Lys Thr
1               5                   10                  15

Lys Ala Gln Gln Lys Thr Ala Glu Gln Ile Ala Ala Glu Arg Ala Ala
            20                  25                  30

Arg Lys Ala Ala Asn Lys Glu Lys Arg Ala Ile Ile Leu Glu Arg Asn
        35                  40                  45

Ala Ala Tyr Gln Lys Glu Tyr Glu Thr Ala Glu Arg Asn Ile Ile Gln
    50                  55                  60

Ala Lys Arg Asp Ala Lys Ala Ala Gly Ser Tyr Tyr Val Glu Ala Gln
65                  70                  75                  80

His Lys Leu Val Phe Val Val Arg Ile Lys Gly Ile Asn Lys Ile Pro
                85                  90                  95

Pro Lys Pro Arg Lys Val Leu Gln Leu Leu Arg Leu Thr Arg Ile Asn
            100                 105                 110

Ser Gly Thr Phe Val Lys Val Thr Lys Ala Thr Leu Glu Leu Leu Lys
        115                 120                 125

Leu Ile Glu Pro Tyr Val Ala Tyr Gly Tyr Pro Ser Tyr Ser Thr Ile
    130                 135                 140

Arg Gln Leu Val Tyr Lys Arg Gly Phe Gly Lys Ile Asn Lys Gln Arg
145                 150                 155                 160

Val Pro Leu Ser Asp Asn Ala Ile Ile Glu Ala Asn Leu Gly Lys Tyr
                165                 170                 175

Gly Ile Leu Ser Ile Asp Asp Leu Ile His Glu Ile Ile Thr Val Gly
            180                 185                 190

Pro His Phe Lys Gln Ala Asn Asn Phe Leu Trp Pro Phe Lys Leu Ser
        195                 200                 205

Asn Pro Ser Gly Gly Trp Gly Val Pro Arg Lys Phe Lys His Phe Ile
    210                 215                 220

Gln Gly Gly Ser Phe Gly Asn Arg Glu Glu Phe Ile Asn Lys Leu Val
225                 230                 235                 240

Lys Ala Met Asn

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
```

-continued aaaaagcagg cttaatgcag caaccaccgt caaacgcc                              38

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agaaagctgg gtttcactga cgttgctgct gatagtt                               37

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aaaaagcagg cttaatgcag acaccaaaca acaacggt                              38

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agaaagctgg gtttcaagaa gctcccggga ctgcagc                               37

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aaaaagcagg cttaatgcag acaaccaacg gctcagat                              38

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agaaagctgg gtttcaattc tccccatgat agttgtt                               37

<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aaaaagcagg cttaatggca gacgtcaaga ttcaatcc                              38

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
agaaagctgg gtttcagcta acttgttgct gatgacc        37

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
aaaaagcagg cttaatggca gacgtcaagg ttcaatcc        38

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
agaaagctgg gtttcagcta acttgttgct gatgacc        37

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
aaaaagcagg cttaatgcag aatcaaaggc ttattaag        38

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
agaaagctgg gttttactga tagtacatga gctgctg        37

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
aaaaagcagg cttaatgtcc actgaaaaaa tctt        34

```
<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agaaagctgg gttttagttc atagccttaa cca                                    33

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aatctgtgtc gacgtacttc                                                   20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agaagtacat aggatgggtc                                                   20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aaaaattgtc gacgtacttc                                                   20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaaggaagtt atcacaattg                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccagcatcta tgtctgcaac                                                   20
```

```
<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cgtatctgga gtagtatttc                                            20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcaaggtata caaagcagaa                                            20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcatcctttt tcttctctgc                                            20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gacacgatga agttggatat                                            20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgactgtcaa atcatcactg                                            20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cagtataaaa atgtctgaat                                            20

<210> SEQ ID NO 60
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tggttgatta tttcttcttc                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
atcaacgtca taatgtccac                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
taccagagtt gattcttgtc                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acctaaagaa accatgtcag                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tatcaaggtt gtacgtttcg                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
atgtacagtc taagtcaagg                                              20

<210> SEQ ID NO 66
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gactaaagtg aacagcaatg                                                  20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gagaatggca atatttcaag                                                  20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tgttcttctt cttccattac                                                  20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tggacccaca taatccaatt                                                  20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tttcgaacat tacctcacac                                                  20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gtggatggtc ttttagaaga                                                  20

<210> SEQ ID NO 72
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 72
aactcctcga aacttaaacg                                             20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tattgagacc ttcttccaag                                             20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aagattttac cggaaacgtg                                             20

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gacgataaaa agaaatttgg tg                                          22

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ctcaaagcgt tgttgaaag                                              19

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gagagaggtc attagtatta                                             20

<210> SEQ ID NO 78
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 78
ttttctaata acagggaacc                                                    20

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gtttaataga aaagaagag gag                                                 23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tagttcatca actaaaaaca tgg                                                23

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
agctgtccca agtgttcaa                                                     19

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
acccttacca ccgaatttc                                                     19

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gttgggatat ttttggttgg                                                    20

<210> SEQ ID NO 84
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 84
aaaggaacgt ccttcaattc                                               20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
aacaagctgt tcaggttaga                                               20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ggtttgtgat tatcatcagg                                               20

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
aattaaagat cacaatggcc g                                             21

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cttggtaact ttgacgaatg                                               20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cagaaaagct ggtgttcaag                                               20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 90
tgattctgca tcgtggtttc                                               20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ttgattaaga actccaaagc                                               20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tcttctcaag acacgtaatc                                               20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
agatgaggtt gaagcaatag                                               20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
caagggcaat ttccttattg                                               20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
taagactaag caacaatgcc                                               20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 96
aaacccaact tgtagacttg                                              20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gcatctcata atatgtctgc                                              20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ttgttgctaa gactgtagag                                              20

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
caaatccatt tcaaaatata gg                                           22

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ctcctcctat ctaaaaaacc                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
aagaagagtt ggtaagcaag                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 102
caccgttttt gaatgtgatg                                                    20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
agcgtaatac gaaagatgag                                                    20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
agcttcgtta ttcaagggat                                                    20

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gtatcataaa cattcaacaa tg                                                 22

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cggatctgtt gtttattctc                                                    20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
aaacaaagtt tgatcgcctc                                                    20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
```
tcgtgctcaa acatttcttc                                          20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
aaaatgacgg ataatccacc                                          20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ttcaaagtct ttagcacacc                                          20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
caatccatca tgggaaaatc                                          20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cttggacgac aaaatagtgt                                          20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aggacttcaa tttccatgtc                                          20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114

-continued agtgtcatct ccacaatttg                                             20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gaaaacgata agggccaatt                                             20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116 cgttcttaa caaaccatcg                                              20

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
taccaaatga aacgctttaa tg                                          22

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tcttcatgga aagagtctag                                             20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
atggaatgag tactttagcg                                             20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
cttcatttcc gagttttgg                                              20

```
<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aatagaaaat cggcttctgc                                                    20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tatttgatca ttggggttgc                                                    20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gattgaagac atttgatgcg                                                    20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcgccactaa ctctatttac                                                    20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
accatttcag gtacaatgtc                                                    20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cttcggaaat atcgaattcc                                                    20
```

```
<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ctgaaacgat accaacaatg                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tttgtggttt aggcaatacc                                              20

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
atacaaaagt atacaacatg cc                                           22

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tttccaagaa atcttcgacc                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ctttactgcg aagataaagg                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gccactataa tctgttgttg                                              20
```

```
<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
tcaaaactac ggctcatttg                                                     20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tgaacaaaag actcaatccg                                                     20
```